(12) United States Patent
Dhalla et al.

(10) Patent No.: US 7,939,509 B2
(45) Date of Patent: *May 10, 2011

(54) PARTIAL AND FULL AGONISTS OF A₁ ADENOSINE RECEPTORS

(75) Inventors: Arvinder Dhalla, Mountain View, CA (US); Elfatih Elzein, Fremont, CA (US); Prabha Ibrahim, Mountain View, CA (US); Venkata Palle, Pune (IN); Vaibhav Varkhedkar, Chalfont, PA (US); Jeff Zablocki, Los Altos, CA (US)

(73) Assignee: Gilead Sciences, Inc., Foster City, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 12/724,255

(22) Filed: Mar. 15, 2010

(65) Prior Publication Data

US 2010/0210579 A1    Aug. 19, 2010

Related U.S. Application Data

(63) Continuation of application No. 11/641,234, filed on Dec. 18, 2006, now Pat. No. 7,713,946, which is a continuation-in-part of application No. 10/855,471, filed on May 27, 2004, now Pat. No. 7,157,440, which is a continuation-in-part of application No. 10/194,335, filed on Jul. 11, 2002, now Pat. No. 6,946,449.

(51) Int. Cl.
*A01N 43/04* (2006.01)
*A61K 31/70* (2006.01)

(52) U.S. Cl. .................................................. 514/46

(58) Field of Classification Search .................. None
See application file for complete search history.

(56) References Cited

U.S. PATENT DOCUMENTS

| | | | |
|---|---|---|---|
| 3,845,770 A | 11/1974 | Theeuwes et al. | |
| 4,326,525 A | 4/1982 | Swanson et al. | |
| 4,902,514 A | 2/1990 | Barclay et al. | |
| 4,992,445 A | 2/1991 | Lawter et al. | |
| 5,001,139 A | 3/1991 | Lawter et al. | |
| 5,023,252 A | 6/1991 | Hseih | |
| 5,616,345 A | 4/1997 | Geoghegan et al. | |
| 6,258,793 B1 | 7/2001 | Palle et al. | |
| 6,946,449 B2 * | 9/2005 | Elzein et al. | 514/46 |
| 7,157,440 B2 * | 1/2007 | Elzein et al. | 514/46 |
| 7,655,638 B2 | 2/2010 | Elzein et al. | |
| 7,713,946 B2 * | 5/2010 | Dhalla et al. | 514/46 |
| 2003/0050275 A1 | 3/2003 | Elzein et al. | |
| 2003/0216349 A1 | 11/2003 | Belardinelli et al. | |
| 2003/0232783 A1 | 12/2003 | Ibrahim et al. | |
| 2006/0009417 A1 | 1/2006 | Elzein et al. | |
| 2007/0066560 A1 | 3/2007 | Elzein et al. | |

FOREIGN PATENT DOCUMENTS

| | | |
|---|---|---|
| EP | 0181129 A2 | 5/1986 |
| RO | 116401 B | 1/2001 |
| WO | WO-9924449 A2 | 5/1999 |
| WO | WO-9924450 A2 | 5/1999 |
| WO | WO-9924451 A2 | 5/1999 |
| WO | WO-9967262 A1 | 12/1999 |
| WO | WO-0140243 A2 | 6/2001 |

OTHER PUBLICATIONS

Dhalia et al., Current topics in Medicinal Chemistry, 2003, 369-385.*
B. Lerman and L. Belardinelli Circulation, vol. 83 (1991), p. 1499-1509.
Brackett L E et al: "Functional Characterization of the A2B Adenosine Receptor in NIH 3T3 Fibroblasts", Biochemical Pharmacology, Pergamon, Oxford, GB, vol. 47, No. 5, 1994, pp. 801-814 XP000942545, ISSN: 0006-2952 abstract.
C. Shryock and L. Belardinelli, Am. J. Cardiology, vol. 79 (1997) p. 2-10.
D. Thiebaud et al Metab. Clin. Exp. vol. 31 (1982) p. 1128-1136.
Dhalia et al., Current Topics in Medicinal Chemistry, 2003, 3, 369-385.
Dhalla, Arvinder et al., "Antilipolytic Activity of a Novel partial A(1) Adenosine Receptor Agonist Devoid of Cardiovascular Effects: Comparison with Nicotinic Acid", Journal of Pharmacology and Experimental Therapeutics, vol. 321, No. 1 Apr. 2007,pp. 327-333.
DMCM, H. Klitgaard Eur, J. Pharmacol. (1993) vol. 224 p. 221-228.
E. A. van Schaick et al J. Pharmacokinetics and Biopharmaceutics, vol. 25 (1997) p. 673-694.
Fatholahi, Marjan et al., "A Novel Partial Agonist of the A(1)-Adenosine Receptor and Evidence of Receptor Homogeneity in Adipocytes", Journal of Pharmacology and Experimental Therapeutics, vol. 317, No. 2, May 2006, pp. 676-684.
Feoktistov et al., Adenosine A.sub.2B Receptors as Therapeutic Targets, Drug Dev Res 45:198; Trends Pharmacol Sci, (1998), 19:148-153.
G. Boden et al J. Clin. Invest. vol. 93 (1994) p. 2438-2446.
G. Zhang et al. Eur. J. Pharmacol. vol. 255 (1994) p. 239-243.
International Search Report mailed Apr. 24, 2008 for PCT Appln. No. PCT/US2007/087957, filed Dec. 18, 2007.
K. Kato et. al. J. Org. Chem. 1997, 62, 6833-6841.
Knutsen et al (J. Med. Chem. vol. 42 (1999) p. 3463-3477.

(Continued)

Primary Examiner — Traviss C McIntosh, III

(57) ABSTRACT

Disclosed are novel compounds a compound of Formula I

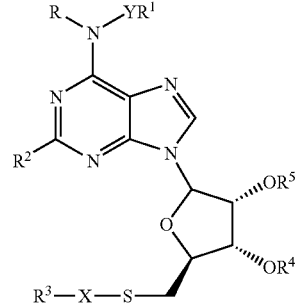

Formula I that are partial and full A₁ adenosine receptor agonists, useful for treating various disease states, in particular dyslipidemia, diabetes, decreased insulin sensitivity, Polycystic Ovarian Syndrome, Stein-Leventhal syndrome, and obesity.

13 Claims, 12 Drawing Sheets

OTHER PUBLICATIONS

L. J. S. Knutsen and T. F. Murray in Purinergic Approaches in Experimental Therapeutics, Eds. K. A. Jacobson and M. F. Jarvis (1997) Wiley-Liss, N. Y., p. -423-470.

L. J. S. Knutsen in Adenosine and Adenine Nucleotides: From Molecular Biology to Integrative Physiology; eds. L. Belardinelli and A. Pelleg, Kluwer: Boston, 1995, pp. 479-487.

Lorenzen et al. European Journal of Pharmacology, 244, (1993) p. 223-230.

Marumoto R. et al: "Synthesis and Enzymatic Activity of Adenosine 3',5'-Cyclic Phosphate Analogs", Chemical and Pharmaceutical Bulletin, Pharmaceutical Society of Japan. Tokyo, JP., vol. 27, No. 4, 1979, pp. 990-1003, ISSN: 0009-2363, *chart 3*, p. 992, table 3.

Morrison, Christopher et al., "Structure-affinity Relationships of 5'-Aromatic Ethers and 5'-Aromatic Sulfides as Partial A1 Adenosine Agonists, Potential Supraventricular Anti-Arrhythmic Agents", Bioorganic & Medicinal Chemistry Letters, vol. 14,No. 14, Jul. 2004, pp. 3793-3797.

Munro R et al, "Differential expression of adenosine A2A and A2B receptor subtypes of myeloid U937 and THP-1 cells: Adenosine A2B receptor activation selectively stimulates cAMP formation and inhibition of TNFalpha release in THP-1 cells." DrugDevelopment Research, vol. 44, No. 1, May 1998, pp. 41-47 ISSN: 0272-4391.

P. J. Randle et al Lancet (1963) p. 785-789.

P. Strong Clinical Science vol. 84 (1993) p. 663-669.

R. B. Clark, B. J. Knoll, R. Barber TiPS, vol. 20 (1999) p. 279-286.

Smejkal, R.M. et al: "Muscarinic receptor subtype specificity of 5'(isobutylthio)-adenosine (SIBA) and its analogues", Gen Pharmac., 1989, 20(3) pp. 385-392.

Tilburg, E. et al: "N6 5'-Disubstituted adenosine derivatives as partial agonists for the human adenosine A3 receptor", J. Med Chem, 1999, 42, pp. 1393-1400.

Traynor et al. American Society for Pharmacology and Experimental Therapeutics, 47, (1995), p. 848-854.

Van Der Wenden, E. et al: "5'-Substituted adenosine analogs as new high-affinity partial agonists for the adenosine A1 receptor" J. Med Chem 1998, 41, pp. 102-108.

* cited by examiner

A

B

A

B

C

A

B

PARTIAL AND FULL AGONISTS OF $A_1$ ADENOSINE RECEPTORS

This application is a Continuation of U.S. patent application Ser. No. 11/641,234, filed Dec. 18, 2006, now U.S. Pat. No. 7,713,946, which is a Continuation in Part of U.S. patent application Ser. No. 10/855,471, filed May 27, 2004, which issued on Jan. 2, 2007 as U.S. Pat. No. 7,157,440 which is a Continuation in Part of U.S. patent application Ser. No. 10/194,335 filed Jul. 11, 2002, which issued Sep. 20, 2005 as U.S. Pat. No. 6,946,449, the entirety of which are all incorporated herein.

FIELD OF THE INVENTION

The present invention relates to novel compounds that are partial or full $A_1$ adenosine receptor agonists, and to their use in treating mammals for various disease states, including modifying cardiac activity, in particular treatment of arrhythmia. The compounds are also useful for treating CNS disorders, diabetic disorders, elevated lipid levels, decreased insulin sensitivity, Polycystic Ovarian Syndrome, Stein-Leventhal syndrome, obesity, and modifying adipocyte function as well as for the treatment of metabolic syndrome and the like. The invention also relates to methods for their preparation, and to pharmaceutical compositions containing such compounds.

BACKGROUND

Adenosine is a naturally occurring nucleoside, which exerts its biological effects by interacting with a family of adenosine receptors known as $A_1$, $A_{2a}$, $A_{2b}$, and $A_3$, all of which modulate important physiological processes. For example, $A_{2A}$ adenosine receptors modulate coronary vasodilation, $A_{2B}$ receptors have been implicated in mast cell activation, asthma, vasodilation, regulation of cell growth, intestinal function, and modulation of neurosecretion (See Adenosine $A_{2B}$ Receptors as Therapeutic Targets, *Drug Dev Res* 45:198; Feoktistov et al., *Trends Pharmacal Sci* 19:148-153), and $A_3$ adenosine receptors modulate cell proliferation processes.

The $A_1$ adenosine receptor mediates two distinct physiological responses. Inhibition of the cardiostimulatory effects of catecholamine is mediated via the inhibition of adenylate cyclase, whereas the direct effects to slow the heart rate (HR) and to prolong impulse propagation through the AV node are due in great part to activation of $I_{KAdo}$. (B. Lerman and L. Belardinelli *Circulation*, Vol. 83 (1991), P 1499-1509 and J. C. Shryock and L. Belardinelli, *Am. J. Cardiology*, Vol. 79 (1997) P 2-10). Stimulation of the $A_1$ adenosine receptor shortens the duration and decreases the amplitude of the action potential of AV nodal cells, and hence prolongs the refractory period of the AV nodal cell. Thus, stimulation of $A_1$ receptors provides a method of treating supraventricular tachycardias, including termination of nodal re-entrant tachycardias, and control of ventricular rate during atrial fibrillation and flutter.

Accordingly, $A_1$ adenosine agonists are useful in the treatment of acute and chronic disorders of heart rhythm, especially those diseases characterized by rapid heart rate, in which the rate is driven by abnormalities in the sinoatrial, atria, and AV nodal tissues. Such disorders include, but are not limited to, atrial fibrillation, supraventricular tachycardia and atrial flutter. Exposure to $A_1$ agonists causes a reduction in the heart rate and a regularization of the abnormal rhythm, thereby improving cardiovascular function.

$A_1$ agonists, through their ability to inhibit the effects of catecholamines, decrease cellular cAMP, and thus have beneficial effects in the failing heart where increased sympathetic tone increases cellular cAMP levels. The latter condition has been shown to be associated with increased likelihood of ventricular arrhythmias and sudden death. See, for example, B. Lerman and L. Belardinelli *Circulation*, Vol. 83 (1991), P 1499-1509 and J. C. Shryock and L. Belardinelli, *Am. J. Cardiology*, Vol. 79 (1997) P 2-10.

$A_1$ agonists, as a result of their inhibitory action on cyclic AMP generation, have antilipolytic effects in adipose tissue that results in a decreased release of nonesterified fatty acids (NEFA) into plasma (E. A. van Schaick et al *J. Pharmacokinetics and Biopharmaceutics*, Vol. 25 (1997) p 673-694 and P. Strong *Clinical Science* Vol. 84 (1993) p. 663-669). Non-insulin-dependent diabetes mellitus (NIDDM) is characterized by insulin resistance that results in hyperglycemia. Factors contributing to the observed hyperglycemia are lack of normal glucose uptake and activation of skeletal muscle glycogen synthase (GS). Elevated levels of NEFA have been shown to inhibit insulin-stimulated glucose uptake and glycogen synthesis (D. Thiebaud et al *Metab. Clin. Exp.* Vol. 31 (1982) p 1128-1136 and G. Boden et al *J. Clin. Invest*. Vol. 93 (1994) p 2438-2446). The hypothesis of a glucose fatty acid cycle was proposed by P. J. Randle as early as 1963 (P. J. Randle et al *Lancet* (1963) p. 785-789). A tenet of this hypothesis would be that limiting the supply of fatty acids to the peripheral tissues should promote carbohydrate utilization (P. Strong et al *Clinical Science* Vol. 84 (1993) p. 663-669).

The benefit of an $A_1$ agonist in central nervous disorders has been reviewed (L. J. S. Knutsen and T. F. Murray in *Purinergic Approaches in Experimental Therapeutics*, Eds. K. A. Jacobson and M. F. Jarvis (1997) Wiley-Liss, N.Y., P-423-470). Briefly, based on experimental models of epilepsy, a mixed $A_{2A}$:$A_1$ agonist, metrifudil, has been shown to be a potent anticonvulsant against seizures induced by the inverse benzodiazepine agonist methyl 6,7-dimethoxy-4-ethyl-beta-carboline-3-carboxylate (DMCM, H. Klitgaard *Eur. J. Pharmacol.* (1993) Vol. 224 p. 221-228). In other studies using CGS 21680, an $A_{2A}$ agonist, it was concluded that the anticonvulsant activity was attributed to activation of the $A_1$ receptor (G. Zhang et al. *Eur. J. Pharmacol*. Vol. 255 (1994) p. 239-243). Furthermore, $A_1$ adenosine selective agonists have been shown to have anticonvulsant activity in the DMCM model (L. J. S. Knutsen In *Adenosine and Adenine Nucleotides From Molecular Biology to Integrative Physiology*; eds. L. Belardinelli and A. Pelleg, Kluwer: Boston, 1995, pp 479-487). A second area where an $A_1$ adenosine agonist has a benefit is in animal models of forebrain ischemia as demonstrated by Knutsen et al (*J. Med. Chem*. Vol. 42 (1999) p. 3463-3477). The benefit in neuroprotection is believed to be in part due to the inhibition of the release of excitatory amino acids (ibid).

Adenosine itself has proven effective in treating disease states related to the $A_1$ adenosine receptor, for example in terminating paroxysmal supraventricular tachycardia. However, these effects are short-lived because adenosine's half-life is less than 10 sec. Additionally, as adenosine acts indiscriminately on the $A_{2A}$, $A_{2B}$, and the $A_3$ adenosine receptor subtypes, it also provides direct effects on sympathetic tone, coronary vasodilatation, systemic vasodilatation and mast cell degranulation.

Accordingly, it is an object of this invention to provide compounds that are potent full $A_1$ adenosine receptor agonists or partial $A_1$ receptor agonists with a half life greater than that of adenosine, and that are selective for the $A_1$ adenosine receptor, which will ensure that undesired side effects related to stimulation or antagonism of the other adenosine receptors are avoided.

SUMMARY OF THE INVENTION

It is an object of this invention to provide compounds that are selective, partial or full $A_1$ receptor agonists. Accordingly, in a first aspect, the invention relates to compounds of Formula I:

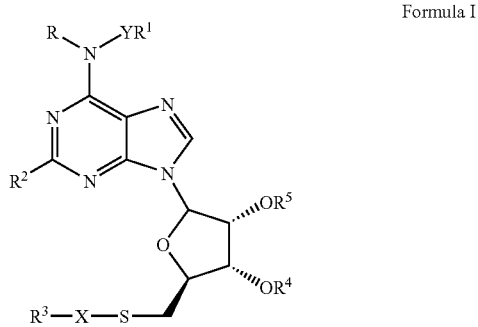

Formula I wherein:
R is hydrogen;
$R^1$ is optionally substituted alkyl, optionally substituted cycloalkyl, optionally substituted aryl, or optionally substituted heteroaryl; or
R and $YR^1$ when taken together with the nitrogen atom to which they are attached represents optionally substituted heterocyclyl;
$R^2$ is hydrogen, halo, trifluoromethyl, acyl, or cyano;
$R^3$ is optionally substituted cycloalkyl, optionally substituted aryl; optionally substituted heteroaryl, or optionally substituted heterocyclyl,
$R^4$ and $R^5$ are independently hydrogen or acyl; and
X and Y are independently a covalent bond or optionally substituted alkylene;
with the proviso that when $R^1$ is methyl and Y is a covalent bond, $R^3$ cannot be phenyl when X is methylene or ethylene.

A second aspect of this invention relates to pharmaceutical formulations, comprising a therapeutically effective amount of a compound of Formula I and at least one pharmaceutically acceptable excipient.

A third aspect of this invention relates to a method of using the compounds of Formula I in the treatment of a disease or condition in a mammal that can be usefully treated with a partial or full selective $A_1$ receptor agonist. Such diseases include atrial fibrillation, supraventricular tachycardia and atrial flutter, congestive heart failure, antilipolytic effects in adipocytes, epilepsy, stroke, dyslipidemia, obesity, diabetes, insulin resistance, decreased glucose tolerance, non-insulin-dependent diabetes mellitus, Type II diabetes, Type I diabetes, and other diabetic complications, ischemia, including stable angina, unstable angina, cardiac transplant, and myocardial infarction.

Of the compounds of Formula I, one preferred class includes those in which $R^3$ is optionally substituted aryl or optionally substituted heteroaryl, especially where R, $R^2$, $R^4$ and $R^5$ are all hydrogen.

Of these compounds, one preferred group includes compounds in which $R^3$ is optionally substituted aryl, especially those in which $R^3$ is optionally substituted phenyl, $R^1$ is optionally substituted cycloalkyl, and X is a covalent bond. A preferred subgroup includes those compounds in which $R^3$ is phenyl substituted by halo, especially fluoro, and $R^1$ is optionally substituted cyclopentyl, especially 2-hydroxycyclopentyl.

A second preferred subgroup includes compounds in which $R^1$ and $R^3$ are both optionally substituted phenyl, X is a covalent bond, and Y is optionally substituted lower alkylene, especially those compounds in which Y is ethylene, propylene or propylene substituted by phenyl.

A third preferred subgroup includes compounds in which $R^1$ is optionally substituted alkyl or optionally substituted phenyl, $R^3$ is optionally substituted phenyl, and X and Y are both covalent bonds. A preferred subgroup includes those compounds in which $R^1$ is lower alkyl or 2-fluorophenyl and $R^3$ is phenyl or 2-fluorophenyl.

Another preferred group includes compounds in which $R^3$ is optionally substituted heteroaryl, especially those in which $R^3$ is optionally substituted 1,3-thiazol-2-yl or optionally substituted 1,3-benzoxazol-2-yl. A preferred subgroup includes those compounds in which $R^1$ is optionally substituted cycloalkyl or optionally substituted phenyl, X is a covalent bond, and Y is a covalent bond or alkylene. A more preferred subgroup includes those compounds in which $R^1$ is bicycloalkyl, particularly bicyclo[2.2.1]hepty-2-yl, and Y is a covalent bond, or $R^1$ is monocyclic, especially cyclopropyl, and Y is methylene. Another preferred subgroup includes those compounds in which $R^1$ is phenyl and Y is lower alkylene.

A second preferred class includes those compounds in which. $R^2$, $R^4$ and $R^5$ are all hydrogen, and R and $YR^1$ when taken together with the nitrogen to which they are attached represent a nitrogen containing heterocyclyl. A preferred group includes those compounds in which $R^3$ is optionally substituted phenyl or optionally substituted heteroaryl and X is a covalent bond, especially where R and $YR^1$ when taken together with the nitrogen to which they are attached represents pyrrolidin-1-yl.

DETAILED DESCRIPTION OF THE INVENTION

Definitions and General Parameters

Figure 1:
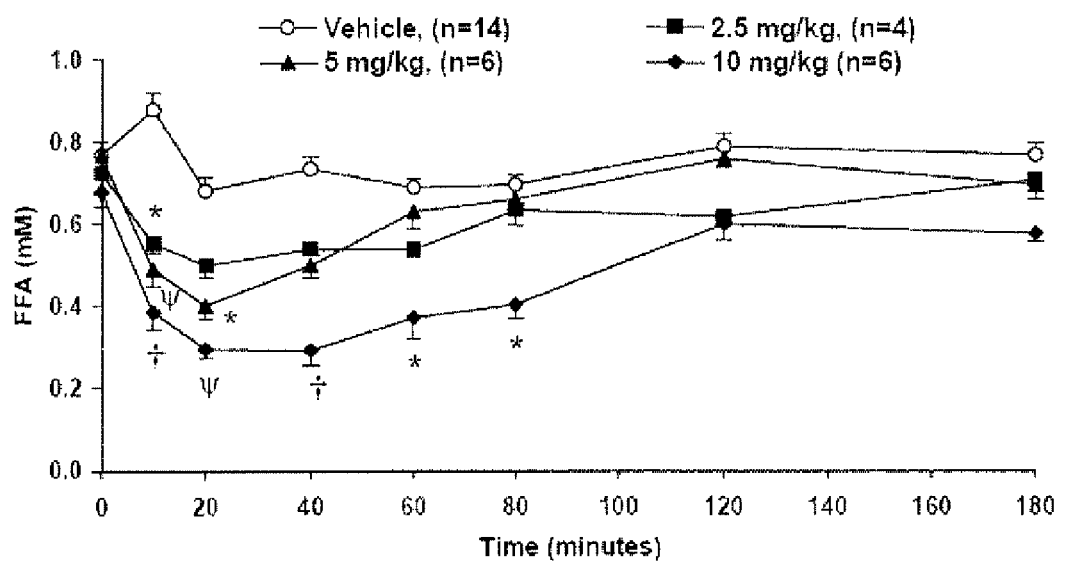
FIG. 1 graphically illustrates the anti-lipolytic effect of the partial $A_1$ agonist, Compound A. Shown is the time-course of the effect of various does of Compound A on circulating free fatty acids (FFA) in awake rats. Three does (2.5, 5, and 10 mg/kg) of Compound A were administered via oral gavage after an overnight fast. Each symbol represents the mean±SEM of the FFA levels from a number of rats for each group. *) $p<0.05$, Ψ) $p<0.01$.

As used in the present specification, the following words and phrases are generally intended to have the meanings as set forth below, except to the extent that the context in which they are used indicates otherwise.

The term "alkyl" refers to a monoradical branched or unbranched saturated hydrocarbon chain having from 1 to 20 carbon atoms. This term is exemplified by groups such as methyl, ethyl, n-propyl, iso-propyl, n-butyl, iso-butyl, t-butyl, n-hexyl, n-decyl, tetradecyl, and the like.

The term "substituted alkyl" refers to:

1) an alkyl group as defined above, having from 1 to 5 substituents, preferably 1 to 3 substituents, selected from the group consisting of alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —$SO_2$-aryl and —$SO_2$-heteroaryl. Unless otherwise constrained by the definition, all substituents may optionally be further substituted by 1-3 substituents chosen from alkyl, carboxy, carboxyalkyl, aminocarbonyl, hydroxy, alkoxy, halogen, $CF_3$, amino, substituted amino, cyano, and —$S(O)_nR$, where R is alkyl, aryl, or heteroaryl and n is 0, 1 or 2; or 2) an alkyl group as defined above that is interrupted by 1-5 atoms or groups independently chosen from oxygen, sulfur and —$NR_a$—, where $R_a$ is chosen from hydrogen, alkyl, cycloalkyl, alkenyl, cycloalkenyl, alkynyl, aryl, heteroaryl and heterocyclyl. All substituents may be optionally further substituted by alkyl, alkoxy, halogen, $CF_3$, amino, substituted amino, cyano, or —$S(O)_nR$, in which R is alkyl, aryl, or heteroaryl and n is 0, 1 or 2; or 3) an alkyl group as defined above that has both from 1 to 5 substituents as defined above and is also interrupted by 1-5 atoms or groups as defined above.

The term "lower alkyl" refers to a monoradical branched or unbranched saturated hydrocarbon chain having from 1 to 6 carbon atoms. This term is exemplified by groups such as methyl, ethyl, n-propyl, iso-propyl, n-butyl, iso-butyl, t-butyl, n-hexyl, and the like.

The term "substituted lower alkyl" refers to lower alkyl as defined above having 1 to 5 substituents, preferably 1 to 3 substituents, as defined for substituted alkyl, or a lower alkyl group as defined above that is interrupted by 1-5 atoms as defined for substituted alkyl, or a lower alkyl group as defined above that has both from 1 to 5 substituents as defined above and is also interrupted by 1-5 atoms as defined above.

The term "alkylene" refers to a diradical of a branched or unbranched saturated hydrocarbon chain, preferably having from 1 to 20 carbon atoms, preferably 1-10 carbon atoms, more preferably 1-6 carbon atoms. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

The term "lower alkylene" refers to a diradical of a branched or unbranched saturated hydrocarbon chain having from 1 to 6 carbon atoms.

The term "substituted alkylene" refers to:
(1) an alkylene group as defined above having from 1 to 5 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-aryl and —SO$_2$-heteroaryl. Unless otherwise constrained by the definition, all substituents may optionally be further substituted by 1-3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2; or
(2) an alkylene group as defined above that is interrupted by 1-5 atoms or groups independently chosen from oxygen, sulfur and NR$_a$— where R$_a$ is chosen from hydrogen, optionally substituted alkyl, cycloalkyl, cycloalkenyl, aryl, heteroaryl and heterocycyl, or groups selected from carbonyl, carboxyester, carboxyamide and sulfonyl; or
(3) an alkylene group as defined above that has both from 1 to 5 substituents as defined above and is also interrupted by 1-20 atoms as defined above. Examples of substituted alkylenes are chloromethylene (—CH(Cl)—), aminoethylene (—CH(NH$_2$)CH$_2$—), methylaminoethylene (—CH(NHMe)CH$_2$—), 2-carboxypropylene isomers (—CH$_2$CH(CO$_2$H)CH$_2$—), ethoxyethyl (—CH$_2$CH$_2$O—CH$_2$CH$_2$—), ethylmethylaminoethyl (—CH$_2$CH$_2$N(CH$_3$)CH$_2$CH$_2$—), 1-ethoxy-2-(2-ethoxy-ethoxy)ethane (—CH$_2$CH$_2$O—CH$_2$CH$_2$—OCH$_2$CH$_2$—OCH$_2$CH$_2$—), and the like.

The term "aralkyl: refers to an aryl group covalently linked to an alkylene group, where aryl and alkylene are defined herein. "Optionally substituted aralkyl" refers to an optionally substituted aryl group covalently linked to an optionally substituted alkylene group. Such aralkyl groups are exemplified by benzyl, 3-(4-methoxyphenyl)propyl, and the like.

The term "alkoxy" refers to the group R—O—, where R is optionally substituted alkyl or optionally substituted cycloalkyl, or R is a group —Y—Z, in which Y is optionally substituted alkylene and Z is; optionally substituted alkenyl, optionally substituted alkynyl; or optionally substituted cycloalkenyl, where alkyl, alkenyl, alkynyl, cycloalkyl and cycloalkenyl are as defined herein. Preferred alkoxy groups are alkyl-O— and include, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

The term "alkylthio" refers to the group R—S—, where R is as defined for alkoxy.

The term "alkenyl" refers to a monoradical of a branched or unbranched unsaturated hydrocarbon group preferably having from 2 to 20 carbon atoms, more preferably 2 to 10 carbon atoms and even more preferably 2 to 6 carbon atoms and having 1-6, preferably 1, double bond (vinyl). Preferred alkenyl groups include ethenyl or vinyl 1-propylene or allyl isopropylene (—C(CH$_3$)=CH$_2$), bicyclo[2.2.1]heptene, and the like. In the event that alkenyl is attached to nitrogen, the double bond cannot be alpha to the nitrogen.

The term "lower alkenyl" refers to alkenyl as defined above having from 2 to 6 carbon atoms.

The term "substituted alkenyl" refers to an alkenyl group as defined above having from 1 to 5 substituents, and preferably 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, acyloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1-3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "alkynyl" refers to a monoradical of an unsaturated hydrocarbon, preferably having from 2 to 20 carbon atoms, more preferably 2 to 10 carbon atoms and even more preferably 2 to 6 carbon atoms and having at least 1 and preferably from 1-6 sites of acetylene (triple bond) unsaturation. Preferred alkynyl groups include ethynyl, (—C≡CH), propargyl (or propynyl, —C≡CCH$_3$), and the like. In the event that alkynyl is attached to nitrogen, the triple bond cannot be alpha to the nitrogen.

The term "substituted alkynyl" refers to an alkynyl group as defined above having from 1 to 5 substituents, and preferably 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1-3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "aminocarbonyl" refers to the group —C(O)NRR where each R is independently hydrogen, alkyl, aryl, heteroaryl, heterocyclyl or where both R groups are joined to form a heterocyclic group (e.g., morpholino). All substituents may be optionally further substituted by alkyl, alkoxy, halogen, CF$_3$, amino, substituted amino, cyano, or —S(O)$_n$R, in which R is alkyl, aryl, or heteroaryl and n is 0, 1 or 2.

The term "acylamino" refers to the group —NRC(O)R where each R is independently hydrogen, alkyl, aryl, heteroaryl, or heterocyclyl. All substituents may be optionally further substituted by alkyl, alkoxy, halogen, CF$_3$, amino, substituted amino, cyano, or —S(O)$_n$R, in which R is alkyl, aryl, or heteroaryl and n is 0, 1 or 2.

The term "acyloxy" refers to the groups —O(O)C-alkyl, —O(O)C-cycloalkyl, —O(O)C-aryl, —O(O)C-heteroaryl, and —O(O)C-heterocyclyl. All substituents may be optionally further substituted by alkyl, alkoxy, halogen, $CF_3$, amino, substituted amino, cyano, or —S(O)$_n$R, in which R is alkyl, aryl, or heteroaryl and n is 0, 1 or 2.

The term "aryl" refers to an aromatic carbocyclic group of 6 to 20 carbon atoms having a single ring (e.g., phenyl) or multiple rings (e.g., biphenyl), or multiple condensed (fused) rings (e.g., naphthyl or anthryl). Preferred aryls include phenyl, naphthyl and the like.

Unless otherwise constrained by the definition for the aryl substituent, such aryl groups can optionally be substituted with from 1 to 5 substituents, preferably 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1-3 substituents chosen from alkyl, carboxy, carboxyalkyl, aminocarbonyl, hydroxy, alkoxy, halogen, $CF_3$, amino, substituted amino, cyano, and —S(O)$_n$R, where R is alkyl, aryl, or heteroaryl and n is 0, 1 or 2.

The term "aryloxy" refers to the group aryl-O— wherein the aryl group is as defined above, and includes optionally substituted aryl groups as also defined above. The term "arylthio" refers to the group R—S—, where R is as defined for aryl.

The term "amino" refers to the group —NH$_2$.

The term "substituted amino" refers to the group —NRR where each R is independently selected from the group consisting of hydrogen, alkyl, cycloalkyl, carboxyalkyl (for example, benzyloxycarbonyl), aryl, heteroaryl and heterocyclyl provided that both R groups are not hydrogen, or a group —Y—Z, in which Y is optionally substituted alkylene and Z is alkenyl, cycloalkenyl, or alkynyl. Unless otherwise constrained by the definition, all substituents may optionally be further substituted by 1-3 substituents chosen from alkyl, carboxy, carboxyalkyl, aminocarbonyl, hydroxy, alkoxy, halogen, $CF_3$, amino, substituted amino, cyano, and —S(O)$_n$R, where R is alkyl, aryl, or heteroaryl and n is 0, 1 or 2.

The term "carboxyalkyl" refers to the groups —C(O)O-alkyl, —C(O)O-cycloalkyl, where alkyl and cycloalkyl, are as defined herein, and may be optionally further substituted by alkyl, alkenyl, alkynyl, alkoxy, halogen, $CF_3$, amino, substituted amino, cyano, or —S(O)$_n$R, in which R is alkyl, aryl, or heteroaryl and n is 0, 1 or 2.

The term "cycloalkyl" refers to cyclic alkyl groups of from 3 to 20 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and bicyclo[2.2.1]heptane, or cyclic alkyl groups to which is fused an aryl group, for example indan, and the like.

The term "substituted cycloalkyl" refers to cycloalkyl groups having from 1 to 5 substituents, and preferably 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, acyloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1-3 substituents chosen from alkyl, carboxy, carboxyalkyl, aminocarbonyl, hydroxy, alkoxy, halogen, $CF_3$, amino, substituted amino, cyano, and —S(O)$_n$R, where R is alkyl, aryl, or heteroaryl and n is 0, 1 or 2.

The term "halogen" or "halo" refers to fluoro, bromo, chloro, and iodo.

The term "acyl" denotes a group —C(O)R, in which R is hydrogen, optionally substituted alkyl, optionally substituted cycloalkyl, optionally substituted heterocyclyl, optionally substituted aryl, and optionally substituted heteroaryl.

The term "heteroaryl" refers to an aromatic group (i.e., unsaturated) comprising 1 to 15 carbon atoms and 1 to 4 heteroatoms selected from oxygen, nitrogen and sulfur within at least one ring.

Unless otherwise constrained by the definition for the heteroaryl substituent, such heteroaryl groups can be optionally substituted with 1 to 5 substituents, preferably 1 to 3 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1-3 substituents chosen from alkyl, carboxy, carboxyalkyl, aminocarbonyl, hydroxy, alkoxy, halogen, $CF_3$, amino, substituted amino, cyano, and —S(O)$_n$R, where R is alkyl, aryl, or heteroaryl and n is 0, 1 or 2. Such heteroaryl groups can have a single ring (e.g., pyridyl or furyl) or multiple condensed rings (e.g., indolizinyl, benzothiazole, or benzothienyl). Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, and the like as well as N-alkoxy-nitrogen containing heteroaryl compounds.

The term "heteroaryloxy" refers to the group heteroaryl-O—.

The term "heterocyclyl" refers to a monoradical saturated or partially unsaturated group having a single ring or multiple condensed rings, having from 1 to 40 carbon atoms and from 1 to 10 hetero atoms, preferably 1 to 4 heteroatoms, selected from nitrogen, sulfur, phosphorus, and/or oxygen within the ring.

The compounds of Formula I include the definition that "R and YR$^1$ when taken together with the nitrogen atom to which they are attached represents optionally substituted heterocyclyl". Such a definition includes heterocycles with only nitrogen in the ring, for example pyrrolidines and piperidines, and also includes heterocycles that have more than one heteroatom in the ring, for example piperazines, morpholines, and the like.

Unless otherwise constrained by the definition for the heterocyclic substituent, such heterocyclic groups can be optionally substituted with 1 to 5, and preferably 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1-3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2. Heterocyclic groups can have a single ring or multiple condensed rings. Preferred heterocyclics include tetrahydrofuranyl, morpholino, piperidinyl, and the like.

The term "thiol" refers to the group —SH.

The term "substituted alkylthio" refers to the group —S-substituted alkyl.

The term "heteroarylthiol" refers to the group —S-heteroaryl wherein the heteroaryl group is as defined above including optionally substituted heteroaryl groups as also defined above.

The term "sulfoxide" refers to a group —S(O)R, in which R is alkyl, aryl, or heteroaryl. "Substituted sulfoxide" refers to a group —S(O)R, in which R is substituted alkyl, substituted aryl, or substituted heteroaryl, as defined herein.

The term "sulfone" refers to a group —S(O)$_2$R, in which R is alkyl, aryl, or heteroaryl. "Substituted sulfone" refers to a group —S(O)$_2$R, in which R is substituted alkyl, substituted aryl, or substituted heteroaryl, as defined herein.

The term "keto" refers to a group —C(O)—. The term "thiocarbonyl" refers to a group —C(S)—. The term "carboxy" refers to a group —C(O)—OH.

"Optional" or "optionally" means that the subsequently described event or circumstance may or may not occur, and that the description includes instances where said event or circumstance occurs and instances in which it does not.

The term "compound of Formula I" is intended to encompass the compounds of the invention as disclosed, and the pharmaceutically acceptable salts, pharmaceutically acceptable solvates, such as, but not limited to, pharmaceutically acceptable hydrates, pharmaceutically acceptable esters, and prodrugs of such compounds. Additionally, the compounds of the invention may possess one or more asymmetric centers, and can be produced as a racemic mixture or as individual enantiomers or diastereoisomers. The number of stereoisomers present in any given compound of Formula I depends upon the number of asymmetric centers present (there are $2^n$ stereoisomers possible where n is the number of asymmetric centers). The individual stereoisomers may be obtained by resolving a racemic or non-racemic mixture of an intermediate at some appropriate stage of the synthesis, or by resolution of the compound of Formula I by conventional means. The individual stereoisomers (including individual enantiomers and diastereoisomers) as well as racemic and non-racemic mixtures of stereoisomers are encompassed within the scope of the present invention, all of which are intended to be depicted by the structures of this specification unless otherwise specifically indicated.

"Isomers" are different compounds that have the same molecular formula.

"Stereoisomers" are isomers that differ only in the way the atoms are arranged in space.

"Enantiomers" are a pair of stereoisomers that are non-superimposable mirror images of each other. A 1:1 mixture of a pair of enantiomers is a "racemic" mixture. The term "(±)" is used to designate a racemic mixture where appropriate.

"Diastereoisomers" are stereoisomers that have at least two asymmetric atoms, but which are not mirror-images of each other.

The absolute stereochemistry is specified according to the Cahn-Ingold-Prelog R-S system. When the compound is a pure enantiomer the stereochemistry at each chiral carbon may be specified by either R or S. Resolved compounds whose absolute configuration is unknown are designated (+) or (−) depending on the direction (dextro- or laevorotary) which they rotate the plane of polarized light at the wavelength of the sodium D line.

The term "therapeutically effective amount" refers to that amount of a compound of Formula I that is sufficient to effect treatment, as defined below, when administered to a mammal in need of such treatment. The therapeutically effective amount will vary depending upon the subject and disease condition being treated, the weight and age of the subject, the severity of the disease condition, the manner of administration and the like, which can readily be determined by one of ordinary skill in the art.

The term "treatment" or "treating" means any treatment of a disease in a mammal, including:
(i) preventing the disease, that is, causing the clinical symptoms of the disease not to develop;
(ii) inhibiting the disease, that is, arresting the development of clinical symptoms; and/or
(iii) relieving the disease, that is, causing the regression of clinical symptoms.

In many cases, the compounds of this invention are capable of forming acid and/or base salts by virtue of the presence of amino and/or carboxyl groups or groups similar thereto. The term "pharmaceutically acceptable salt" refers to salts that retain the biological effectiveness and properties of the compounds of Formula I, and which are not biologically or otherwise undesirable. Pharmaceutically acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl)amines, alkenyl amines, dialkenyl amines, trialkenyl amines, substituted alkenyl amines, di(substituted alkenyl)amines, tri(substituted alkenyl) amines, cycloalkyl amines, di(cycloalkyl)amines, tri(cycloalkyl)amines, substituted cycloalkyl amines, disubstituted cycloalkyl amine, trisubstituted cycloalkyl amines, cycloalkenyl amines, di(cycloalkenyl)amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, alkenyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group.

Specific examples of suitable amines include, by way of example only, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

A compound that is an agonist with high intrinsic efficacy evokes the maximal effect of which the biological system is capable. These compounds are known as "full agonists". They are able to elicit the maximum possible effect without occupying all the receptors, if the efficiency of coupling to the effector process is high. In contrast, "partial agonists" evoke a response but cannot evoke the maximal response of which the biological system is capable. They may have reasonable affinity but low intrinsic efficacy. Partial $A_1$ adenosine agonists may have an added benefit for chronic therapy because they will be less likely to induce desensitization of the $A_1$ receptor (R. B. Clark, B. J. Knoll, R. Barber TiPS, Vol. 20 (1999) p. 279-286), and less likely to cause side effects.

Nomenclature

The naming and numbering of the compounds of the invention is illustrated with a representative compound of Formula I in which R is hydrogen, $R^1$ is 2-hydroxycycloalkyl, $R^2$ is hydrogen, $R^3$ is 2-fluorophenyl, $R^4$ and $R^5$ are both hydrogen, and X and Y are both covalent bonds:

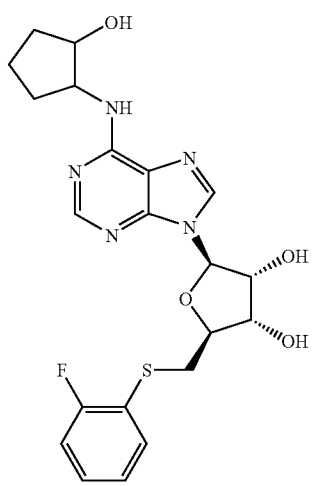

which is named:
2-{6-[((1R,2R)-2-hydroxycyclopentyl)amino]purin-9-yl}(4S,5S,2R,3R)-5-[(2-fluorophenylthio)methyl]oxolane-3,4-diol.

Synthetic Reaction Parameters

The terms "solvent", "inert organic solvent" or "inert solvent" mean a solvent inert under the conditions of the reaction being described in conjunction therewith [including, for example, benzene, toluene, acetonitrile, tetrahydrofuran ("THF"), dimethylformamide ("DMF"), chloroform, methylene chloride (or dichloromethane), diethyl ether, methanol, pyridine and the like]. Unless specified to the contrary, the solvents used in the reactions of the present invention are inert organic solvents.

The term "q.s." means adding a quantity sufficient to achieve a stated function, e.g., to bring a solution to the desired volume (i.e., 100%).

Synthesis of the Compounds of Formula I

The compounds of Formula I may be prepared starting from 2,6-dichloropurine, as shown in Reaction Scheme I.

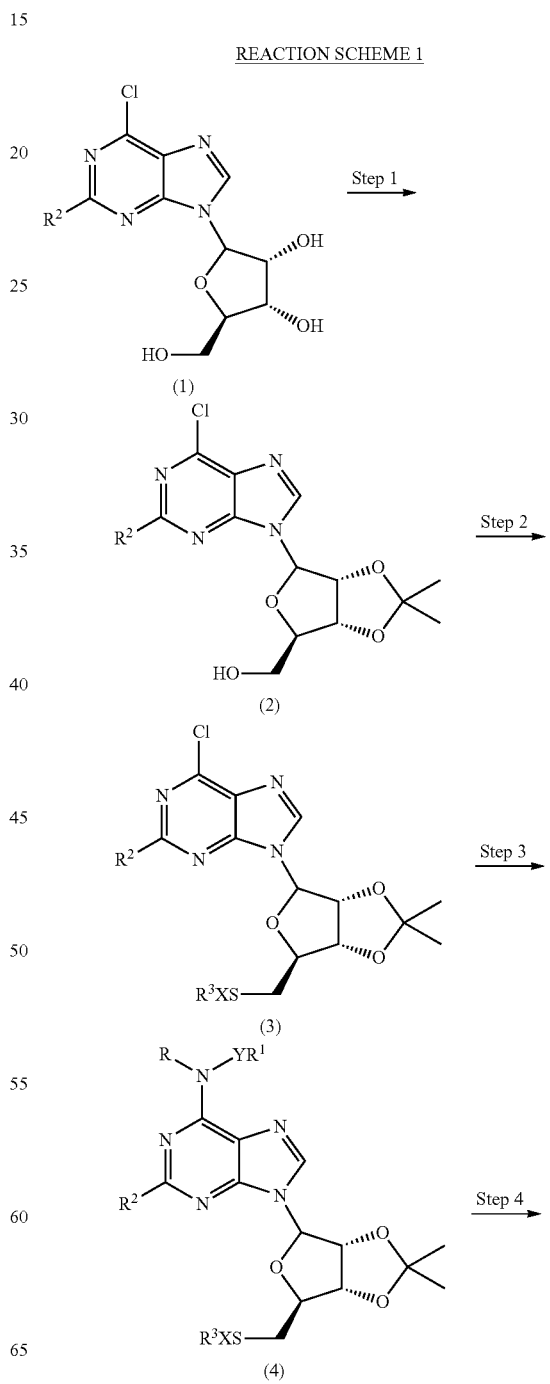

-continued

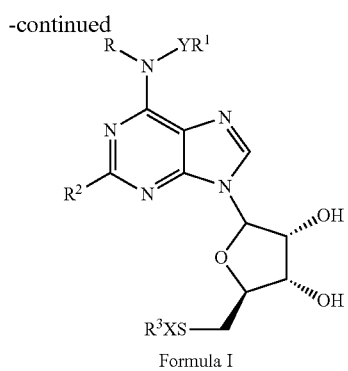

Formula I

Step 1—Preparation of Formula (2)

The starting compound of formula (1) is prepared as previously described in U.S. Pat. No. 5,789,416, the complete disclosure of which is incorporated by reference.

The compound of formula (2) is prepared conventionally from the compound of formula (1), by reaction with 2,2-dimethoxypropane in an inert solvent, preferably dimethylformamide, in the presence of a catalytic amount of an acid catalyst, preferably p-toluenesulfonic acid, at a temperature of about 40-90° C., preferably about 70° C., for about 24-72 hours, preferably about 48 hours. When the reaction is substantially complete, the product of formula (2) is isolated by conventional means, for example removal of the solvent under reduced pressure and purifying the residue by flash chromatography.

Step 2—Preparation of Formula (3)

The compound of formula (2) is then converted to a compound of formula (3). The compound of formula (2) is reacted with a thio compound of formula $R^3SH$, where $R^3$ is as defined above, in the presence of a triphenylphosphine and diethylazodicarboxylate, in an inert solvent, preferably an ether, more preferably tetrahydrofuran. The reaction is preferably conducted at reflux, for about 24-100 hours, preferably about 72 hours. When the reaction is substantially complete, the product of formula (3) is isolated by conventional means, for example removal of the solvent under reduced pressure and purifying the residue by flash chromatography.

Step 3—Preparation of Formula (4)

The 2-chloro moiety is then displaced from the compound of formula (3) by reaction with an amine of formula $RR^1YNH_2$, where Y is a covalent bond or alkylene, in the presence of a base, preferably triethylamine. The reaction is carried out in an inert protic solvent, preferably ethanol, at a temperature of about reflux, for about 14-48 hours, preferably about 24 hours. When the reaction is substantially complete, the product of formula (4) is isolated by conventional means, for example by removal of the solvent under reduced pressure, followed by chromatography of the residue on silica gel.

Step 4—Preparation of Formula I

The compound of formula (4) is then deprotected by treatment with an acid, preferably an organic acid, for example acetic acid. The reaction is carried out in a mixture of the acid and water, at about 50-100° C., preferably about 80-90° C., for about 10-48 hours, preferably about 16 hours. When the reaction is substantially complete, the product of Formula I is isolated by conventional means, for example by removal of the solvent under reduced pressure, followed by chromatography of the residue on silica gel.

It should be noted that steps 2 and 3 can be carried out in the reverse order.

Alternative Synthesis of the Compounds of Formula I

Alternatively, the compounds of Formula I may be prepared as shown in Reaction Scheme II.

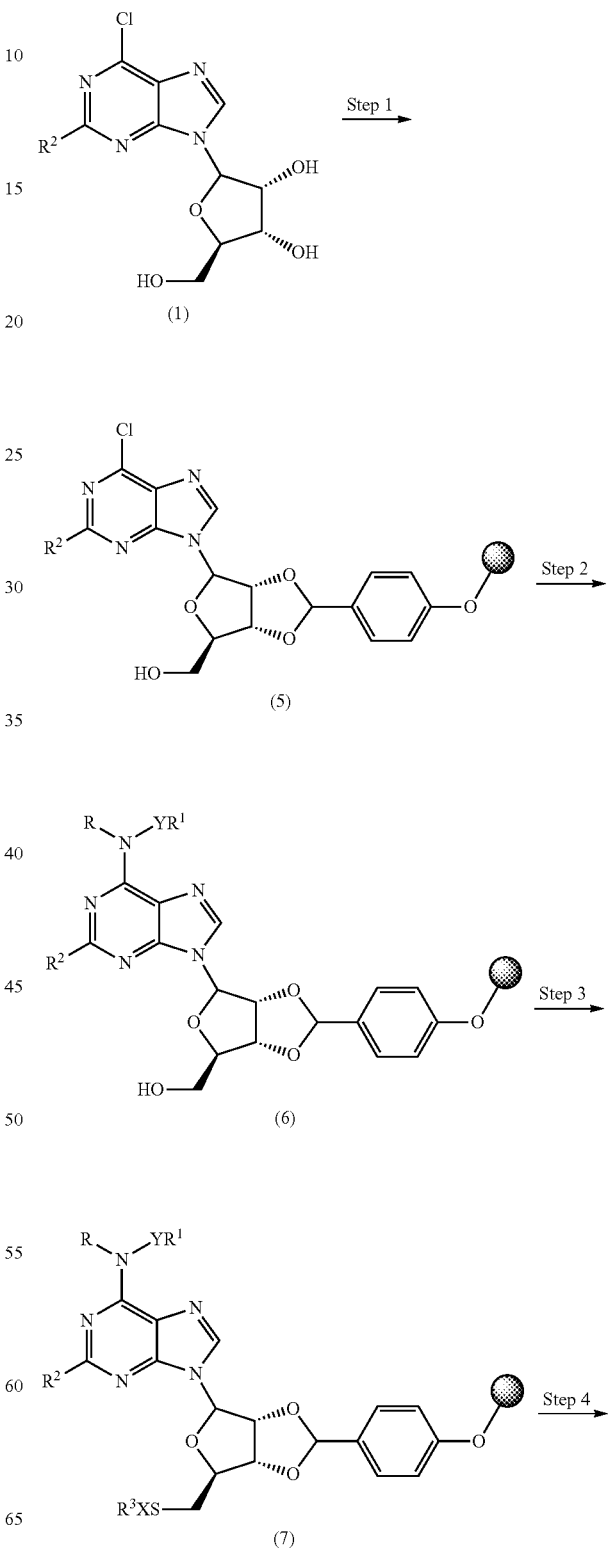

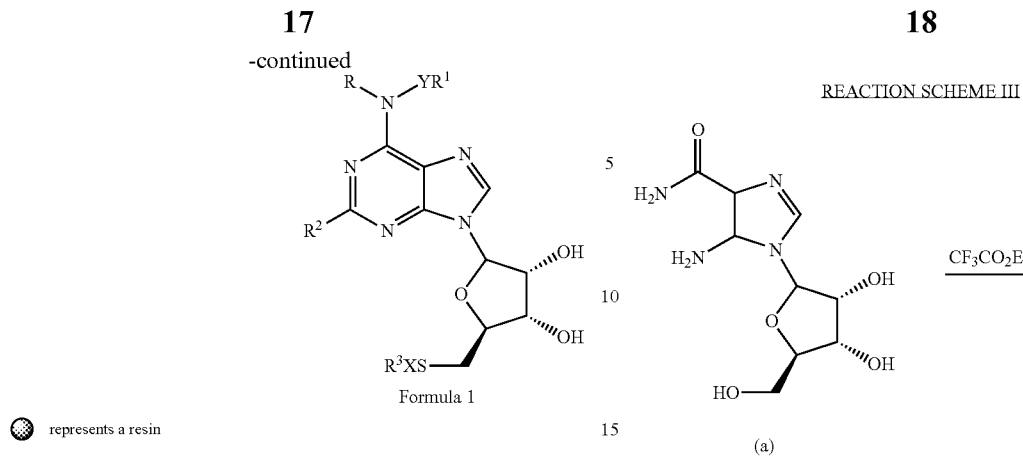

Formula 1

◉ represents a resin

Step 1—Preparation of Formula (5)
The resin/compound of formula (5) is prepared from the compound of formula (1), by reaction with dimethylacetal resin in an inert solvent, preferably dimethylacetamide, in the presence of a catalytic amount of an acid catalyst, preferably 10-camphorsulfonic acid, at about room temperature, for about 1-7 days, preferably about 4 days. When the reaction is substantially complete, the resin/product of formula (5) is isolated by conventional means, for example filtration.

Step 2—Preparation of Formula (6)
The 2-chloro moiety is then displaced from the resin/compound of formula (5) by reaction with an amine of formula $RR^1YNH_2$, where Y is a covalent bond or alkylene, in the presence of a base, preferably diisopropylethylamine. The reaction is carried out in an inert protic solvent, preferably 1,4-dioxane, at a temperature of about 80° C. for about 14-96 hours, preferably about 48 hours. When the reaction is substantially complete, the resin/product of formula (6) is isolated by conventional means.

Step 3—Preparation of Formula (7)
The product of formula (6) is then converted to a resin/compound of formula (7). The resin/compound of formula (6) is initially reacted with a compound capable of forming a leaving group, preferably methanesulfonyl chloride, in the presence of a base, preferably diisopropylethylamine, at about 0° C. The mesylated product is then reacted with a thio compound of formula $R^3XSH$, where $R^3$ and X are as defined above, in an inert solvent, preferably aqueous acetonitrile. The reaction is preferably conducted at about reflux, for about 24-100 hours, preferably about 70 hours. When the reaction is substantially complete, the product of formula (7) is isolated by conventional means, for example filtration.

Step 4—Preparation of Formula I
The resin/compound of formula (7) is then deprotected by treatment with an acid, preferably an organic acid, for example 2% trifluoroacetic acid/5% methanol/methylene chloride. The reaction is carried out at about room temperature for about 30 minutes to 10 hours, preferably about 2 hours. When the reaction is substantially complete, the product of Formula I is isolated by conventional means, for example extraction with an inert solvent, preferably methylene chloride, and removal of the solvent from the extract by evaporation under reduced pressure.

Starting Materials
Compounds of formula (1) in which $R^2$ is not hydrogen may be prepared by methods well known in the art. For example, the preparation of a compound of formula (1) in which $R^2$ is trifluoromethyl is prepared as shown in Reaction Scheme III.

REACTION SCHEME III

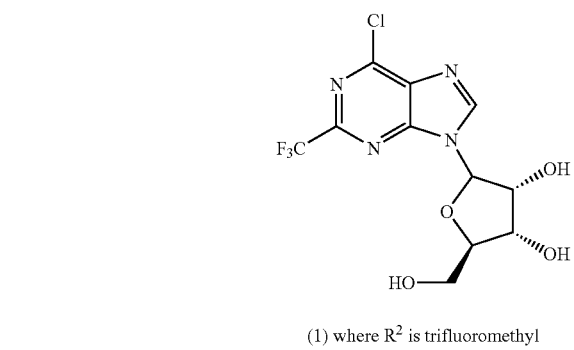

(a)

(1) where $R^2$ is trifluoromethyl

The preparation of a compound of formula (4) in which $R^2$ is nitrile is prepared as shown in Reaction Scheme IV.

REACTION SCHEME IV

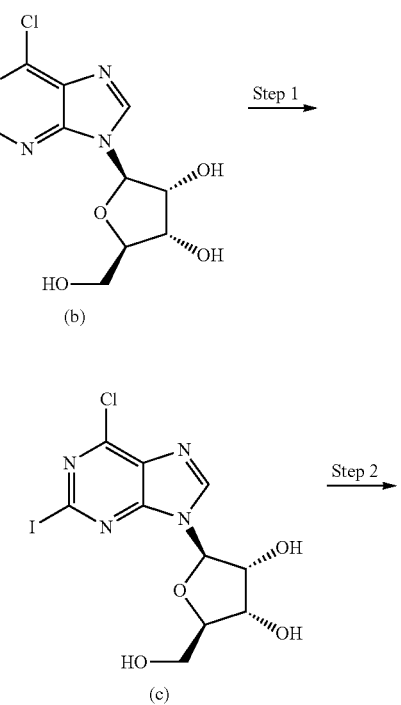

-continued

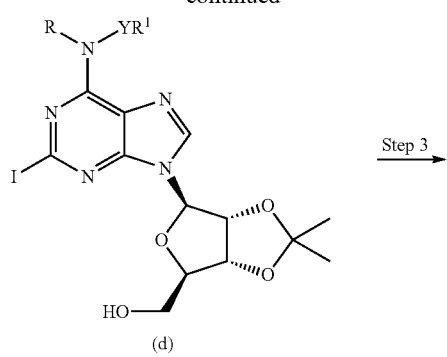

(d)

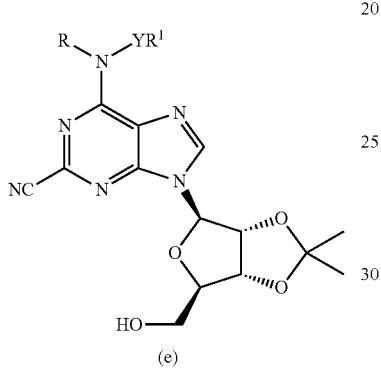

(e)

Starting Material of Formula (e)

The starting material of formula (b) is obtained commercially (Aldrich, Milwaukee). The product of formula (e) is converted into a compound of formula (4) as shown above.

The compounds of formula (1) where $R^2$ is acyl are obtained by reacting 2-stannyl-6-chloro-2',3',5'-tris-t-butyldimethylsilyladenosine (K. Kato et. al. J. Org. Chem. 1997, 62, 6833-6841) with an acid chloride.

The compounds of Formula I may also be prepared starting from 6-chloropurine riboside, as shown in Reaction Scheme V wherein $R^1$ is 2-hydroxycyclopentane, $R^2$ and R are hydrogen, and Y is a covalent bond:

REACTION SCHEME V

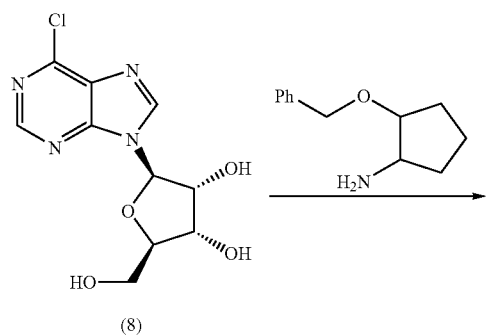

(8)

-continued

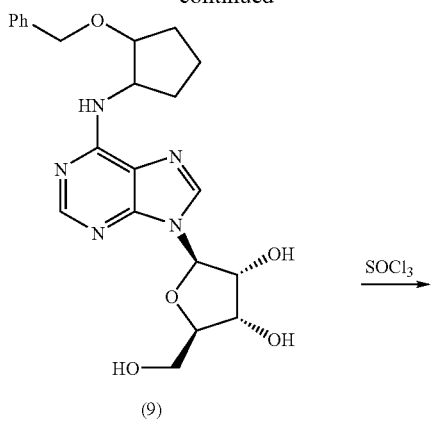

(9)

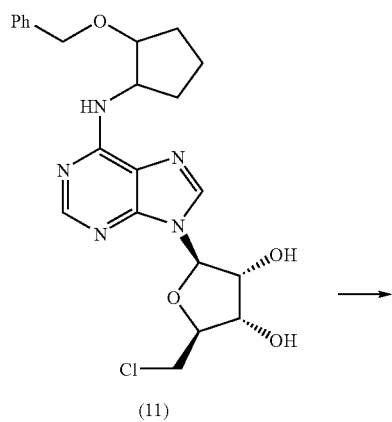

(10)

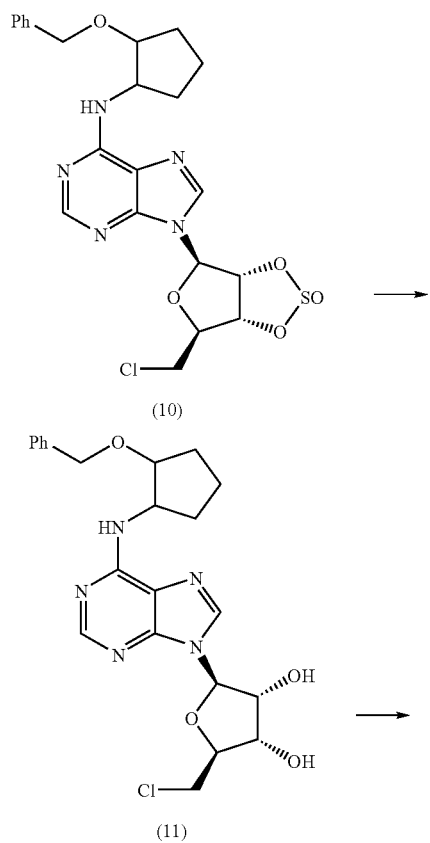

(11)

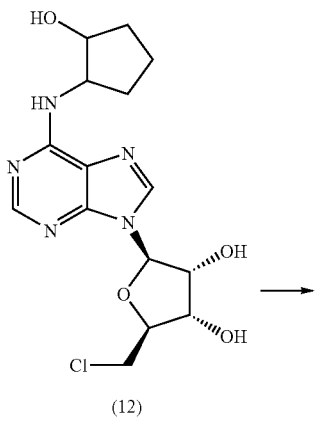

(12)

-continued

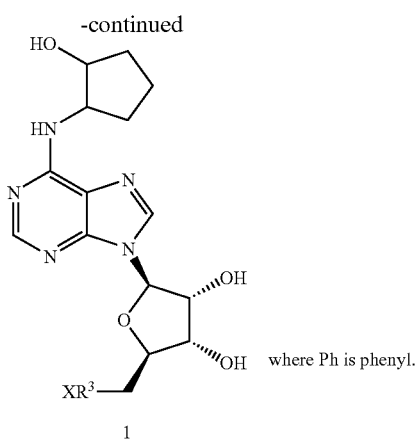

where Ph is phenyl.

1

Step 1—Preparation of Formula (9)

The compound of formula (9) is prepared from the compound of formula (8) by reaction with 2-(benzyloxy)cyclopentylamine in a protic solvent, such as ethanol, in the presence of a base, such as triethylamine, at a temperature of about reflux for about 24 hours. When the reaction is substantially complete, the product of formula (9) is isolated by conventional means, for example removal of the solvent under reduced pressure, partitioning the residue between ethyl acetate and water, removing the solvent from the organic layer, and purifying the residue by, for example, crystallization or precipitation from ethyl acetate/hexane.

Step 2—Preparation of Formula (10)

The compound of formula (9) is then converted to a compound of formula (10). To a suspension of the compound of formula (9) in an inert solvent, e.g., acetonitrile, is added thionyl chloride, in the presence of a base, preferably pyridine. The reaction is preferably conducted at about 0° C. for about 4 hours, and then allowed to warm to room temperature overnight. When the reaction is substantially complete, the resulting suspension is concentrated under reduced pressure to afford the compound of formula (10), which is taken to the next step without purification.

Step 3—Preparation of Formula (11)

The compound of formula (11) is prepared from the compound of formula (10) by dissolving (10) in a mixture of a base, e.g., ammonium hydroxide, and a protic solvent, e.g., methanol. The reaction is carried out at about room temperature, for about 30 minutes. When the reaction is substantially complete, the product of formula (11) is isolated by conventional means, for example by removal of the solvent under reduced pressure, partitioning the residue between ethyl acetate and water, and removing ethyl acetate under reduced pressure. The residue is used in the next step with no further purification.

Step 4—Preparation of Formula (12)

The compound of formula (11) is then deprotected by treatment with a partially unsaturated cycloalkyl compound, such as cyclohexene, in the presence of a catalyst, such as palladium hydroxide. Alternatively, ammonium formate can be used in place of the unsaturate cycloalkyl compound. The reaction is conducted in a protic solvent, e.g., ethanol, preferably at about reflux, for about 18 hours. When the reaction is substantially complete, the product of formula (12) is isolated by conventional means, for example by removal of the solvent under reduced pressure, followed by trituration of the residue.

Step 5—Preparation of Formula I

The compound of formula (12) is then reacted with a compound of formula $R^3SH$, preferably 2-fluorothiophenol. The reaction is conducted in a polar solvent, preferably N,N-dimethylformamide, in the presence of a base, e.g., sodium hydroxide, at a temperature of about 100° C. for about 3-5 hours. When the reaction is substantially complete, the product of Formula I is isolated by conventional means, for example by removal of the solvent under reduced pressure, and triturating the residue with diethyl ether.

Preparation of Starting Materials 2-(Benzyloxy)-cyclopentylamine is used as a starting material in step 1 of Reaction Scheme V. This compound, as the racemic mixture or as the individual isomers, is either commercially available or can be made by methods well known to those skilled in the art. For example, one method of making (1R,2R)-2-(benzyloxy)-cyclopentylamine is shown in Reaction Scheme VI below.

REACTION SCHEME VI

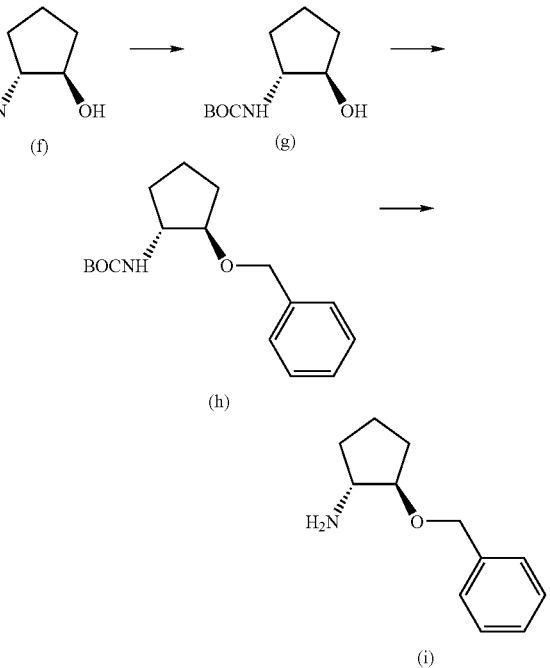

In the first step, the compound of formula (f) ((1R,2R)-2-aminocyclopentan-1-ol) is N-protected with $(BOC)_2O$ (di-t-butyl dicarbonate) by conventional means, for example by reaction in an inert solvent in the presence of 4-dimethylaminopyridine. The protected cyclopentanol (g) derivative is then reacted with benzyl bromide in the presence of a base, preferably sodium hydride, to form (h), which is then deprotected in a conventional manner, with hydrochloric acid in dioxane, for example.

Starting with (1S,2S)-2-aminocyclopentane-1-ol provides a compound with the opposite stereochemistry to formula (i), and starting with (1RS,2RS)-2-aminocyclopentane-1-ol provides a racemic analog of the compound of formula (i).

It will be appreciated by those of skill in the art that the addition of the $R^3SY$ moiety to the core structure may be carried out either before or after the removal of any protecting group on the $R^1$ moiety, such as the protecting group from the 2-hydroxy group on the 6N cyclopentyl group shown in Reaction Scheme V. An alternative process for the preparation of compounds of Formula I utilizing a different protecting group and reversing the addition of the $R^3SY$ moiety and deprotection of the $R^1$ group is shown in Reaction Scheme VII wherein $R^1$ is 2-hydroxycyclopentane, $R^2$ and R are hydrogen, and Y is a covalent bond.

REACTION SCHEME VII

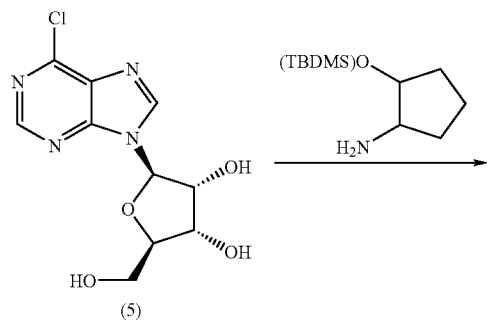

(5)

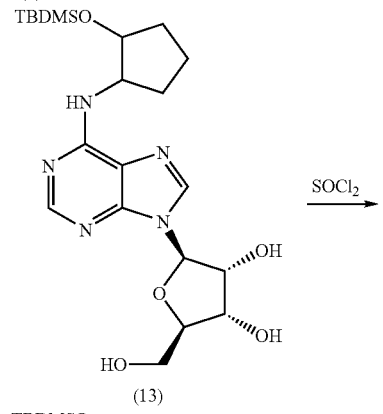

(13)

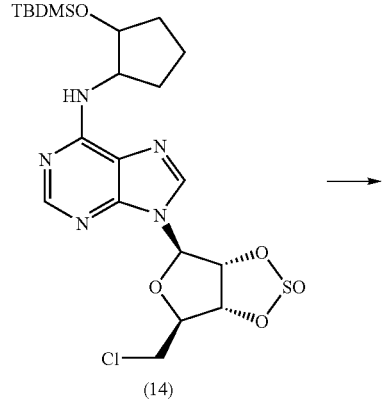

(14)

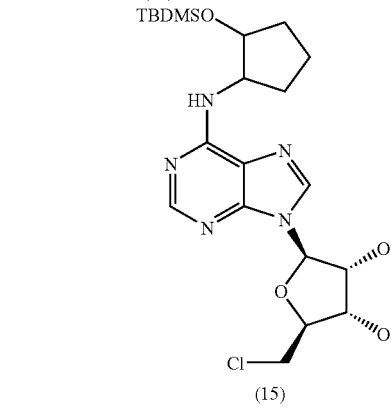

(15)

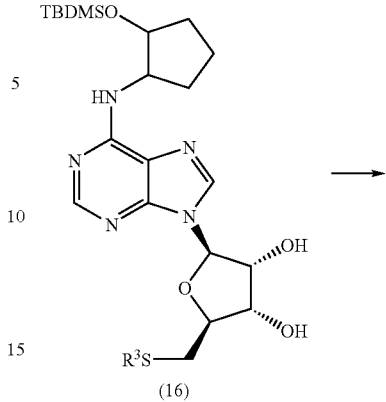

(16)

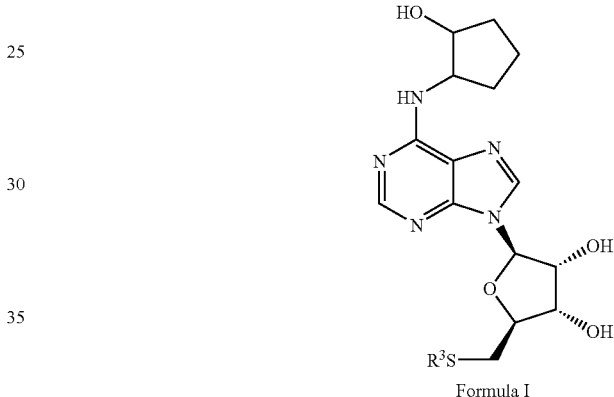

Formula I

The starting protected cyclopentyl derivative can be derived from (1R,2R)-2-aminocyclopentane-1-ol, (1S,2S)-2-aminocyclopentane-1-ol, or (1RS,2RS)-2-aminocyclopentane-1-ol. The hydroxy group is protected as a t-butyldimethylsilyl group by methods well known in the art, for example, by reaction with $NH_4F$ in methanol.

Alternatively, the compounds of Formula I can be conveniently synthesized without using any protecting groups, as shown in Reaction Scheme VIII wherein $R^1$ is 2-hydroxycyclopentane, $R^2$ and R are hydrogen, and Y is a covalent bond.

REACTION SCHEME VIII

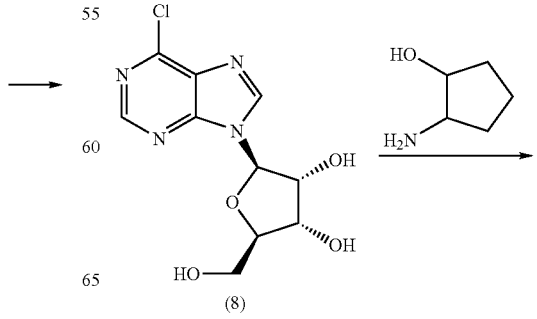

(8)

-continued
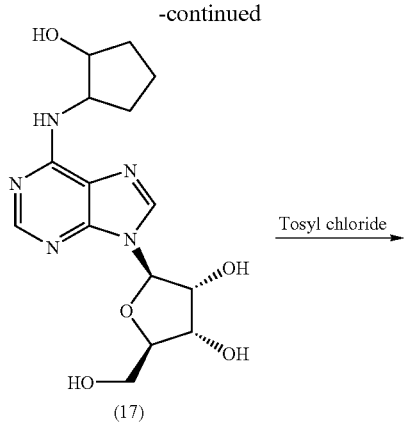
(17)
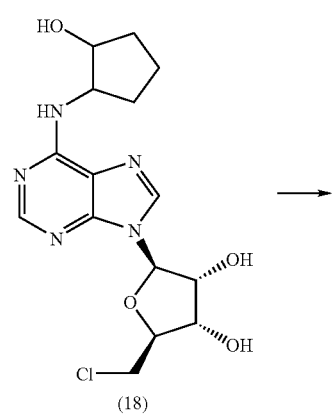
(18)
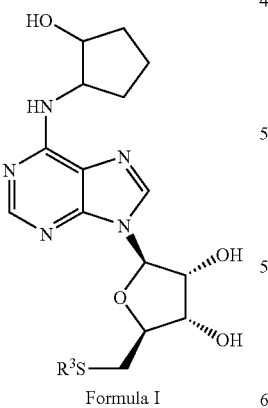
Formula I
REACTION SCHEME IV
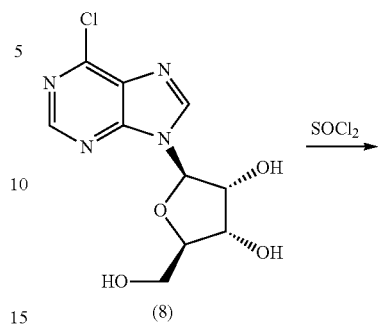
(8)
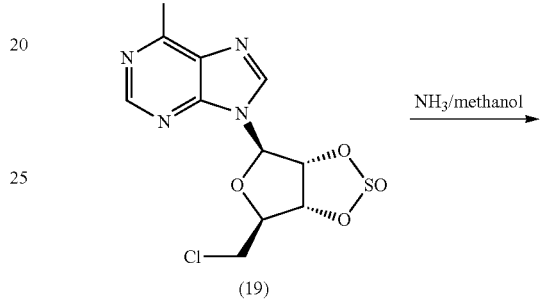
(19)
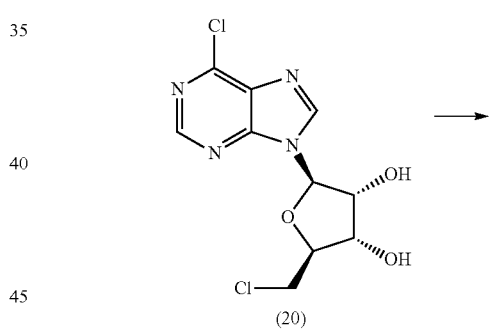
(20)
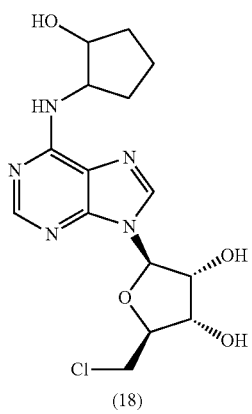
(18)
A preferred method of preparing the compounds of Formula I without the necessity of using any protecting groups, or of isolating and/or purifying the intermediates, is shown in Reaction Scheme IX wherein $R^1$ is 2-hydroxycyclopentane, $R^2$ and R are hydrogen, and Y is a covalent bond.

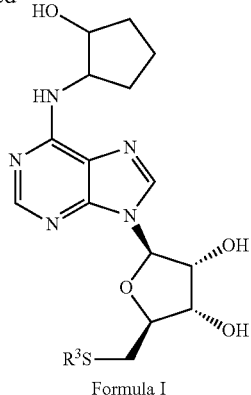

Formula I

Step 1—Preparation of Formula (19)

The compound of formula (8) is converted to a compound of formula (19) by reaction with thionyl chloride. In general, the compound of formula (8) is suspended in an inert solvent, preferably acetonitrile, in the presence of about 2-2.5 molar equivalents of a base, preferably pyridine, and about 5-5.5 molar equivalents of thionyl chloride slowly added over a period of about 1 hour. The reaction is preferably conducted at about 0° C. for about 3 hours, and then allowed to warm to room temperature overnight. When the reaction is substantially complete, the resulting suspension is concentrated under reduced pressure to afford the compound of formula (19), which is preferably taken to the next step without purification.

Step 3—Preparation of Formula (20)

The compound of formula (20) is prepared from the compound of formula (19) by dissolving the crude product of step 1 in a mixture of a protic solvent, preferably aqueous methanol, and a base, preferably aqueous ammonia. The reaction is carried out at about 0° C. for about 1 hour followed by about 3 hours at room temperature. When the reaction is substantially complete, the product of formula (20) is isolated by conventional means, and used in the next step with no further purification.

Step 4—Preparation of Formula (18)

The compound of formula (18) is prepared from the crude product of step 3 (the compound of formula (20) by reaction with about 1-1.1 molar equivalents of 2-hydroxycyclopentylamine in a protic solvent, preferably isopropanol, in the presence of about 3 molar equivalents of a base, preferably triethylamine, at a temperature of about reflux for about 24 hours. When the reaction is substantially complete, the product of formula (18) is isolated by conventional means, for example by removal of the solvent under reduced pressure and stirring the residue with water.

Step 5—Preparation of Formula I

The product of step 4 (the compound of formula (18) is then reacted with about 3-5 molar equivalents of a compound of formula $R^3SH$, for example 2-fluorothiophenol. The reaction is conducted in a polar solvent, typically N,N-dimethylformamide, in the presence of about 5-6 molar equivalents of a base, for example sodium hydride, sodium hydroxide, or triethylamine, preferably triethylamine, at about room temperature for about 1-5 days, preferably about 3 days. When the reaction is substantially complete, the product of Formula I is isolated by conventional means. The product can be additionally purified by recrystallization from various solvents, for example methanol, ethanol, isopropanol or mixtures of methanol and ethanol. Alternatively, the product can be purified by recrystallization from or slurrying with ethyl acetate.

Utility, Testing and Administration

General Utility

The compounds of Formula I are effective in the treatment of conditions known to respond to administration of a partial or full agonist of an $A_1$ adenosine receptor. Such conditions include, but are not limited to, acute and chronic disorders of heart rhythm, especially those diseases characterized by rapid heart rate, in which the rate is driven by abnormalities in the sinoatrial, atria, and AV nodal tissues. Such disorders include, but are not limited to, atrial fibrillation, supraventricular tachycardia and atrial flutter, congestive heart failure, non-insulin-dependent diabetes mellitus, decreased insulin sensitivity, Polycystic Ovarian Syndrome, Stein-Leventhal syndrome, hyperglycemia, epilepsy (anticonvulsant activity), and neuroprotection. $A_1$ agonists also have antilipolytic effects in adipocytes that leads to a decreased release of nonesterified fatty acids Testing Activity testing is conducted as described in those patents and literature citations referenced above, and in the Examples below, and by methods apparent to one skilled in the art.

Pharmaceutical Compositions

The compounds of Formula I are usually administered in the form of pharmaceutical compositions. This invention therefore provides pharmaceutical compositions that contain, as the active ingredient, one or more of the compounds of Formula I, or a pharmaceutically acceptable salt or ester thereof, and one or more pharmaceutically acceptable excipients, carriers, including inert solid diluents and fillers, diluents, including sterile aqueous solution and various organic solvents, permeation enhancers, solubilizers and adjuvants. The compounds of Formula I may be administered alone or in combination with other therapeutic agents. Such compositions are prepared in a manner well known in the pharmaceutical art (see, e.g., Remington's Pharmaceutical Sciences, Mace Publishing Co., Philadelphia, Pa. $17^{th}$ Ed. (1985) and "Modern Pharmaceutics", Marcel Dekker, Inc. $3^{rd}$ Ed. (G. S. Banker & C. T. Rhodes, Eds.).

Administration

The compounds of Formula I may be administered in either single or multiple doses by any of the accepted modes of administration of agents having similar utilities, for example as described in those patents and patent applications incorporated by reference, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

One mode for administration is parental, particularly by injection. The forms in which the novel compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. Aqueous solutions in saline are also conventionally used for injection, but less preferred in the context of the present invention. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating the compound of Formula I in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Oral administration is another route for administration of the compounds of Formula I. Administration may be via capsule or enteric coated tablets, or the like. In making the pharmaceutical compositions that include at least one compound of Formula I, the active ingredient is usually diluted by an excipient and/or enclosed within such a carrier that can be in the form of a capsule, sachet, paper or other container. When the excipient serves as a diluent, in can be a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents.

The compositions of the invention can be formulated so as to provide quick, sustained or delayed release of the active ingredient after administration to the patient by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

The compositions are preferably formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., a tablet, capsule, ampoule). The compounds of Formula I are effective over a wide dosage range and is generally administered in a pharmaceutically effective amount. Preferably, for oral administration, each dosage unit contains from 10 mg to 2 g of a compound of Formula I, more preferably from 10 to 700 mg, and for parenteral administration, preferably from 10 to 700 mg of a compound of Formula I, more preferably about 50-200 mg. It will be understood, however, that the amount of the compound of Formula I actually administered will be determined by a physician, in the light of the relevant circumstances, including the condition to be treated, the chosen route of administration, the actual compound administered and its relative activity, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules.

The tablets or pills of the present invention may be coated or otherwise compounded to provide a dosage form affording the advantage of prolonged action, or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices that deliver the formulation in an appropriate manner.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Preparation of a Compound of Formula (2)

A. Preparation of a Compound of Formula (2) in which $R^3$ is Hydrogen

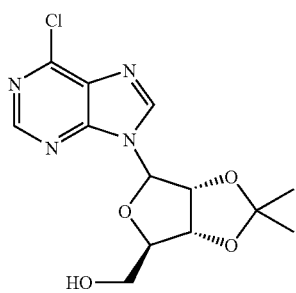

(2)

To a solution of 2-(6-chloropurin-9-yl)-5-hydroxymethyltetrahydrofuran-3,4-diol (a compound of formula (1)) (4.9 g, 17.1 mmol) and 2,2-dimethoxypropane (10.5 mL, 84.7 mmol) in dimethylformamide (100 mL) was added p-toluenesulfonic acid (325 mg, 1.71 mmol). After stirring for 24 hours at 70° C., the reaction was concentrated in vacuo and the residue purified by flash column chromatography (70% EtOAc/Hexanes) to give 6-(6-chloropurine-9-yl)-2,2-dimethyltetrahydrofuro[3,4-d][1,3]dioxol-4-yl]methanol, a compound of formula (2), as an off-white solid (2). (3.8 g, 68%) $^1$H NMR (CDCl$_3$) δ 1.4 (s, 3H), 1.65 (s, 3H), 3.8-4.0 (dd, 2H), 4.6 (s, 1H), 5.1-5.3 (m, 2H), 6.0 (d, 1H), 8.25 (s, 1H), 8.8 (s, 1H).

B. Preparation of a Compound of Formula (2), Varying $R^2$

Similarly, following the procedure of 1A above, but replacing 2-(6-chloropurin-9-yl)-5-hydroxymethyltetrahydrofuran-3,4-diol with other compounds of formula (1), other compounds of formula (2) are prepared.

Example 2

Preparation of a Compound of Formula (3)

A. Preparation of a Compound of Formula (3) in which $R^2$ is Hydrogen, $R^3$ is 2-Fluorophenyl, and X is a Covalent Bond

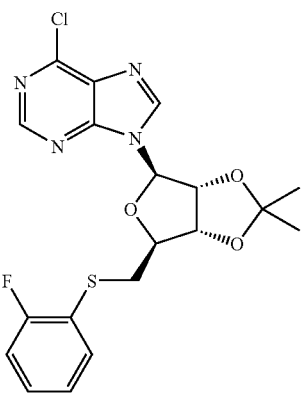

(3)

To a solution of 6-(6-chloropurine-9-yl)-2,2-dimethyltetrahydrofuro[3,4-d][1,3]dioxol-4-yl]methanol, a compound of formula (2) (0.48 g, 1.47 mmoles) in 20 mL of tetrahydrofuran was added triphenylphosphine (0.77 g, 2.94 mmoles) and diethylazodicarboxylate (0.47 mL, 2.94 mmoles), and the mixture stirred for 5 minutes. 2-Fluorothiophenol (0.31 mL, 2.94 mmoles) was then added, and the mixture was stirred under reflux. After 72 hours of reflux, the reaction was concentrated in vacuo and the residue purified by flash column chromatography (20% EtOAc/Hexanes) to give 1-{[(2S,1R,4R,5R)-4-(6-chloropurin-9-yl)-7,7-dimethyl-3,6,8-trioxabicyclo[3.3.0]oct-2-yl]methylthio}-2-fluorobenzene, a compound of formula (3), as a clear viscous oil (3). (0.25 g, ~40%)

$^1$H NMR (CDCl$_3$) δ 1.4 (s, 3H), 1.6 (s, 3H), 3.2 (m, 2H), 4.6 (t, 1H), 5.1 (m, 1H), 5.5 (m, 1H), 6.0 (d, 1H), 7.0 (m, 2H), 7.2 (m, 1H), 7.4 (m, 1H), 8.25 (s, 1H), 8.75 (s, 1H).

B. Preparation of a Compound of Formula (3), Varying $R^2$ and $R^3$

Similarly, following the procedure of 2A above, but optionally replacing 6-(6-chloropurine-9-yl)-2,2-dimethyltetrahydrofuro[3,4-d][1,3]dioxol-4-yl]methanol with other compounds of formula (2), and optionally replacing 2-fluorothiophenol with other compounds of formula $R^3$XH, the following compounds of formula (3) were prepared.

1-{[(2S,1R,4R,5R)-4-(6-chloropurin-9-yl)-7,7-dimethyl-3,6,8-trioxabicyclo[3.3.0]oct-2-yl]methylthio}benzene;
1-{[(2S,1R,4R,5R)-4-(6-chloropurin-9-yl)-7,7-dimethyl-3,6,8-trioxabicyclo[3.3.0]oct-2-yl]methylthio}-2,6-dichlorobenzene;
1-{[(2S,1R,4R,5R)-4-(6-chloropurin-9-yl)-7,7-dimethyl-3,6,8-trioxabicyclo[3.3.0]oct-2-yl]methylthio}-2,4-difluorobenzene;
1-{[(2S,1R,4R,5R)-4-(6-chloropurin-9-yl)-7,7-dimethyl-3,6,8-trioxabicyclo[3.3.0]oct-2-yl]methylthio}-4-fluorobenzene;
2-{[(2S,1R,4R,5R)-4-(6-chloropurin-9-yl)-7,7-dimethyl-3,6,8-trioxabicyclo[3.3.0]oct-2-yl]methylthio}-4-methyl-1,3-thiazole;
2-{[(2S,1R,4R,5R)-4-(6-chloropurin-9-yl)-7,7-dimethyl-3,6,8-trioxabicyclo[3.3.0]oct-2-yl]methylthio}-1,3-benzoxazole;
1-{[(2S,1R,4R,5R)-4-(6-chloropurin-9-yl)-7,7-dimethyl-3,6,8-trioxabicyclo[3.3.0]oct-2-yl]methylthio}-2-methylbenzene;
1-{[(2S,1R,4R,5R)-4-(6-chloropurin-9-yl)-7,7-dimethyl-3,6,8-trioxabicyclo[3.3.0]oct-2-yl]methylthio}-2-chlorobenzene;
1-{[(2S,1R,4R,5R)-4-(6-chloropurin-9-yl)-7,7-dimethyl-3,6,8-trioxabicyclo[3.3.0]oct-2-yl]methylthio}-4-chlorobenzene;
1-{[(2S,1R,4R,5R)-4-(6-chloropurin-9-yl)-7,7-dimethyl-3,6,8-trioxabicyclo[3.3.0]oct-2-yl]methylthio}-2-fluorobenzene;
1-{[(2S,1R,4R,5R)-4-(6-chloropurin-9-yl)-7,7-dimethyl-3,6,8-trioxabicyclo[3.3.0]oct-2-yl]methylthio}-3-fluorobenzene;
1-{[(2S,1R,4R,5R)-4-(6-chloropurin-9-yl)-7,7-dimethyl-3,6,8-trioxabicyclo[3.3.0]oct-2-yl]methylthio}-2-thiophene; and
1-{[(2S,1R,4R,5R)-4-(6-chloropurin-9-yl)-7,7-dimethyl-3,6,8-trioxabicyclo[3.3.0]oct-2-yl]methoxy}-2-fluorobenzene.

B. Preparation of a Compound of Formula (3), Varying $R^2$ and $R^3$

Similarly, following the procedure of 2A above, but optionally replacing 6-(6-chloropurine-9-yl)-2,2-dimethyltetrahydrofuro[3,4-d][1,3]dioxol-4-yl]methanol with other compounds of formula (2), and optionally replacing 2-fluorothiophenol with other compounds of formula R³XH, other compounds of formula (3) are prepared.

Example 3

Preparation of a Compound of Formula (4)

A. Preparation of Formula (4) in which R is Hydrogen, R¹ is Cyclopentyl, R² is Hydrogen, R³ is 2-Fluorophenyl, and X and Y are Covalent Bonds

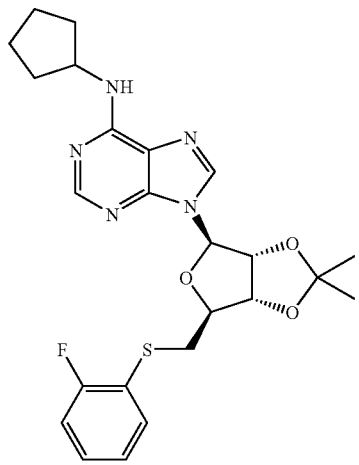

(4)

To a solution of 1-{[(2S,1R,4R,5R)-4-(6-chloropurin-9-yl)-7,7-dimethyl-3,6,8-trioxabicyclo[3.3.0]oct-2-yl]methylthio}-2-fluorobenzene, a compound of formula (3), (0.125 g, 2.86 mmoles) in 10 mL of ethanol and 1 mL of triethylamine was added cyclopentylamine in excess, and the mixture refluxed under nitrogen for 24 hours. The solvent was removed under reduced pressure, and the residue was purified by preparative TLC using 1:1 EtOAc:Hexanes to give (9-{(4S,1R,2R,5R)-4-[(2-fluorophenylthio)methyl]-7,7-dimethyl-3,6,8-trioxabicyclo[3.3.0]oct-2-yl}purin-6-yl)cyclopentylamine, a compound of formula (4), as a yellow oil (80 mg, 56%)

¹H NMR (CDCl₃) δ 1.4 (s, 3H), 1.6 (s, 3H), 1.6-2.4 (m, 6H), 3.15-3.25 (m, 2H), 4.1 (bs, 1H), 4.4 (t, 1H), 5.1 (m, 1H), 5.5 (m, 1H), 6.0 (d, 1H), 6.2 (bs, 1H), 7.0 (m, 2H), 7.2 (m, 1H), 7.4 (m, 1H), 7.8 (s, 1H), 8.25 (s, 1H).

B. Preparation of a Compound of Formula (4), Varying R¹, R², R³, and Y

Similarly, following the procedure of 3A above, but optionally replacing 1-{[(2S,1R,4R,5R)-4-(6-chloropurin-9-yl)-7,7-dimethyl-3,6,8-trioxabicyclo[3.3.0]oct-2-yl]methylthio}-2-fluorobenzene with other compounds of formula (3), and optionally replacing cyclopentylamine with other compounds of formula R¹YNH₂, the following compounds of formula (4) in which R is methyl, R¹ is 2-(3,4-dimethoxyphenyl)ethyl, R² is hydrogen, and X and Y are covalent bonds were also prepared:

R³ is 2,6-dichlorophenyl;
R³ is 4-methylthiazol-2-yl;
R³ is 1,3-benzoxazol-2-yl;
2-methylphenyl;
R³ is 2-chlorophenyl; and
R³ is 4-chlorophenyl.

C. Preparation of a Compound of Formula (4), Varying R¹, R², R³, and Y

Similarly, following the procedure of 3A above, but optionally replacing 1-{[(2S,1R,4R,5R)-4-(6-chloropurin-9-yl)-7,7-dimethyl-3,6,8-trioxabicyclo[3.3.0]oct-2-yl]methylthio}-2-fluorobenzene with other compounds of formula (3), and optionally replacing cyclopentylamine with other compounds of formula R¹YNH₂, other compounds of formula (4) are prepared.

Example 4

Preparation of a Compound of Formula I

A. Preparation of a Compound of Formula I in which R is Hydrogen, R¹ is Cyclopentyl, R² is Hydrogen, R³ is 2-Fluorophenyl, and X and Y are Covalent Bonds Formula I

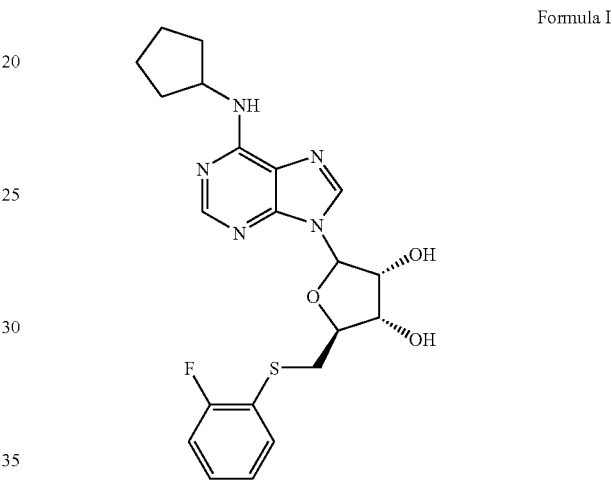

(9-{(4S,1R,2R,5R)-4-[(2-fluorophenylthio)methyl]-7,7-dimethyl-3,6,8-trioxabicyclo[3.3.0]oct-2-yl}purin-6-yl)cyclopentylamine, a compound of formula (4) (50 mg) was dissolved in a mixture of acetic acid (8 mL) and water (2 mL) and heated at 90 C for 16 hours. Solvents were removed under reduced pressure, and the residue was purified by preparative TLC [methanol-dichloromethane (1:9)] to afford (4S,5S,3R)-2-[6-(cyclopentylamino)purin-9-yl]-5-[(2-fluorophenylthio)methyl]oxolane-3,4-diol, a compound of Formula I.

¹H NMR (CDCl₃) δ 1.6-2.4 (m, 6H), 3.15-3.25 (m, 2H), 4.1 (bs, 1H), 4.4-4.65 (m, 4H), 6.0 (d, 1H), 6.8 (bs, 1H), 7.05 (m, 2H), 7.2 (m, 1H), 7.4 (m, 1H), 7.8 (s, 1H), 8.25 (s, 1H).

B. Preparation of a Compound of Formula I, Varying R¹

Similarly, following the procedure of 4A above, but replacing (9-{(4S,1R,2R,5R)-4-[(2-fluorophenylthio)methyl]-7,7-dimethyl-3,6,8-trioxabicyclo[3.3.0]oct-2-yl}purin-6-yl)cyclopentylamine with other compounds of formula (4), the following compounds of Formula I were made, in which R, R², R⁴ and R⁵ are hydrogen, R³ is 2-fluorophenyl, X and Y are covalent bonds, and R¹ is:

cyclopentyl;
(R,R)-2-hydroxycyclopentyl;
(R,S)-2-hydroxycyclopentyl;
bicyclo[2.2.1]heptan-2-yl,
7,7-dimethylbicyclo[2.2.1]heptan-2-yl;
bicyclo[2.2.1]heptan-2-yl-3-carboxylic acid ethyl ester;
bicyclo[2.2.1]heptan-2-yl-3-carboxylic acid
bicyclo[2.2.1]heptan-2-yl-3-methanol;
cyclopentyl-2-carboxylic acid ethyl ester;
cyclopentyl-2-carboxylic acid;

(R) 2-hydroxycyclohexyl;
(S) 2-hydroxycyclohexyl;
(R)-1-phenylethyl;
(S)-1-phenylethyl;
(4-fluorophenyl)methyl;
4-trifluoromethoxyphenylmethyl;
2,6-difluorophenylmethyl;
(3-methoxyphenyl)methyl;
(4-methoxyphenyl)methyl;
2-benzyloxycyclopentyl;
(4-methylphenyl)ethyl;
furan-2-yl;
phenylcyclopropyl;
3-propionic acid ethyl ester;
cyclohexyl;
1-(4-methoxyphenyl)ethyl;
3-trifluoromethylphenylmethyl;
3,5-dichlorophenylmethyl;
(3-fluorophenyl)methyl;
(2-trifluoromethylphenyl)methyl;
(4-chlorophenyl)methyl;
(2-fluorophenyl)methyl;
2-chloro-4-fluorophenylmethyl;
2-fluoro-4-trifluoromethylphenylmethyl;
2,4-dichlorophenylethyl;
(R)-2-phenylpropyl;
(S)-2-phenylpropyl;
2-(3-fluorophenyl)ethyl;
2-(2-chlorophenyl)ethyl;
6,6-dimethylbicyclo[3.3.1]kept-3-yl;
4-(tert-butyl)cyclohexyl;
2-chlorophenylmethyl;
1-(4-methylphenyl)ethyl;
(3-methylphenyl)methyl;
(4-methylphenyl)methyl;
2-trifluoromethyl-5-fluorophenylmethyl;
2-chloro-3-trifluoromethylphenylmethyl;
2,6,6-trimethylbicyclo[3.3.1]kept-3-yl;
1-naphthylmethyl;
bicyclo[3.1.1]heptyl-3-yl;
2-isopropyl-4-methylcyclohexyl;
2-carboxamidocyclohexyl;
(R)-2-carboxycyclohexyl;
(S)-2-carboxycyclohexyl;
2-hydroxymethylcyclohexyl;
2-carboxycyclohexyl ethyl ester;
2-carboxy-4-phenylcyclohexyl;
2-carboxybicyclo[2.2.1]hept-5-en-3-yl; and
2-carboxybicyclo[2.2.1]hept-3-yl ethyl ester.

Similarly, the following compounds of Formula I where R, $R^2$, $R^4$ and $R^5$ are hydrogen, and X and Y are covalent bonds were prepared:
  $R^3$ is 4-fluorophenyl and $R^1$ is cyclopentyl;
  $R^3$ is 2-methylphenyl and $R^1$ is cyclopentyl; and
  $R^3$ is 2,4-difluorophenyl and $R^1$ is cyclopentyl.

C. Preparation of a Compound of Formula I, Varying $R^1$, $R^2$ $R^3$, $R^4$, $R^5$, X and Y Similarly, following the procedure of 4A above, or using the combinatorial synthesis of Examples 5-8, but optionally replacing (9-{(4S,1R,2R,5R)-4-[(2-fluorophenylthio)methyl]-7,7-dimethyl-3,6,8-trioxabicyclo[3.3.0]oct-2-yl}purin-6-yl)cyclopentylamine with other compounds of formula (4), the following compounds of Formula I were made.

| $R^3$ | $R^1$ |
|---|---|
| 2,6 dichlorophenyl | 1-benzylpyrrolidin-3-yl |
| 2,6 dichlorophenyl | 1-benzylpiperidin-4-yl |
| 2,4 difluorophenyl | 1-benzylpyrrolidin-3-yl |
| 4-fluorophenyl | 1-benzylpiperidin-4-yl |
| 4-methyl-1,3-thiazole-2-yl | 1-benzylpyrrolidin-3-yl |
| 4-methyl-1,3-thiazole-2-yl | 1-benzylpiperidin-4-yl |
| 1,3-benzoxazol-2-yl | 1-benzylpyrrolidin-3-yl |
| 2-methylbenzyl | 1-benzylpyrrolidin-3-yl |
| 2-methylphenyl | 1-benzylpiperidin-4-yl |
| 2-chlorophenyl | 1-benzylpyrrolidin-3-yl |
| 2-chlorophenyl | 1-benzylpiperidin-4-yl |
| 2-fluorophenyl | 1-benzylpyrrolidin-3-yl |
| thiophen-2-yl | 1-benzylpyrrolidin-3-yl |
| 2,6 dichlorophenyl | ethyl |
| 2,6 dichlorophenyl | but-1-yl |
| 2,6 dichlorophenyl | isobut-1-yl |
| 2,6 dichlorophenyl | t-butyl |
| 2,6 dichlorophenyl | pent-3-yl |
| 2,6 dichlorophenyl | cyclobutyl |
| 2,6 dichlorophenyl | cyclopentyl |
| 2,6 dichlorophenyl | cyclohexyl |
| 2,6 dichlorophenyl | cycloheptyl |
| 2,6 dichlorophenyl | cyclooctyl |
| 2,6 dichlorophenyl | (R) bicyclo[2.2.1]heptan-2-yl |
| 2,6-dichlorophenyl | 3-(pyrrolid-2-one-1-yl)propyl |
| 2,6 dichlorophenyl | tetrahydrofuran-2-yl-methyl |
| 2,6 dichlorophenyl | benzyl |
| 2,6 dichlorophenyl | (2-methylphenyl)methyl |
| 2,6 dichlorophenyl | (4-methylphenyl)methyl |
| 2,6 dichlorophenyl | 1-phenylethyl |
| 2,6 dichlorophenyl | (2-methoxyphenyl)methyl |
| 2,6 dichlorophenyl | (4-methoxyphenyl)methyl |
| 2,6 dichlorophenyl | 1-cyclohexylethyl |
| 2,6 dichlorophenyl | 3-fluorobenzyl |
| 2,6-dichlorophenyl | 4-fluorobenzyl |
| 2,6 dichlorophenyl | (2-trifluoromethylphenyl)methyl |
| 2,6 dichlorophenyl | (2-fluoro-6-chlorophenyl)methyl |
| 2,6-dichlorophenyl | 2-(3-methoxyphenyl)ethyl |
| 2,6 dichlorophenyl | 2-(4-methoxyphenyl)ethyl |
| 2,6 dichlorophenyl | 2-(3-fluorophenyl)ethyl |
| 2,6 dichlorophenyl | 2-(4-fluorophenyl)ethyl |
| 2,6 dichlorophenyl | 2-(3-chlorophenyl)ethyl |
| 2,6 dichlorophenyl | 2,2-bis-phenylethyl |
| 2,6 dichlorophenyl | 2-(thiophen-2-yl)ethyl |
| 2,6-dichlorophenyl | 3-dimethylaminopropyl |
| 2,6 dichlorophenyl | 2-(morpholin-4-yl)ethyl |
| 2,6 dichlorophenyl | 2-[N-ethyl-N-(3-methylphenyl)amino]ethyl |
| 2,6-dichlorophenyl | pyridin-3-ylmethyl |
| 2,6-dichlorophenyl | 3-(imidazol-1-yl)propyl |
| 2,6-dichlorophenyl | 1,2-dimethylpropyl |
| 2,6 dichlorophenyl | (3,4-methylenedioxyphenyl)methyl |
| 2,6 dichlorophenyl | (R) bicyclo[2.2.1]heptan-2-yl |
| 2,6-dichlorophenyl | 4-methoxyphenyl |
| 2,4-dichlorophenyl | 4-ethoxyphenyl |
| 2,4-dichlorophenyl | 2-indanyl |
| 2,4-dichlorophenyl | 2-fluorophenyl |
| 2,4-difluorophenyl | ethyl |
| 2,4-difluorophenyl | but-1-yl |
| 2,4-difluorophenyl | 2-methylprop-1-yl |
| 2,4-difluorophenyl | pent-3-yl |
| 2,4-difluorophenyl | cyclopropylmethyl |
| 2,4-difluorophenyl | cyclobutyl |
| 2,4-difluorophenyl | cyclopentyl |
| 2,4-difluorophenyl | cyclohexyl |
| 2,4-difluorophenyl | cycloheptyl |
| 2,4-difluorophenyl | cyclooctyl |
| 2,4-difluorophenyl | (R) bicyclo[2.2.1]heptan-2-yl |
| 2,4-difluorophenyl | 2,6,6-trimethylbicyclo[3.1.1]hept-3-yl |
| 2,4-difluorophenyl | 2-(cyclohex-1-en-1-yl)ethyl |
| 2,4-difluorophenyl | 3-(2-oxopyrrolidin-1-yl)propyl |
| 2,4-difluorophenyl | tetrahydrofuran-2-yl-methyl |
| 2,4-difluorophenyl | 2-ethylhex-1-yl |
| 2,4-difluorophenyl | (2-methylphenyl)methyl |
| 2,4-difluorophenyl | 1-phenylethyl |
| 2,4-difluorophenyl | (2-methoxyphenyl)methyl |
| 2,4-difluorophenyl | (3-methoxyphenyl)methyl |
| 2,4-difluorophenyl | (4-methoxyphenyl)methyl |
| 2,4-difluorophenyl | (R)-1-cyclohexylethyl |

| | |
|---|---|
| 2,4-difluorophenyl | (S)-1-cyclohexylethyl |
| 2,4-difluorophenyl | (2-fluorophenyl)methyl |
| 2,4-difluorophenyl | (3-fluorophenyl)methyl |
| 2,4-difluorophenyl | (4-fluorophenyl)methyl |
| 2,4-difluorophenyl | (4-chlorophenyl)methyl |
| 2,4-difluorophenyl | 2-phenylethyl |
| 2,4-difluorophenyl | (2,4-dimethoxyphenyl)methyl |
| 2,4-difluorophenyl | 2-(3-fluorophenyl)ethyl |
| 2,4-difluorophenyl | 2-(4-fluorophenyl)ethyl |
| 2,4-difluorophenyl | 2-(3-chlorophenyl)ethyl |
| 2,4-difluorophenyl | 2-(2,2-bisphenyl)ethyl |
| 2,4-difluorophenyl | 3-phenylpropyl |
| 2,4-difluorophenyl | 2-(thiophen-2-yl)ethyl |
| 2,4-difluorophenyl | 3,3-bisphenylpropyl |
| 2,4-difluorophenyl | 2,2-dimethyl-3-(dimethylamino)propyl |
| 2,4-difluorophenyl | pyridin-2-yl-methyl |
| 2,4-difluorophenyl | pyridin-3-yl-methyl |
| 2,4-difluorophenyl | 3-(imidazol-1-yl)propyl |
| 2,4-difluorophenyl | (3,4-methylenedioxyphenyl)methyl |
| 2,4-difluorophenyl | (R) bicyclo[2.2.1]heptan-2-yl |
| 2,4-difluorophenyl | phenyl |
| 2,4-difluorophenyl | 4-methoxyphenyl |
| 2,4-difluorophenyl | 4-phenoxyphenyl |
| 2,4-difluorophenyl | 2-fluorophenyl |
| 2,4-difluorophenyl | 4-chlorophenyl |
| 4-fluorophenyl | but-1-yl |
| 4-fluorophenyl | sec butyl-1-yl |
| 4-fluorophenyl | t-butyl |
| 4-fluorophenyl | pent-3-yl |
| 4-fluorophenyl | cyclopropylmethyl |
| 4-fluorophenyl | cyclobutyl |
| 4-fluorophenyl | cyclopentyl |
| 4-fluorophenyl | cyclohexyl |
| 4-fluorophenyl | cycloheptyl |
| 4-fluorophenyl | cyclooctyl |
| 4-fluorophenyl | 3,3,5-trimethylcyclohexyl |
| 4-fluorophenyl | (R) bicyclo[2.2.1]heptan-2-yl |
| 4-fluorophenyl | 2,6,6-trimethylbicyclo[3.1.1]heptanyl |
| 4-fluorophenyl | 2-(cyclohex-1-en-1-yl)ethyl |
| 4-fluorophenyl | 2-ethylhex-3-yl |
| 4-fluorophenyl | phenyl |
| 4-fluorophenyl | (2-methylphenyl)methyl |
| 4-fluorophenyl | (3-methoxyphenyl)methyl |
| 4-fluorophenyl | 1-cyclohexylethyl |
| 4-fluorophenyl | (4-fluorophenyl)methyl |
| 4-fluorophenyl | (4-chlorophenyl)methyl |
| 4-fluorophenyl | (2-trifluoromethylphenyl)methyl |
| 4-fluorophenyl | 2-phenylethyl |
| 4-fluorophenyl | 2-(3-methoxyphenyl)ethyl |
| 4-fluorophenyl | 2-(4-methoxyphenyl)ethyl |
| 4-fluorophenyl | 2-(3-fluorophenyl)ethyl |
| 4-fluorophenyl | 2-(3-chlorophenyl)ethyl |
| 4-fluorophenyl | 3-phenylpropyl |
| 4-fluorophenyl | thiophen-2-ylmethyl |
| 4-fluorophenyl | 2,2-dimethyl-3-(dimethylamino)propyl |
| 4-fluorophenyl | 2-(morpholin-4-yl)ethyl- |
| 4-fluorophenyl | 2-[N-ethyl-N-(3-methylphenyl)]aminoethyl |
| 4-fluorophenyl | pyridin-2-yl-methyl |
| 4-fluorophenyl | pyridin-3-ylmethyl |
| 4-fluorophenyl | pyridin-4-yl-methyl |
| 4-fluorophenyl | 3-(imidazol-1-yl)propyl |
| 4-fluorophenyl | (3,4-methylenedioxyphenyl)methyl |
| 4-fluorophenyl | R) bicyclo[2.2.1]heptanyl |
| 4-fluorophenyl | phenyl |
| 4-fluorophenyl | 4-methoxyphenyl |
| 4-fluorophenyl | 4-ethoxyphenyl |
| 4-fluorophenyl | 4-phenoxyphenyl |
| 4-methyl-1,3-thiazole | ethyl |
| 4-methyl-1,3-thiazole | but-1-yl |
| 4-methyl-1,3-thiazole | sec but-1-yl |
| 4-methyl-1,3-thiazole | t-butyl |
| 4-methyl-1,3-thiazole | pent-3-yl |
| 4-methyl-1,3-thiazole | cyclopropylmethyl |
| 4-methyl-1,3-thiazole | cyclobutyl |
| 4-methyl-1,3-thiazole | cyclopentyl |
| 4-methyl-1,3-thiazole | cyclohexyl |
| 4-methyl-1,3-thiazole | cycloheptyl |
| 4-methyl-1,3-thiazole | 3,3,5 trimethylcyclohexyl |
| 4-methyl-1,3-thiazole | (R) bicyclo[2.2.1]heptan-2-yl |
| 4-methyl-1,3-thiazole | 2-(cyclohex-1-en-1-yl)ethyl |
| 4-methyl-1,3-thiazole | 3-(2-oxopyrrolidin-1-yl)propyl |
| 4-methyl-1,3-thiazole | phenyl |
| 4-methyl-1,3-thiazole | (2-methylphenyl)methyl |
| 4-methyl-1,3-thiazole | (3-methylphenyl)methyl |
| 4-methyl-1,3-thiazole | 1-phenylethyl |
| 4-methyl-1,3-thiazole | (3-methoxyphenyl)methyl |
| 4-methyl-1,3-thiazole | (4-methoxyphenyl)methyl |
| 4-methyl-1,3-thiazole | (2-fluorophenyl)methyl |
| 4-methyl-1,3-thiazole | (4-chlorophenyl)methyl |
| 4-methyl-1,3-thiazole | (2-trifluoromethylphenyl)methyl |
| 4-methyl-1,3-thiazole | (3,4-dichlorophenyl)methyl |
| 4-methyl-1,3-thiazole | 2-phenylethyl |
| 4-methyl-1,3-thiazole | 2-(3-methoxyphenyl)ethyl |
| 4-methyl-1,3-thiazole | (4-methoxyphenyl)methyl |
| 4-methyl-1,3-thiazole | 2-(3-fluorophenyl)ethyl |
| 4-methyl-1,3-thiazole | 2-(4-fluorophenyl)ethyl |
| 4-methyl-1,3-thiazole | 2-(2-chlorophenyl)ethyl |
| 4-methyl-1,3-thiazole | 2-(3-chlorophenyl)ethyl |
| 4-methyl-1,3-thiazole | 2,2-bisphenylethyl |
| 4-methyl-1,3-thiazole | 2-(thiophen-2-yl)ethyl |
| 4-methyl-1,3-thiazole | 3,3-bisphenylpropyl |
| 4-methyl-1,3-thiazole | 4-phenylbut-2-yl |
| 4-methyl-1,3-thiazole | 3-(dimethylamino)propyl |
| 4-methyl-1,3-thiazole | 2-(morphoiin-4-yl)ethyl- |
| 4-methyl-1,3-thiazole | 2-[2-ethyl-2-(3-methylphenyl)amino]ethyl |
| 4-methyl-1,3-thiazole | pyridin-3-ylmethyl |
| 4-methyl-1,3-thiazole | pyridin-4-ylmethyl |
| 4-methyl-1,3-thiazole | 3-(imidazol-1-yl)propyl |
| 4-methyl-1,3-thiazole | 3-methylbut-2-yl |
| 4-methyl-1,3-thiazole | (3,4-methylenedioxyphenyl)methyl |
| 4-methyl-1,3-thiazole | (S) bicyclo[2.2.1]heptan-2-yl |
| 4-methyl-1,3-thiazole | phenyl |
| 1,3-benzoxazol-2-yl | pent-3-yl |
| 1,3-benzoxazol-2-yl | cyclopropylmethyl |
| 1,3-benzoxazol-2-yl | cyclopentyl |
| 1,3-benzoxazol-2-yl | cycloheptyl |
| 1,3-benzoxazol-2-yl | cyclooctyl |
| 1,3-benzoxazol-2-yl | 3,3,5-trimethylcyclohexyl |
| 1,3-benzoxazol-2-yl | 3-(2-oxopyrrolidin-1-yl)propyl |
| 1,3-benzoxazol-2-yl | tetrahydrofuran-2-yl-methyl |
| 1,3-benzoxazol-2-yl | 2-ethylhex-1-yl |
| 1,3-benzoxazol-2-yl | phenyl |
| 1,3-benzoxazol-2-yl | (2-methylphenyl)methyl |
| 1,3-benzoxazol-2-yl | (4-methylphenyl)methyl |
| 1,3-benzoxazol-2-yl | 1-phenylethyl |
| 1,3-benzoxazol-2-yl | (2-methoxyphenyl)methyl |
| 1,3-benzoxazol-2-yl | (3-methoxyphenyl)methyl |
| 1,3-benzoxazol-2-yl | (4-methoxyphenyl)methyl |
| 1,3-benzoxazol-2-yl | 1-cyclohexylethyl |
| 1,3-benzoxazol-2-yl | (3-fluorophenyl)methyl |
| 1,3-benzoxazol-2-yl | (4-fluorophenyl)methyl |
| 1,3-benzoxazol-2-yl | (2-fluoro-6-chlorophenyl)methyl |
| 1,3-benzoxazol-2-yl | (2,4-dichlorophenyl)methyl |
| 1,3-benzoxazol-2-yl | 2-phenylethyl |
| 1,3-benzoxazol-2-yl | 2-(3-methoxyphenyl)ethyl |
| 1,3-benzoxazol-2-yl | 2-(4-methoxyhenyl)ethyl |
| 1,3-benzoxazol-2-yl | 2-(4-fluorophenyl)ethyl |
| 1,3-benzoxazol-2-yl | 2-(2-chlorophenyl)ethyl |
| 1,3-benzoxazol-2-yl | 2-(3-chlorophenyl)ethyl |
| 1,3-benzoxazol-2-yl | 2,2-bis-phenylethyl |
| 1,3-benzoxazol-2-yl | 3-phenylpropyl |
| 1,3-benzoxazol-2-yl | 2-(thiophen-2-yl)ethyl |
| 1,3-benzoxazol-2-yl | 3,3-bisphenylpropyl |
| 1,3-benzoxazol-2-yl | 2-(morpholin-4-yl)ethyl- |
| 1,3-benzoxazol-2-yl | 2-[N-ethyl-N-(3-methylphenyl)amino]ethyl |
| 1,3-benzoxazol-2-yl | 3-methylbut-2-yl |
| 1,3-benzoxazol-2-yl | (S) bicyclo[2.2.1]heptan-2-yl |
| 1,3-benzoxazol-2-yl | phenyl |
| 1,3-benzoxazol-2-yl | 4-ethoxyphenyl |
| 1,3-benzoxazol-2-yl | 2-indanyl |
| 2-methylphenyl | ethyl |
| 2-methylphenyl | but-1-yl |
| 2-methylphenyl | sec-but-1-yl |
| 2-methylphenyl | pent-3-yl |
| 2-methylphenyl | cyclopropylmethyl |
| 2-methylphenyl | cyclopentyl |
| 2-methylphenyl | cycloheptyl |
| 2-methylphenyl | 3,3,5-trimethylcyclohexyl |
| 2-methylphenyl | (S) bicyclo[2.2.1]heptan-2-yl |
| 2-methylphenyl | 2,6,6-trimethylbicyclo[3.1.1]hept-3-yl |

| | |
|---|---|
| 2-methylphenyl | 2-(cyclohex-1-en-1-yl)ethyl |
| 2-methylphenyl | 3-(pyrrolid-2-one-1-yl)propyl |
| 2-methylphenyl | 2-ethylhex-1-yl |
| 2-methylphenyl | (2-methylphenyl)methyl |
| 2-methylphenyl | (3-methylphenyl)methyl |
| 2-methylphenyl | 1-phenylethyl |
| 2-methylphenyl | (4-methoxyphenyl)methyl |
| 2-methylphenyl | (R)-1-cyclohexylethyl |
| 2-methylphenyl | (2-trifluoromethylphenyl)methyl |
| 2-methylphenyl | (3,4-dichlorophenyl)methyl |
| 2-methylphenyl | 2-(3-fluorophenyl)ethyl |
| 2-methylphenyl | 2-(4-fluorophenyl)ethyl |
| 2-methylphenyl | 2-(2-chlorophenyl)ethyl |
| 2-methylphenyl | 2-(3-chlorophenyl)ethyl |
| 2-methylphenyl | 3-phenylpropyl |
| 2-methylphenyl | 2,2-bisphenylethyl |
| 2-methylphenyl | 3-dimethylaminopropyl |
| 2-methylphenyl | 2-(morpholin-4-yl)ethyl- |
| 2-methylphenyl | 2-[N-ethyl-N-(3-methylphenyl)amino]ethyl |
| 2-methylphenyl | pyridin-2-yl-methyl |
| 2-methylphenyl | pyridin-3-yl-methyl |
| 2-methylphenyl | pyridin-4-yl-methyl |
| 2-methylphenyl | 3-propylimidazol-1-yl |
| 2-methylphenyl | 3,4-methylenedioxyphenylmethyl |
| 2-methylphenyl | (R) bicyclo[2.2.1]heptan-2-yl |
| 2-methylphenyl | 4-methoxyphenyl |
| 2-methylphenyl | 4-phenoxyphenyl |
| 2-methylphenyl | 2-indanyl |
| 2-chlorophenyl | ethyl |
| 2-chlorophenyl | but-1-yl |
| 2-chlorophenyl | pent-3-yl |
| 2-chlorophenyl | cyclopropylmethyl |
| 2-chlorophenyl | cyclopentyl |
| 2-chlorophenyl | cyclohexyl |
| 2-chlorophenyl | cycloheptyl |
| 2-chlorophenyl | 3,3,5 trimethylhexyl |
| 2-chlorophenyl | 2-(cyclohex-1-en-1-yl)ethyl |
| 2-chlorophenyl | 3-(pyrrolid-2-one-1-yl)propyl |
| 2-chlorophenyl | tetrahydrofuran-2-ylmethyl |
| 2-chlorophenyl | 2-ethylhex-1-yl |
| 2-chlorophenyl | 2-(4-methoxypheny)ethyl |
| 2-chlorophenyl | 2-(3-fluorophenyl)ethyl |
| 2-chlorophenyl | 2-(4-fluorophenyl)ethyl |
| 2-chlorophenyl | 2-(2-chlorophenyl)ethyl |
| 2-chlorophenyl | 2-(3-chlorophenyl)ethyl |
| 2-chlorophenyl | 2,2 bisphenylethyl |
| 2-chlorophenyl | 3-phenylpropyl |
| 2-chlorophenyl | 2-(thiophen-2-yl)ethyl |
| 2-chlorophenyl | 3,3-bisphenylpropyl |
| 2-chlorophenyl | 4-phenylbut-2-yl |
| 2-chlorophenyl | 3-dimethylaminopropyl |
| 2-chlorophenyl | 2-(morpholin-4-yl)ethyl- |
| 2-chlorophenyl | 2-[N-ethyl-N-(3-methylphenyl)amino]ethyl |
| 2-chlorophenyl | pyridin-2-yl-methyl |
| 2-chlorophenyl | pyridin-4-yl-methyl |
| 2-chlorophenyl | 3-(imidazol-3-yl)propyls |
| 2-chlorophenyl | 1,2-dimethylpropyl |
| 2-chlorophenyl | pentyl-3-yl |
| 2-chlorophenyl | 3,4-methylenedioxyphenylmethyl |
| 2-chlorophenyl | (S) bicyclo[2.2.1]heptan-2-yl |
| 2-chlorophenyl | 4-methoxyphenyl |
| 2-chlorophenyl | 4-ethoxyphenyl |
| 2-chlorophenyl | 4-phenoxyphenyl |
| 2-chlorophenyl | 2-indanyl |
| 2-chlorophenyl | 4-chlorophenyl |
| 2-chlorophenyl | tetrahydropyran-4-yl |
| 2-chlorophenyl | phenylmethyl |
| 2-chlorophenyl | (2-methylphenyl)methyl |
| 2-chlorophenyl | (3-methylphenyl)methyl |
| 2-chlorophenyl | 1-phenylethyl |
| 2-chlorophenyl | (2-methoxyphenyl)methyl |
| 2-chlorophenyl | (3-methoxyphenyl)methyl |
| 2-chlorophenyl | (4-methoxyphenyl)methyl |
| 2-chlorophenyl | 1-(cyclohexyl)ethyl |
| 2-chlorophenyl | (3-fluorophenyl)methyl |
| 2-chlorophenyl | (3-chlorophenyl)methyl |
| 2-chlorophenyl | (2-trifluoromethylphenyl)methyl |
| 2-chlorophenyl | (2-fluoro-6-chlorophenyl)methyl |
| 2-chlorophenyl | 2-phenylethyl |
| 2-chlorophenyl | 2-(3-methoxyphenyl)ethyl |
| 2-chlorophenyl | ethyl |
| 4-chlorophenyl | isobut-1-yl |
| 4-chlorophenyl | t-butyl |
| 4-chlorophenyl | pent-3-yl |
| 4-chlorophenyl | cyclopropylmethyl |
| 4-chlorophenyl | cyclopentyl |
| 4-chlorophenyl | cyclohexyl |
| 4-chlorophenyl | cycloheptyl |
| 4-chlorophenyl | 3,3,5 trimethylcyclohexyl |
| 4-chlorophenyl | (S) bicyclo[2.2.1]heptan-2-yl |
| 4-chlorophenyl | 2,6,6-trimethylbicyclo[3.1.1]hept-3-yl |
| 4-chlorophenyl | cyclohexylethyl |
| 4-chlorophenyl | tetrahydrofuran-2-yl-methyl |
| 4-chlorophenyl | 2-ethylhex-1-yl |
| 4-chlorophenyl | phenylmethyl |
| 4-chlorophenyl | (2-methylphenyl)methyl |
| 4-chlorophenyl | (3-methylphenyl)methyl |
| 4-chlorophenyl | (4-methylphenyl)methyl |
| 4-chlorophenyl | 2-phenylethyl |
| 4-chlorophenyl | (2-methoxyphenyl)methyl |
| 4-chlorophenyl | (3-methoxyphenyl)methyl |
| 4-chlorophenyl | (4-methoxyphenyl)methyl |
| 4-chlorophenyl | (R)-1-cyclohexlethyl |
| 4-chlorophenyl | (S)-1-cyclohexylethyl |
| 4-chlorophenyl | (2-fluorophenyl)methyl |
| 4-chlorophenyl | (3-fluorophenyl)methyl |
| 4-chlorophenyl | (4-chlorophenyl)methyl |
| 4-chlorophenyl | (2-fluoro-6-chlorophenyl)methyl |
| 4-chlorophenyl | (2,4-dichlorophenyl)methyl |
| 4-chlorophenyl | 2-phenylethyl |
| 4-chlorophenyl | 2-(3-methoxyphenyl)ethyl |
| 4-chlorophenyl | 2-(3-fluorophenyl)ethyl |
| 4-chlorophenyl | 2-(4-fluorophenyl)ethyl |
| 4-chlorophenyl | 2-(2-chlorophenyl)ethyl |
| 4-chlorophenyl | 2-(3-chlorophenyl)ethyl |
| 4-chlorophenyl | 2,2-bis-phenylethyl |
| 4-chlorophenyl | 3-phenylpropyl |
| 4-chlorophenyl | 2-(thiophene-2-yl)ethyl |
| 4-chlorophenyl | 3,3 bisphenylpropyl |
| 4-chlorophenyl | 4-phenylbut-2-yl |
| 4-chlorophenyl | N-ethyl-N-(3-methylphenyl)ethylamino |
| 4-chlorophenyl | phenyl |
| 4-chlorophenyl | 4-methoxyphenyl |
| 4-chlorophenyl | 4-ethoxyphenyl |
| 4-chlorophenyl | 4-phenoxyphenyl |
| 4-chlorophenyl | ethyl |
| 2-fluorophenyl | but-1-yl |
| 2-fluorophenyl | isobut-1-yl |
| 2-fluorophenyl | t-butyl |
| 2-fluorophenyl | pent-3-yl |
| 2-fluorophenyl | cyclopropylmethyl |
| 2-fluorophenyl | cyclobutyl |
| 2-fluorophenyl | cyclopentyl |
| 2-fluorophenyl | cyclohexyl |
| 2-fluorophenyl | cycloheptyl |
| 2-fluorophenyl | (S) bicyclo[2.2.1]heptan-2-yl |
| 2-fluorophenyl | 2,6,6-trimethylbicyclo[3.1.1]hept-3-yl |
| 2-fluorophenyl | 2-(cyclohex-1-en-1-yl)ethyl 1 |
| 2-fluorophenyl | 3-(pyrrolid-2-one-1-yl)propyl |
| 2-fluorophenyl | tetrahydrofuran-2-yl-methyl |
| 2-fluorophenyl | 2-ethylhex-1-yl |
| 2-fluorophenyl | benzyl |
| 2-fluorophenyl | (2-methylphenyl)methyl |
| 2-fluorophenyl | (3-methylphenyl)methyl |
| 2-fluorophenyl | (4-methylphenyl)methyl |
| 2-fluorophenyl | 1-phenylethyl |
| 2-fluorophenyl | (2-methoxyphenyl)methyl |
| 2-fluorophenyl | (3-methoxyphenyl)methyl |
| 2-fluorophenyl | (4-methoxyphenyl)methyl |
| 2-fluorophenyl | (R)-1-(cyclohexyl)ethyl |
| 2-fluorophenyl | (S)-1-(cyclohexyl)ethyl |
| 2-fluorophenyl | (2-fluorophenyl)methyl |
| 2-fluorophenyl | (3-fluorophenyl)methyl |
| 2-fluorophenyl | (4-fluorophenyl)methyl |
| 2-fluorophenyl | (4-chlorophenyl)methyl |
| 2-fluorophenyl | (2-trifluoromethylphenyl)methyl |
| 2-fluorophenyl | (2-fluoro-6-chlorophenyl)methyl |
| 2-fluorophenyl | 2-phenylethyl |
| 2-fluorophenyl | 2-(3-methoxyphenyl)ethyl |
| 2-fluorophenyl | 2-(4-methoxyphenyl)ethyl |

| | |
|---|---|
| 2-fluorophenyl | 2-(3-fluorophenyl)ethyl |
| 2-fluorophenyl | 2-(4-fluorophenyl)ethyl |
| 2-fluorophenyl | 2-(3-chlorophenyl)ethyl |
| 2-fluorophenyl | 2,2 bisphenylmethyl |
| 2-fluorophenyl | 3-phenylpropyl |
| 2-fluorophenyl | 2-(thiophen-2-yl)ethyl |
| 2-fluorophenyl | (S)-(3,3 bisphenyl)propyl |
| 2-fluorophenyl | 4-phenylbut-2-yl |
| 2-fluorophenyl | 2-[N-ethyl-N-(3-methylphenyl)amino]ethyl |
| 2-fluorophenyl | pyridin-2-ylmethyl |
| 2-fluorophenyl | (3,4-methylenedioxyphenyl)methyl |
| 2-fluorophenyl | (S) bicyclo[2.2.1]heptan-2-yl |
| 2-fluorophenyl | phenyl |
| 2-fluorophenyl | 4-methoxyphenyl |
| 2-fluorophenyl | 4-ethoxyphenyl |
| 2-fluorophenyl | 4-phenoxyphenyl |
| 2-fluorophenyl | 2-indanyl |
| 2-fluorophenyl | 4-chlorophenyl |
| 2-fluorophenyl | but-1-yl |
| 3-fluorophenyl | isobut-1-yl |
| 3-fluorophenyl | t-butyl |
| 3-fluorophenyl | pent-3-yl |
| 3-fluorophenyl | cyclopropylmethyl |
| 3-fluorophenyl | cyclobutyl |
| 3-fluorophenyl | cyclopentyl |
| 3-fluorophenyl | cyclohexyl |
| 3-fluorophenyl | cyclohept-3-yl |
| 3-fluorophenyl | cyclooctyl |
| 3-fluorophenyl | 3,3,5-trimethylcyclohexyl |
| 3-fluorophenyl | 2-ethylhex-1-yl |
| 3-fluorophenyl | benzyl |
| 3-fluorophenyl | (2-methylphenyl)methyl |
| 3-fluorophenyl | (3-methylphenyl)methyl |
| 3-fluorophenyl | (4-methylphenyl)methyl |
| 3-fluorophenyl | 1-phenylethyl |
| 3-fluorophenyl | (4-methoxyphenyl)methyl |
| 3-fluorophenyl | (2-fluorophenyl)methyl |
| 3-fluorophenyl | (3-fluorophenyl)methyl |
| 3-fluorophenyl | (2,4-dichlorophenyl)methyl |
| 3-fluorophenyl | (3,4-dichlorophenyl)methyl |
| 3-fluorophenyl | 2-(3-methoxyphenyl)ethyl |
| 3-fluorophenyl | 2-(4-methoxyhenyl)ethyl |
| 3-fluorophenyl | 2-(3-fluorophenyl)ethyl |
| 3-fluorophenyl | 2-(4-fluorophenyl)ethyl |
| 3-fluorophenyl | 2-(3-chlorophenyl)ethyl |
| 3-fluorophenyl | 2,2-bisphenylethyl |
| 3-fluorophenyl | 3-phenylpropyl |
| 3-fluorophenyl | 3,3-bisphenylpropyl |
| 3-fluorophenyl | 4-phenylbut-2-yl |
| 3-fluorophenyl | 2-(morpholin-4-yl)ethyl- |
| 3-fluorophenyl | 2-(N-ethyl-N-phenyl)aminoethyl |
| 3-fluorophenyl | pyridin-2-ylmethyl |
| 3-fluorophenyl | pyridin-2-ylmethyl |
| 3-fluorophenyl | 1,2-dimethylpropyl |
| 3-fluorophenyl | (3,4-methylenedioxyphenyl)methyl |
| 3-fluorophenyl | (R) bicyclo[2.2.1]heptan-2-yl |
| 3-fluorophenyl | phenyl |
| 3-fluorophenyl | 4-methoxyphenyl |
| 3-fluorophenyl | 4-ethoxyphenyl |
| 3-fluorophenyl | 4-phenoxyphenyl |
| thiophene-2-yl | t-butyl |
| thiophene-2-yl | pent-3-yl |
| thiophene-2-yl | cyclopropylmethyl |
| thiophene-2-yl | 3,3,5-trimethylcyclohexane |
| thiophene-2-yl | (S) bicyclo[2.2.1]heptan-2-yl |
| thiophene-2-yl | tetrahydrofuran-2-ylmethyl |
| thiophene-2-yl | 2-ethylhex-1-yl |
| thiophene-2-yl | benzyl |
| thiophene-2-yl | (2-methylphenyl)methyl |
| thiophene-2-yl | (3-methylphenyl)methyl |
| thiophene-2-yl | (4-methylphenyl)methyl |
| thiophene-2-yl | (2-methoxyphenyl)methyl |
| thiophene-2-yl | (3-methoxyphenyl)methyl |
| thiophene-2-yl | (4-methoxyphenyl)methyl |
| thiophene-2-yl | 1-cyclohexylethyl |
| thiophene-2-yl | (2-fluorophenyl)methyl |
| thiophene-2-yl | (3-fluorophenyl)methyl |
| thiophene-2-yl | (4-fluorophenyl)methyl |
| thiophene-2-yl | 2-phenylethyl |
| thiophene-2-yl | 2-(4-methoxyphenyl)ethyl |
| thiophene-2-yl | 2-(3-fluorophenyl)ethyl |
| thiophene-2-yl | 2-[N-ethyl-N-(3-methylphenyl)amino]ethyl |
| thiophene-2-yl | phenyl |
| 3-fluorophenyl | ethyl |
| phenyl | but-1-yl |
| phenyl | isobut-1-yl |
| phenyl | t-butyl |
| phenyl | pentyl-3-yl |
| phenyl | cyclopropylmethyl |
| phenyl | cyclobutyl-1-yl |
| phenyl | cyclopentyl |
| phenyl | cyclohexyl |
| phenyl | cyclohept-3-yl |
| phenyl | 3,3,5-trimethylcyclohexyl |
| phenyl | (R) bicyclo[2.2.1]heptan-2-yl |
| phenyl | 2,6,6-trimethylbicyclo[3.1.1]hept-3-yl |
| phenyl | 2-(cyclohex-1-en-1-yl)ethyl |
| phenyl | 3-(2-oxopyrrolidin-1-yl)propyl |
| phenyl | tetrahydrofuran-2-ylmethyl |
| phenyl | 2-ethylhex-1-yl |
| phenyl | phenyl |
| phenyl | (2-methylphenyl)methyl |
| phenyl | (3-methylphenyl)methyl |
| phenyl | (4-methylphenyl)methyl |
| phenyl | 1-phenylethyl |
| phenyl | (4-methoxyphenyl)methyl |
| phenyl | (R)-1-cyclohexylethyl |
| phenyl | (S)-1-cyclohexylethyl |
| phenyl | (2-fluorophenyl)methyl |
| phenyl | (3-fluorophenyl)methyl |
| phenyl | (4-fluorophenyl)methyl |
| phenyl | (4-chlorophenyl)methyl |
| phenyl | (2-trifluoromethylphenyl)methyl |
| phenyl | (2-fluoro-6-chlorophenyl)methyl |
| phenyl | (2,4-dichlorophenyl)methyl |
| phenyl | (3,4-dichlorophenyl)methyl |
| phenyl | 2-phenylethyl |
| phenyl | 2-(3-methoxyphenyl)ethyl |
| phenyl | 2-(3-fluorophenyl)ethyl |
| phenyl | 2-(4-fluorophenyl)ethyl |
| phenyl | 2-(3-chlorophenyl)ethyl |
| phenyl | 2,2-bisphenylethyl |
| phenyl | phenylcyclopropyl |
| phenyl | 3-phenylpropyl |
| phenyl | 2-(thiophen-2-yl)ethyl |
| phenyl | 3-dimethylaminopropyl |
| phenyl | 2-(morpholin-4-yl)ethyl |
| phenyl | 1-benzylpiperidin-4-yl |
| phenyl | pyridin-2-yl-methyl |
| phenyl | pyridin-4-yl-methyl |
| phenyl | 3-(imidazol-1-yl)propyl |
| phenyl | (3,4-methylenedioxyphenyl)methyl |
| phenyl | phenyl |
| phenyl | 4-methoxyphenyl |
| phenyl | 4-ethoxyphenyl |
| phenyl | 4-phenoxyphenyl |
| phenyl | 2-indanyl |

| $R^3$ | COMBINATION OF R, $R^1$ AND THE NITROGEN ATOM TO WHICH THEY ARE ATTACHED |
|---|---|
| 2,4-dichlorophenyl | piperidin-1-yl |
| 2,4-dichlorophenyl | 2-ethypiperidin-1-yl |
| 2,4-dichlorophenyl | 4-(piperidin-1-yl)piperidin-1-yl |
| 2,4-dichlorophenyl | 1,2,3,4-tetrahydro-isoquinolin-2-yl |
| 2,4-dichlorophenyl | morpholin-4-yl |
| 2,4-difluorophenyl | 4-methylpiperazin-1-yl |
| 2,4-difluorophenyl | pyrrolidin-1-yl |
| 2,4-difluorophenyl | 4-benzylpiperazin-1-yl |
| 2,4-difluorophenyl | piperidin-1-yl |
| 2,4-difluorophenyl | 4-(piperidin-1-yl)piperidin-1-yl |
| 2,4-difluorophenyl | 1,2,3,4-tetrahydro-isoquinolin-2-yl |
| 2,4-difluorophenyl | morpholin-4-yl |
| 2,4-difluorophenyl | 4-methylpiperazin-1-yl |
| 4-fluorophenyl | 4-benzylpiperazin-1-yl |
| 4-fluorophenyl | piperidin-1-yl |
| 4-fluorophenyl | 2-ethylpiperidin-1-yl |
| 4-fluorophenyl | 4-benzylpiperidin-1-yl |
| 4-fluorophenyl | 4-(piperidin-1-yl)piperidin-1-yl |

-continued

| | |
|---|---|
| 4-fluorophenyl | 1,2,3,4-tetrahydro-isoquinolin-2-yl |
| 4-fluorophenyl | morpholin-4-yl |
| 4-fluorophenyl | 4-phenlypiperazin-1-yl |
| 4-methyl-1,3-thiazol-2-yl | pyrrolidin-1-yl |
| 4-methyl-1,3-thiazol-2-yl | 4-benzylpiperazin-1-yl |
| 4-methyl-1,3-thiazol-2-yl | piperidin-1-yl |
| 4-methyl-1,3-thiazol-2-yl | 4-benzylpiperidin-1-yl |
| 4-methyl-1,3-thiazol-2-yl | 4-(piperidin-1-yl)piperidin-1-yl |
| 4-methyl-1,3-thiazol-2-yl | 1,2,3,4-tetrahydro-isoquinolin-2-yl |
| 4-methyl-1,3-thiazol-2-yl | morpholin-4-yl |
| 4-methyl-1,3-thiazol-2-yl | 4-methylpiperazino-1-yl |
| 4-methyl-1,3-thiazol-2-yl | 4-phenylpiperazin-1-yl |
| 1,3-benzoxazol-2-yl | pyrrolidin-1-yl |
| 1,3-benzoxazol-2-yl | 2-ethylpiperidin-1-yl |
| 1,3-benzoxazol-2-yl | 4-benzylpiperidin-1-yl |
| 1,3-benzoxazol-2-yl | morpholin-4-yl |
| 1,3-benzoxazol-2-yl | 4-methylpiperazin-1-yl |
| 2-methylphenyl | pyrrolidin-1-yl |
| 2-methylphenyl | piperidin-1-yl |
| 2-methylphenyl | 2-ethylpiperidin-1-yl |
| 2-methylphenyl | 4-benzylpiperidin-1-yl |
| 2-methylphenyl | 4-(piperidin-1-yl)piperidin-1-yl |
| 2-methylphenyl | 1,2,3,4-tetrahydro-isoquinolin-2-yl |
| 2-methylphenyl | morpholin-4-yl |
| 2-methylphenyl | 4-(3,4-dichlorophenyl)piperazin-1-yl |
| 2-methylphenyl | 4-methylpiperazin-1-yl |
| 2-methylphenyl | 4-phenylpiperazin-1-yl |
| 2-methylphenyl | pyrrolidin-1-yl |
| 2-chlorophenyl | 4-benzylpiperazin-1-yl |
| 2-chlorophenyl | piperidin-1-yl |
| 2-chlorophenyl | 2-ethylpiperidin-1-yl |
| 2-chlorophenyl | 4-benzylpiperidine-1-yl |
| 2-chlorophenyl | 4-(piperidin-1-yl)piperidin-1-yl |
| 2-chlorophenyl | 1,2,3,4-tetrahydro-isoquinolin-2-yl |
| 2-chlorophenyl | morpholin-4-yl |
| 2-chlorophenyl | 4-(3,4-dichlorophenyl)piperazin-1-yl |
| 2-chlorophenyl | 4-methylpiperazin-1-yl |
| 2-chlorophenyl | 4-phenylpiperazin-1-yl |
| 4-chlorophenyl | pyrrolidin-1-yl |
| 4-chlorophenyl | 4-benzylpiperazin-1-yl |
| 4-chlorophenyl | piperidin-1-yl |
| 4-chlorophenyl | 2-ethylpiperidin-1-yl |
| 4-chlorophenyl | 4-(piperidin-1-yl)piperidin-1-yl |
| 4-chlorophenyl | 1,2,3,4,-tetrahydro-isoquinolin-2-yl |
| 4-chlorophenyl | morpholin-4-yl |
| 4-chlorophenyl | 4-phenylpiperazin-1-yl |
| 2-fluorophenyl | pyrrolidin-1-yl |
| 2-fluorophenyl | 4-benzylpiperazin-1-yl |
| 2-fluorophenyl | piperidin-1-yl |
| 2-fluorophenyl | 2-ethylpiperidin-1-yl |
| 2-fluorophenyl | morpholin-4-yl |
| 2-fluorophenyl | 4-phenylpiperazin-1-yl |
| 2-fluorophenyl | pyrrolidin-1-yl |
| 2-fluorophenyl | 4-benzylpiperazin-1-yl |
| 3-fluorophenyl | piperidin-1-yl |
| 3-fluorophenyl | 4-benzylpiperidin-1-yl |
| 3-fluorophenyl | 1,2,3,4-tetrahydro-isoquinolin-2-yl |
| 3-fluorophenyl | morpholin-4-yl |
| 3-fluorophenyl | 4-methylpiperazin-1-yl |
| 3-fluorophenyl | 4-(piperidin-1-yl)piperidin-1-yl |
| thiophen-2-yl | 4-phenylpiperazin-1-yl |
| thiophen-2-yl | 2-ethylpiperidin-1-yl |
| phenyl | pyrrolidin-1-yl |
| phenyl | 4-benzylpiperazin-1-yl |
| phenyl | piperidin-1-yl |
| phenyl | 2-ethylpiperidin-1-yl |
| phenyl | 4-benzylpiperidin-1-yl |
| phenyl | 4-phenylpiperazin-1-yl |
| phenyl | 4-(piperidin-1-yl)piperidin-1-yl |
| phenyl | morpholin-4-yl |
| phenyl | 4-(3,4-dichlorophenyl)piperazin-1-yl |

The following compounds of Formula I in which R is methyl, $R^1$ is 2-(3,4-dimethoxyphenyl)ethyl, $R^2$ is hydrogen, and X and Y are covalent bonds were also prepared:

$R^3$ is 2,6-dichlorophenyl;
$R^3$ is 4-methylthiazol-2-yl;
$R^3$ is 1,3-benzoxazol-2-yl;
2-methylphenyl;
$R^3$ is 2-chlorophenyl; and
$R^3$ is 4-chlorophenyl.

D. Preparation of a Compound of Formula I, Varying $R^1$, $R^2$, $R^3$, $R^4$, $R^5$, X and Y Similarly, following the procedure of 4A above, but optionally replacing (9-{(4S,1R,2R,5R)-4-[(2-fluorophenylthio) methyl]-7,7-dimethyl-3,6,8-trioxabicyclo[3.3.0]oct-2-yl}purin-6-yl)cyclopentylamine with other compounds of formula (4), other compounds of Formula I are made.

Compounds of Formula I were alternatively made in a combinatorial fashion, as shown in Reaction Scheme II above. Examples 5-8 detail the preparation of a single compound using this technology, but the process was utilized to provide parallel syntheses of multiple compounds of Formula I in a combinatorial manner.

Example 5

Preparation of a Compound of Formula (5)

A. Preparation of a Compound of Formula (5) in which $R^2$ is Hydrogen

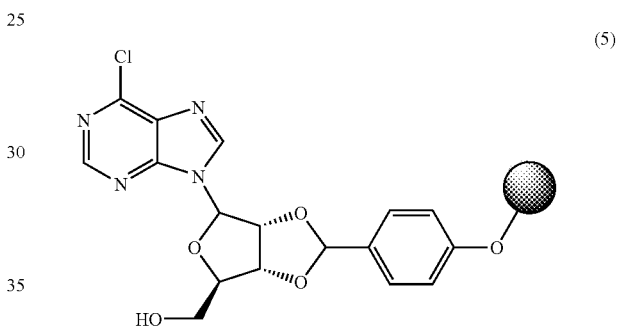

(5)

p-Benzyloxybenzaldehyde polystyrene resin (1) (100 g, 3.0 mmol/g, 0.3 mol, 150-300 μm, Polymer Labs) was suspended in dry trimethylorthoformate (1 L). p-Toluenesulfonic acid monohydrate (5.70 g, 0.03 mol, 0.1 eq) was added and the suspension shaken at room temperature for 48 hours. Triethylamine (60 mL) was added, and the resin was promptly filtered, washed 4× with methylene chloride containing 1% triethylamine, and dried under vacuum for 24 hours to afford the dimethylacetal resin Dimethylacetal resin (20.0 g, 3 mmol/g, 60.0 mmol) was suspended in anhydrous N,N-dimethylacetamide (300 mL), and treated sequentially with the riboside of formula (1) (34.4 g, 120 mmol, 2 eq) and 10-camphorsulfonic acid (2.78 g, 12.0 mmol, 0.2 eq.). The mixture was shaken at 200 rpm at room temperature for 96 hours. Triethylamine (4.2 mL, 30.0 mmol, 0.5 eq) was then added and the resin promptly filtered, washed once with N,N-dimethylacetamide, washed with four alternating cycles of methylene chloride containing 1% $Et_3N$ and MeOH containing 1% triethylamine, and finally by three washes with methylene chloride containing 1% triethylamine. The recovered resin was dried under vacuum for 48 hours to provide the resin-bound riboside of formula (5).

Example 6

Preparation of a Compound of Formula (6)

A. Preparation of a Compound of Formula (6) in which R and $R^2$ are Hydrogen, Y is a Covalent Bond, and $R^1$ is Cyclopentyl (6)

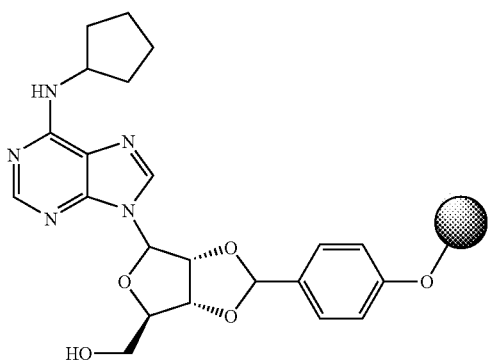

In a reaction vessel was placed the resin-bound riboside of formula (5) (30 mg resin; resin loading 1.5 mmol/g) suspended in anhydrous 1,4-dioxane (30 mL). Diisopropylethylamine (2.4 mL, 13.5 mmol, 20 eq) and excess cyclopentylamine were then added. The reaction vessel was heated at 80° C. for 48 hours with no stirring or agitation. After cooling to room temperature the solvent was removed, and methanol containing 1% triethylamine (50 mL) was added to shrink the resin. The product was washed with four alternating cycles of methanol containing 1% triethylamine and methylene chloride containing 1% triethylamine, and dried overnight in vacuo to provide the resin-bound compound of formula (6).

Example 7

Preparation of a Compound of Formula (7)

A. Preparation of a Compound of Formula (7) in which R and $R^2$ are Hydrogen, Y is a Covalent Bond, $R^1$ is Cyclopentyl, and $R^3$ is 2-Fluorophenyl (7)

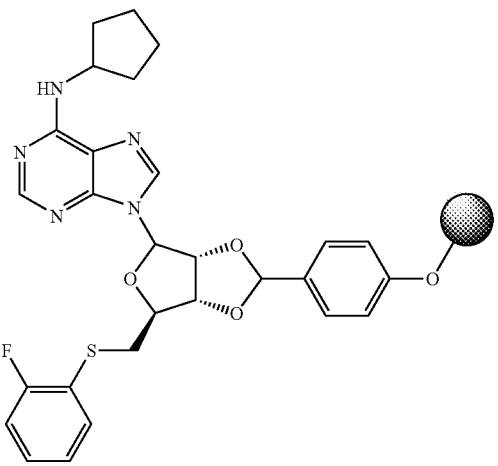

The product from Example 6 was suspended in anhydrous pyridine (2 mL) and treated with diisopropylethylamine (0.13 mL). After cooling to 0° C., methanesulfonyl chloride (0.035 mL, 337 mmol) was added dropwise. The reaction mixture was agitated regularly by hand during the addition. After 90 minutes the reaction mixture was warmed to room temperature and shaken for 24 hours. After removal of the reaction mixture, the product was rinsed with anhydrous methylene chloride containing 1% triethylamine and treated with methanol containing 1% triethylamine to shrink the resin, to provide a mesylated derivative of the resin-bound compound of formula (6).

The mesylate was then suspended in acetonitrile (1.5 mL) and treated with excess diisopropylethylamine (0.16 mL) followed by water (0.7 mL) and 2-fluorothiophenol (45 mmol). The reaction vessel was warmed to approximately 80° C. without agitation for 65 hours. The product was washed with four alternating cycles of methanol containing 1% triethylamine and methylene chloride containing 1% triethylamine, and dried overnight in vacuo, to provide a resin bound compound of formula (7).

Example 8

Preparation of a Compound of Formula I

A. Preparation of a Compound of Formula I in which R is Hydrogen, $R^1$ is Cyclopentyl, $R^2$ is Hydrogen, $R^3$ is 2-Fluorophenyl, and X and Y are Covalent Bonds

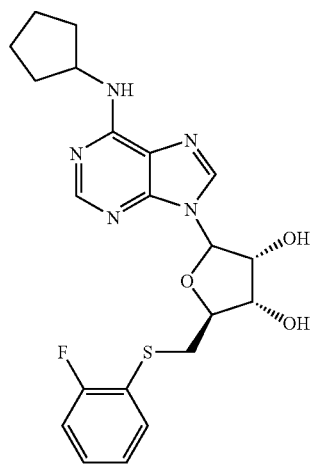

The resin bound compound of formula (7) was suspended in a solution of 2% trifluoroacetic acid/5% methanol/methylene chloride and shaken (200 rpm) at room temperature for 2 hours. After removal of the solution, the residue was rinsed with methylene chloride (3×0.5 mL), and the combined filtrates were concentrated under reduced pressure to afford (4S,5S,3R)-2-[6-(cyclopentylamino)purin-9-yl]-5-[(2-fluorophenylthio)methyl]oxolane-3,4-diol, a compound of Formula I.

Example 9

Preparation of a Compound of Formula (9)

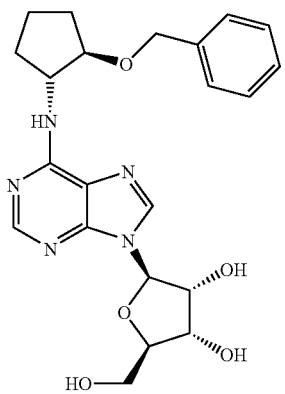

To a solution of 6-chloropurine riboside (10.0 g, 35 mmol) in ethanol (350 mL) was added triethylamine (10.0 mL, 100 mmol) and (1R,2R)-2-(benzyloxy)-cyclopentylamine (5.2 g, 52 mmol). The mixture was refluxed for 24 hours, during which the reaction went from a suspension to a clear solution. The ethanol was removed under reduced pressure, and the residue was partitioned between ethyl acetate and water (100 mL:200 mL). The organic layer was separated and the aqueous layer washed with ethyl acetate (2×75 mL). The combined organic layers were dried (sodium sulfate), and the solvent was removed under reduced pressure. The residue was dissolved in ethyl acetate (150 mL), and product precipitated by addition of hexane, to afford 2-(6-{[(1R,2R)-2-(phenylmethoxy)cyclopentyl]amino}purin-9-yl)(4S,3R,5R)-5-(hydroxymethyl)oxolane-3,4-diol as a white solid.

$^1$H NMR (CD$_3$OD) δ 1.62-2.16 (m, 6H), 3.26-3.29 (m, 1H, NHCH), 3.68-3.85 (m, 2H, CH$_2$-5'), 4.03-4.10 (m, 1H, CH-4'J, 4.12-4.16 (m, 1H, CHOBn), 4.16-4.19 (m, 1H, 3'CH), 4.71 (s, 2H, OCH$_2$Ph), 4.83-4.92 (m, 1H, 2'CH), 5.98 (d, J=6 Hz, 1H, H-1'), 7.23-7.35 (m, 5H, PhH), 8.15 (S, 1H, C-2H).

B. Preparation of a Compound of Formula (9)

Similarly, following the procedure of 9A above, but replacing (1R,2R)-2-(benzyloxy)cyclopentylamine by other isomers of 2-(benzyloxy)cyclopentylamine, the following compounds are prepared:

2-(6-{[(1S,2S)-2-(phenylmethoxy)cyclopentyl]
amino}purin-9-yl)(4S,3R,5R)-5-(hydroxymethyl)oxolane-3,4-diol;

2-(6-{[(1R,2S)-2-(phenylmethoxy)cyclopentyl]
amino}purin-9-yl)(4S,3R,5R)-5-(hydroxymethyl)oxolane-3,4-diol;

2-(6-{[(1S,2R)-2-(phenylmethoxy)cyclopentyl]
amino}purin-9-yl)(4S,3R,5R)-5-(hydroxymethyl)oxolane-3,4-diol; and 2-(6-{[(1RS,2RS)-2-(phenylmethoxy)cyclopentyl]
amino}purin-9-yl)(4S,3R,5R)-5-(hydroxymethyl)oxolane-3,4-diol.

Example 10

Preparation of a Compound of Formula (10)

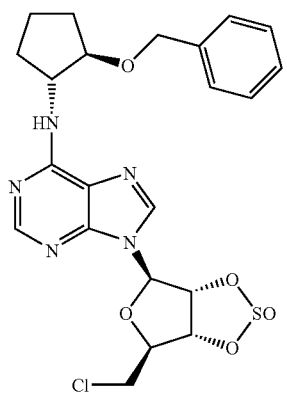

To a stirred suspension of 2-(6-{[(1R,2R)-2-(phenylmethoxy)cyclopentyl]-amino}purin-9-yl)(4S,3R,5R)-5-(hydroxymethyl)oxolane-3,4-diol (2.0 g, 4.5 mmol) in acetonitrile (15 mL) and pyridine (0.728 g, 9 mmol) at 0 C was added dropwise thionyl chloride (1.7 mL, 22.5 mmol). After stirring for 4 hours at 0 C, the reaction was allowed to warm to room temperature, and then stirred overnight. Solvent was removed from the resulting suspension under reduced pressure, to afford 4-(6-{[(1R,2R)-2-(phenylmethoxy)cyclopentyl]amino}purin-9-yl)(6S,3aR,6aR)-6-(chloromethyl)-4H, 6H,3aH,6aH-oxolano[3,4-d]1,3,2-dioxathiolan-2-one, which was taken to the next step without further purification.

B. Preparation of a Compound of Formula (10)

Similarly, following the procedure of 10A above, but replacing 2-(6-{[(1R,2R)-2-(phenylmethoxy)cyclopentyl]-amino}purin-9-yl)(4S,3R,5R)-5-(hydroxymethyl)oxolane-3,4-diol by other isomers of 2-(6-{[2-(phenylmethoxy)cyclopentyl]-amino}purin-9-yl)(4S,3R,5R)-5-(hydroxymethyl)oxolane-3,4-diol, the following compounds are prepared:

4-(6-{[(1S,2S)-2-(phenylmethoxy)cyclopentyl]
amino}purin-9-yl)(6S,3aR,6aR)-6-(chloromethyl)-4H, 6H,3aH,6aH-oxolano[3,4-d]1,3,2-dioxathiolan-2-one;

4-(6-{[(1R,2S)-2-(phenylmethoxy)cyclopentyl]
amino}purin-9-yl)(6S,3aR,6aR)-6-(chloromethyl)-4H, 6H,3aH,6aH-oxolano[3,4-d]1,3,2-dioxathiolan-2-one;

4-(6-{[(1S,2R)-2-(phenylmethoxy)cyclopentyl]
amino}purin-9-yl)(6S,3aR,6aR)-6-(chloromethyl)-4H, 6H,3aH,6aH-oxolano[3,4-d]1,3,2-dioxathiolan-2-one; and 4-(6-{[(1RS,2RS)-2-(phenylmethoxy)cyclopentyl]
amino}purin-9-yl)(6S,3aR,6aR)-6-(chloromethyl)-4H, 6H,3aH,6aH-oxolano[3,4-d]1,3,2-dioxathiolan-2-one.

Example 11

Preparation of a Compound of Formula (11)

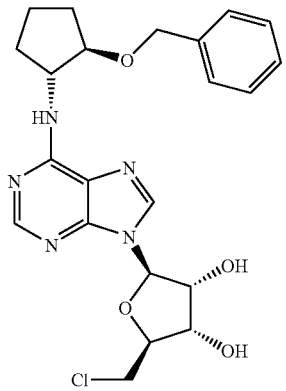

The 4-(6-{[(1R,2R)-2-(phenylmethoxy)cyclopentyl]amino}purin-9-yl)(6S,3aR,6aR)-6-(chloromethyl)-4H,6H, 3aH,6aH-oxolano[3,4-d]1,3,2-dioxathiolan-2-one from Example 10 was dissolved in a mixture of methanol and water (40 mL/2 mL), and to this solution was added concentrated ammonium hydroxide (2.2 mL, 28%) dropwise. After stirring for 30 minutes at 23 C, the solvent was removed under reduced pressure and the residue diluted with water (15 mL). The aqueous mixture was extracted with ethyl acetate (3×75 mL), dried over MgSO4, and solvent removed under reduced pressure to provide 2-(6-{[(1R,2R)-2-(phenylmethoxy)cyclopentyl]amino}purin-9-yl)(4S,5S,3R)-5-(chloromethyl) oxolane-3,4-diol, which was used in the next step without further purification.

B. Preparation of a Compound of Formula (II)

Similarly, following the procedure of 11A above, but replacing 4-(6-{[(1R,2R)-2-(phenylmethoxy)cyclopentyl] amino}purin-9-yl)(6S,3aR,6aR)-6-(chloromethyl)-4H,6H, 3aH,6aH-oxolano[3,4-d]1,3,2-dioxathiolan-2-one with other isomers of 4-(6-{[2-(phenylmethoxy)cyclopentyl]amino}purin-9-yl)(6S,3aR,6aR)-6-(chloromethyl)-4H,6H,3aH,6aH-oxolano[3,4-d]1,3,2-dioxathiolan-2-one, the following compounds are made:

2-(6-{[(1S,2S)-2-(phenylmethoxy)cyclopentyl]amino}purin-9-yl)(4S,5S,3R)-5-(chloromethyl)oxolane-3,4-diol;

2-(6-{[(1R,2S)-2-(phenylmethoxy)cyclopentyl]amino}purin-9-yl)(4S,5S,3R)-5-(chloromethyl)oxolane-3,4-diol;

2-(6-{[(1S,2R)-2-(phenylmethoxy)cyclopentyl]amino}purin-9-yl)(4S,5S,3R)-5-(chloromethyl)oxolane-3,4-diol; and 2-(6-{[(1RS,2RS)-2-(phenylmethoxy)cyclopentyl]amino}purin-9-yl)(4S,5S,3R)-5-(chloromethyl)oxolane-3,4-diol.

Example 12

Preparation of a Compound of Formula (12)

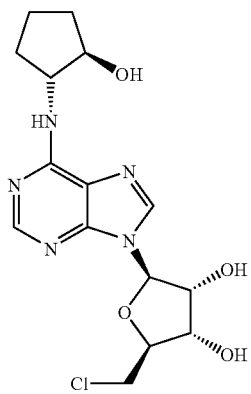

The 2-(6-{[(1R,2R)-2-(phenylmethoxy)cyclopentyl]amino}purin-9-yl)(4S,5S,3R)-5-(chloromethyl)oxolane-3,4-diol obtained in Example 11 (22 g) was dissolved in ethanol (450 mL) and cyclohexane (200 mL). To this solution was added palladium hydroxide (20 mole %, 1 gram added initially, 1 gram after 6 hours, and 1 gram after 14 hours), and the reaction mixture was refluxed for 18 hours. The reaction mixture was filtered thru celite while still hot, and solvent removed from the filtrate under reduced pressure. The product was triturated with ethanol (20 mL), filtered, and washed with ethanol, to afford 2-{6-[((1R,2R)-2-hydroxycyclopentyl)amino]purin-9-yl}(4S,5S,3R)-5-(chloromethyl)oxolane-3,4-diol as a white powder).

Further material was recovered by suspending the retrieved palladium hydroxide in methanol (200 mL), and warming the mixture at 90° C. for 1 hour. The hot mixture was filtered thru Celite®, and the celite was further washed with hot methanol. The filtrate was concentrated under reduced pressure, and the residue triturated with ethanol (20 mL) to afford a further 8.6 grams of 2-{6-[((1R,2R)-2-hydroxycyclopentyl)amino]purin-9-yl}(4S,5S,3R)-5-(chloromethyl)oxolane-3,4-diol.

$^1$H NMR (DMSO-d6) δ 1.64-2.18 (m, 6H), 3.26-3.29 (m, 1H, NHCH), 3.83-3.97 (m, 2H, CH$_2$Cl 5'), 4.03-4.09 (m, 1H, CH-4'), 4.12-4.17 (m, 1H, CHOH), 4.16-4.19 (m, 1H, 3'CH), 4.84-4.92 (m, 1H, 2'CH), 5.96 (d, J=6 Hz, 1H, H-1'), 7.23-7.35 (m, 5H, PhH), 8.15 (S, 1H, C-2H), 8.39 (s, 1H, C-8H).

B. Preparation of a Compound of Formula (12)

Similarly, following the procedure of 12A above, but replacing 2-(6-{[(1R,2R)-2-(phenylmethoxy)cyclopentyl]amino}purin-9-yl)(4S,5S,3R)-5-(chloromethyl)oxolane-3,4-diol by other isomers of 2-(6-{[2-(phenylmethoxy)cyclopentyl]amino}purin-9-yl)(4S,5S,3R)-5-(chloromethyl)oxolane-3,4-diol, the following compounds are made:

2-(6-{[(1S,2S)-2-(phenylmethoxy)cyclopentyl]amino}purin-9-yl)(4S,5S,3R)-5-(chloromethyl)oxolane-3,4-diol;

2-(6-{[(1R,2S)-2-(phenylmethoxy)cyclopentyl]amino}purin-9-yl)(4S,5S,3R)-5-(chloromethyl)oxolane-3,4-diol;

2-(6-{[(1S,2R)-2-(phenylmethoxy)cyclopentyl]amino}purin-9-yl)(4S,5S,3R)-5-(chloromethyl)oxolane-3,4-diol; and 2-(6-{[(1RS,2RS)-2-(phenylmethoxy)cyclopentyl]amino}purin-9-yl)(4S,5S,3R)-5-(chloromethyl)oxolane-3,4-diol.

Example 13

Preparation of a Compound of Formula I in which R is 2-Fluorophenyl

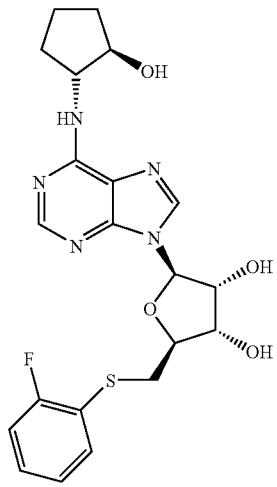

To a solution of 2-fluorothiophenol (38 mL, 406 mmol) in 2N sodium hydroxide (100 mL) was added 2-{6-[((1R,2R)-2-hydroxycyclopentyl)amino]purin-9-yl}(4S,5S,3R)-5-(chloromethyl)oxolane-3,4-diol (15.0 g, 40.6 mmol) in N,N-dimethylformamide (120 mL). The mixture was warmed to 100 C for 4 hours, following the progress of the reaction by TLC. The N,N-dimethylformamide was removed under reduced pressure, and the remaining mixture was diluted with water (200 mL), neutralized with acetic acid, extracted with ethyl acetate (3×125 mL), and the combined organic layers were dried over MgSO$_4$. After removing the solvent under reduced pressure the residue was triturated with diethyl ether and filtered, to afford 16 grams of 2-{6-[((1R,2R)-2-hydroxycyclopentyl)amino]purin-9-yl}(4S,5S,3R)-5-[(2-fluorophenylthio)methyl]oxolane-3,4-diol as a white powder.

$^1$H NMR (DMSO-d6) δ 1.66-2.27 (m, 6H), 3.42-3.59 (m, 1H, NHCH), 4.05-4.14 (m, 2H), 4.03-4.09 (m, 1H, CH-4'), 4.14-4.19 (m, 1H), 4.16-4.19 (m, 1H, 3'CH), 4.84-4.92 (m, 1H, 2'CH), 5.97 (d, J=6 Hz, 1H, H-1'), 7.05-7.55 (m, 4H, PhH), 8.10 (S, 1H, C-2H), 8.15 (s, 1H, C-8H).

B. Preparation of a Compound of Formula I in which R is 2-Fluorophenyl

Similarly, following the procedure of 13A above, but replacing 2-{6-[((1R,2R)-2-hydroxycyclopentyl)amino]purin-9-yl}(4S,5S,3R)-5-(chloromethyl)oxolane-3,4-diol by other isomers of 2-{6-[(2-hydroxycyclopentyl)amino]purin-9-yl}(4S,5S,3R)-5-(chloromethyl)oxolane-3,4-diol, the following compounds are made:

2-{6-[((1S,2S)-2-hydroxycyclopentyl)amino]purin-9-yl}(4S,5S,3R)-5-[(2-fluorophenylthio)methyl]oxolane-3,4-diol;

2-{6-[((1R,2S)-2-hydroxycyclopentyl)amino]purin-9-yl}(4S,5S,3R)-5-[(2-fluorophenylthio)methyl]oxolane-3,4-diol;

2-{6-[((1S,2R)-2-hydroxycyclopentyl)amino]purin-9-yl}(4S,5S,3R)-5-[(2-fluorophenylthio)methyl]oxolane-3,4-diol; and 2-{6-[((1RS,2RS)-2-hydroxycyclopentyl)amino]purin-9-yl}(4S,5S,3R)-5-[(2-fluorophenylthio)methyl]oxolane-3,4-diol.

C. Preparation of a Compound of Formula I Varying R

Similarly, following the procedure of 13A above, but replacing 2-fluorothiophenol by other thiophenols of formula RSH, other compounds of Formula I are prepared.

Example 14

Preparation of a Compound of Formula (19)

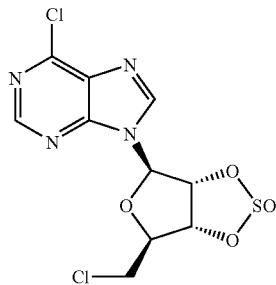

Preparation 1

To a cold (0° C., ice bath) suspension of 6-chloropurine riboside (50.0 g, 174.4 mmol) in dry acetonitrile (600 ml) and distilled pyridine (30 ml, 370 mmol) was added dropwise thionyl chloride (SOCl$_2$, 66.0 ml, 907 mmol) over a 55-minute period. The reaction mixture was stirred at 0° C. for 3 hours and then at room temperature for 18 hours. The yellow solution was concentrated at 40° C. under reduced pressure, and then dried under high vacuum for 6 hours. The residue, (6S,4R,3aR,6aR)-6-(chloromethyl)-4-(6-chloropurin-9-yl)-4H,6H,3aH,6aH-oxolano[3,4-d]1,3,2-dioxathiolan-2-one (12), was used in the next reaction with no further purification.

2. Alternative Preparation of a Compound of Formula (19)

To a mixture of 6-chloropurine riboside (1 Kg) in dry dichloromethane (15 liters) and distilled pyridine (850 ml) was added dropwise thionyl chloride (SOCK, 530 ml), maintaining the temperature at below 30° C. over period of 30-60 minutes. The reaction mixture was stirred at 30° C. for 4 hours, and then cooled to 20° C. Absolute ethanol (1700 ml) was added, maintaining the temperature at 20° C., and the mixture stirred for 15 minutes. Water (3.5 liters) was then added slowly, and the mixture stirred for 30 minutes, after which the contents were allowed to separate. The phases were separated, and the organic layer washed with saturated sodium bicarbonate 4 liters). After separation of the two phases, the organic layer was washed with saturated sodium chloride 2.6 liters); separated, and the solvent was removed under reduced pressure until a volume of approximately 4 liters was reached, providing a solution of (6S,4R,3aR,6aR)-6-(chloromethyl)-4-(6-chloropurin-9-yl)-4H,6H,3aH,6aH-oxolano[3,4-d]1,3,2-dioxathiolan-2-one (12) in solution, which was used in the next reaction with no further purification.

Example 15

Preparation of a Compound of Formula (20)

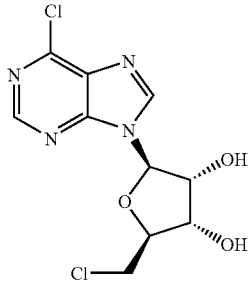

The compound of formula (19) obtained from Example 14 (preparation 1) was dissolved in methanol (1000 ml) and distilled water (50 ml). The solution was cooled to 0° C. and concentrated aqueous ammonia (28%, 56 ml) was added dropwise over 25 minutes. Stirring was continued at 0° C. for 1 hour and then at room temperature for 3 hours. During this time an additional 10 ml of concentrated aqueous ammonia (28%) was added (progress of the reaction was followed by TLC, CH$_2$Cl$_2$/MeOH, 9:1). The reaction mixture was then concentrated under reduced pressure and the residue was hydrolyzed with a 5% aqueous solution of citric acid (1000 ml) at room temperature. The aqueous layer was extracted with ethyl acetate (1×900 ml, 1×400 ml, 1×200 ml, 2×100 ml), and the combined organic layers were washed with saturated sodium bicarbonate (450 ml). The aqueous sodium bicarbonate layer was extracted with ethyl acetate (3×50 ml). The combined organic layers were washed with brine (400 ml), and the aqueous sodium chloride layer was also extracted with ethyl acetate (3×50 ml). The combined organic layers were dried over sodium sulfate, filtered, and the filtrate concentrated under reduced pressure to give 41.8 g of (4S,5S,2R,3R)-5-(chloromethyl)-2-(6-chloropurin-9-yl)oxolane-3,4-diol, the compound of formula (13). No further purification was carried out.

Preparation 2.

Alternatively, to the solution of 6S,4R,3aR,6aR)-6-(chloromethyl)-4-(6-chloropurin-9-yl)-4H,6H,3aH,6aH-oxolano[3,4-d]1,3,2-dioxathiolan-2-one (12) in solution obtained in Example 14, preparation 2, was added ammonium hydroxide (500 ml), and the mixture stirred at 25° C. for 12 hours. The solid was filtered off, and washed with dichloromethane (500 ml). The filtrate and the wash were combined, and the volume reduced under vacuum to about 6 liters. No further purification was carried out.

Example 16

Preparation of a Compound of Formula (18)

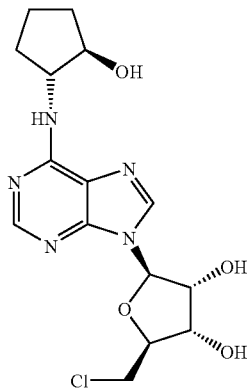

Preparation 1

To a suspension of (R,R)-2-aminopentanol hydrochloride (34.2 g, 249 mmol) in degassed isopropanol (100 ml) and distilled triethylamine (dried over calcium hydride, 95 ml, 69 g, 226 mmol) was added dropwise a solution of (4S,5S,2R,3R)-5-(chloromethyl)-2-(6-chloropurin-9-yl)oxolane-3,4-diol (36.3 g, 118.7 mmol) in 400 ml of isopropanol. The reaction mixture was stirred at room temperature for 30 minutes, and then refluxed (oil bath temperature: ~80° C.) for 20 hours. After cooling the reaction mixture to ambient temperature, the solvent was removed under reduced pressure, and 1000 ml of water was added to the residue. The suspension was stirred at room temperature for 3.5 hours, and the solid material filtered off, washed with water (1×60 ml and 1×90 ml), and dried under vacuum over $P_2O_5$ for 3 days to yield 68.0 g (81%) of 2-{6-[((1R,2R)-2-hydroxycyclopentyl)amino]purin-9-yl}(4S,5S,3R)-5-(chloromethyl)oxolane-3,4-diol as a light brown powder.

Preparation 2

Alternatively, the solution obtained in Example 15, preparation 2, was cooled to 20-25° C., and triethylamine (1000 ml) added, followed by (R,R)-2-aminopentanol (530 g). The mixture was refluxed for 8 hours, and then the solvent removed at atmospheric pressure until a volume of about 4 liters was reached. The mixture was cooled to 55-60° C., water (15 liters) added, and the mixture cooled to 20-25° C. The mix was stirred for about 1 hour, and then filtered, washing the solid with absolute ethanol (1.25 liters), and the solid dried under reduced pressure, not allowing the temperature to exceed 60° C.

B. Similarly, following the procedure of 16A (preparation 1 or preparation 2) above, but replacing (R,R)-2-aminopentanol hydrochloride with (S,S)-2-aminopentanol hydrochloride, 2-{6-[((1S,2S)-2-hydroxycyclopentyl)amino]purin-9-yl}(4S,5S,3R)-5-(chloromethyl)oxolane-3,4-diol is made.

C. Similarly, following the procedure of 16A (preparation 1 or preparation 2) above, but replacing (R,R)-2-aminopentanol hydrochloride with (1R,2S)-2-aminopentanol hydrochloride, 2-{6-[((1R,2S)-2-hydroxycyclopentyl)amino]purin-9-yl}(4S,5S,3R)-5-(chloromethyl)oxolane-3,4-diol is made.

D. Similarly, following the procedure of 16A (preparation 1 or preparation 2) above, but replacing (R,R)-2-aminopentanol hydrochloride with (1S,2R)-2-aminopentanol hydrochloride, 2-{6-[((1S,2R)-2-hydroxycyclopentyl)amino]purin-9-yl}(4S,5S,3R)-5-(chloromethyl)oxolane-3,4-diol is made.

Example 17

Preparation of a Compound of Formula I in which R is 2-Fluorophenyl

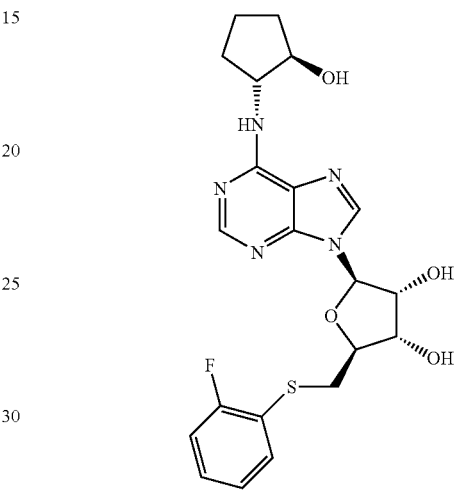

Preparation 1

To a solution of 2-{6-[((1R,2R)-2-hydroxycyclopentyl)amino]-purin-9-yl}(4S,5S,3R)-5-(chloromethyl)oxolane-3,4-diol (166.5 g, 0.457 mol) and triethylamine distilled from calcium hydride (352 ml, 256 g, 2.53 mol, 4 equivalents) in degassed anhydrous N,N-dimethylformamide (1.8 liters) was added 2-fluorothiophenol (190 ml, 228 g, 1.78 mol, 4 equiv) in 38 5 ml portions every 2-3 hours. The mixture was stirred at room temperature for 4 days with continuous bubbling of nitrogen into the solution (the reaction was monitored by $^1$H NMR). After the reaction was complete, the reaction mixture was poured into 7 liters of ethyl acetate, which was washed with 3 liters of water. The aqueous layer extracted with ethyl acetate (2×500 ml), and the combined organic layers were washed with water (3×2 liters), then reduced to a volume of about 1.8 liters, providing a suspension of a white solid. The suspension was stirred for 9 hours at room temperature, and the white precipitate filtered off, washed with diethyl ether (3×200 ml), and dried for 24 hours under high vacuum to give 131 g (63% yield) of 2-{6-[((1R,2R)-2-hydroxycyclopentyl)amino]purin-9-yl}(4S,5S,3R)-5-[(2-fluorophenylthio)methyl]-oxolane-3,4-diol as a white powder (98.9% pure).

$^1$H NMR (DMSO-d6) δ 1.66-2.27 (m, 6H), 3.42-3.59 (m, 1H, NHCH), 4.05-4.14 (m, 2H), 4.03-4.09 (m, 1H, CH-4'), 4.14-4.19 (m, 1H), 4.16-4.19 (m, 1H, 3'CH), 4.84-4.92 (m, 1H, 2'CH), 5.97 (d, J=6 Hz, 1H, H-1'), 7.05-7.55 (m, 4H, PhH), 8.10 (S, 1H, C-2H), 8.15 (s, 1H, C-8H).

The product was further purified by stirring in 1 liter of ethyl ether/ethanol (50:1) overnight, to give 127 g of pure 2-{6-[((1R,2R)-2-hydroxycyclopentyl)amino]purin-9-yl}(4S,5S,3R)-5-[(2-fluorophenylthio)methyl]-oxolane-3,4-diol.

Preparation 2

The product of Example 16, preparation 2 (1 Kg), was dissolved in N,N-dimethylacetamide (2.7 liters), and potassium carbonate (560 g) added. To the mixture, maintained at below 25° C., was added 2-fluorothiophenol (380 g), and the mixture was heated at 60-65 for about 6 hours. The mixture was then cooled to 25-30° C., and ethyl acetate (10 liters) added, followed by a solution of sodium chloride (260 g) in water (4.9 liters), and the mixture stirred for 15 minutes. After separation of the two layers, the organic phase was again washed with a solution of sodium chloride (260 g) in water (4.9 liters), and the mixture stirred for 15 minutes. After separation, the organic layer was concentrated at atmospheric pressure to a volume of about 5 liters, and methanol (10 liters) was added. The mixture was again concentrated at atmospheric pressure to a volume of about 2.8 liters, and the resulting solution cooled to about 35-40° C. Dichloromethane (5 liters) was then added, and the mixture maintained at about 35-40° C. for 1 hour, followed by cooling to between 0-5° C. for 30 minutes. The solid product was filtered off, washed with dichloromethane (2.8 liters), and dried under reduced pressure to constant weight, not allowing the temperature to rise above 50° C., to provide 2-{6-[((1R,2R)-2-hydroxycyclopentyl)amino]purin-9-yl}(4S,5S,3R)-5-[(2-fluorophenylthio)methyl]-oxolane-3,4-diol.

The product was further purified by dissolving 1 Kg of the product (2-{6-[((1R,2R)-2-hydroxycyclopentyl)amino]purin-9-yl}(4S,5S,3R)-5-[(2-fluorophenylthio)methyl]-oxolane-3,4-diol) in methanol (20 liters) at a temperature between 60-70° C., maintaining that temperature for 1 hour, cooling to 45-50° C., and then filtering the solution through a 1 micron filter, maintaining the solution temperature above 40° C. The solution was concentrated to about 7 liters, maintaining the solution temperature above 40° C., and the resultant solution was maintained at 50-55° C. for 1 hour. The solution was then cooled to −5° C. over a period of 2 hours, and the temperature maintained at −5° C. for 1 hour. The product was filtered off at −5° C., and the filtrate was used to wash the solid, to provide pure (2-{6-[((1R,2R)-2-hydroxycyclopentyl)amino]purin-9-yl}(4S,5S,3R)-5-[(2-fluorophenylthio)methyl]-oxolane-3,4-diol).

B. Preparation of a Compound of Formula I in which R is 2-Fluorophenyl

Similarly, following the procedure of 17A above (preparation 1 or 2), but replacing 2-{6-[((1R,2R)-2-hydroxycyclopentyl)amino]purin-9-yl}(4S,5S,3R)-5-(chloromethyl)oxolane-3,4-diol by other isomers of 2-{6-[(2-hydroxycyclopentyl)amino]purin-9-yl}(4S,5S,3R)-5-(chloromethyl)oxolane-3,4-diol, the following compounds are made:

2-{6-[((1S,2S)-2-hydroxycyclopentyl)amino]purin-9-yl}(4S,5S,3R)-5-[(2-fluorophenylthio)methyl]oxolane-3,4-diol;

2-{6-[((1R,2S)-2-hydroxycyclopentyl)amino]purin-9-yl}(4S,5S,3R)-5-[(2-fluorophenylthio)methyl]oxolane-3,4-diol;

2-{6-[((1S,2R)-2-hydroxycyclopentyl)amino]purin-9-yl}(4S,5S,3R)-5-[(2-fluorophenylthio)methyl]oxolane-3,4-diol; and 2-{6-[((1RS,2RS)-2-hydroxycyclopentyl)amino]purin-9-yl}(4S,5S,3R)-5-[(2-fluorophenylthio)methyl]oxolane-3,4-diol.

C. Preparation of a Compound of Formula I Varying R

Similarly, following the procedure of 17A (preparation 1 or 2) above, but replacing 2-fluorothiophenol by other thiophenols of formula RSH, other compounds of Formula I are prepared.

Example 18

Hard gelatin capsules containing the following ingredients are prepared:

| Ingredient | Quantity (mg/capsule) |
|---|---|
| Active Ingredient | 30.0 |
| Starch | 305.0 |
| Magnesium stearate | 5.0 |

The above ingredients are mixed and filled into hard gelatin capsules.

Example 19

A tablet formula is prepared using the ingredients below:

| Ingredient | Quantity (mg/tablet) |
|---|---|
| Active Ingredient | 25.0 |
| Cellulose, microcrystalline | 200.0 |
| Colloidal silicon dioxide | 10.0 |
| Stearic acid | 5.0 |

The components are blended and compressed to form tablets.

Example 20

A dry powder inhaler formulation is prepared containing the following components:

| Ingredient | Weight % |
|---|---|
| Active Ingredient | 5 |
| Lactose | 95 |

The active ingredient is mixed with the lactose and the mixture is added to a dry powder inhaling appliance.

Example 21

Tablets, each containing 30 mg of active ingredient, are prepared as follows:

| Ingredient | Quantity (mg/tablet) |
|---|---|
| Active Ingredient | 30.0 mg |
| Starch | 45.0 mg |
| Microcrystalline cellulose | 35.0 mg |
| Polyvinylpyrrolidone (as 10% solution in sterile water) | 4.0 mg |
| Sodium carboxymethyl starch | 4.5 mg |
| Magnesium stearate | 0.5 mg |
| Talc | 1.0 mg |
| Total | 120 mg |

The active ingredient, starch, and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50° C. to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

Example 22

Suppositories, each containing 25 mg of active ingredient are made as follows:

| Ingredient | Amount |
| --- | --- |
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Example 23

Suspensions, each containing 50 mg of active ingredient per 5.0 mL dose are made as follows:

| Ingredient | Amount |
| --- | --- |
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 mL |

The active ingredient, sucrose, and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Example 24

A subcutaneous formulation may be prepared as follows:

| Ingredient | Quantity |
| --- | --- |
| Active Ingredient | 5.0 mg |
| Corn Oil | 1.0 mL |

Example 25

An injectable preparation is prepared having the following composition:

| Ingredients | Amount |
| --- | --- |
| Active ingredient | 2.0 mg/ml |
| Mannitol, USP | 50 mg/ml |
| Gluconic acid, USP | q.s. (pH 5-6) |
| water (distilled, sterile) | q.s. to 1.0 ml |
| Nitrogen Gas, NF | q.s. |

Example 26

A topical preparation is prepared having the following composition:

| Ingredients | grams |
| --- | --- |
| Active ingredient | 0.2-10 |
| Span 60 | 2.0 |
| Tween 60 | 2.0 |
| Mineral oil | 5.0 |
| Petrolatum | 0.10 |
| Methyl paraben | 0.15 |
| Propyl paraben | 0.05 |
| BHA (butylated hydroxy anisole) | 0.01 |
| Water | q.s. to100 |

All of the above ingredients, except water, are combined and heated to 60° C. with stirring. A sufficient quantity of water at 60° C. is then added with vigorous stirring to emulsify the ingredients, and water then added q.s. 100 g.

Example 27

Sustained Release Composition

| Ingredient | Weight Range (%) | Preferred Range (%) | Most Preferred Range (%) |
| --- | --- | --- | --- |
| Active ingredient | 50-95 | 70-90 | 75 |
| Microcrystalline cellulose (filler) | 1-35 | 5-15 | 10.6 |
| Methacrylic acid copolymer | 1-35 | 5-12.5 | 10.0 |
| Sodium hydroxide | 0.1-1.0 | 0.2-0.6 | 0.4 |
| Hydroxypropyl methylcellulose | 0.5-5.0 | 1-3 | 2.0 |
| Magnesium stearate | 0.5-5.0 | 1-3 | 2.0 |

The sustained release formulations of this invention are prepared as follows: compound and pH-dependent binder and any optional excipients are intimately mixed (dry-blended). The dry-blended mixture is then granulated in the presence of an aqueous solution of a strong base, which is sprayed into the blended powder. The granulate is dried, screened, mixed with optional lubricants (such as talc or magnesium stearate), and compressed into tablets. Preferred aqueous solutions of strong bases are solutions of alkali metal hydroxides, such as sodium or potassium hydroxide, preferably sodium hydroxide, in water (optionally containing up to 25% of water-miscible solvents such as lower alcohols).

The resulting tablets may be coated with an optional film-forming agent, for identification, taste-masking purposes and to improve ease of swallowing. The film forming agent will typically be present in an amount ranging from between 2% and 4% of the tablet weight. Suitable film-forming agents are well known to the art and include hydroxypropyl methylcellulose, cationic methacrylate copolymers (dimethylaminoethyl methacrylate/methyl-butyl methacrylate copolymers—Eudragit® E—Röhm. Pharma), and the like. These film-forming agents may optionally contain colorants, plasticizers, and other supplemental ingredients.

The compressed tablets preferably have a hardness sufficient to withstand 8 Kp compression. The tablet size will depend primarily upon the amount of compound in the tablet. The tablets will include from 300 to 1100 mg of compound free base. Preferably, the tablets will include amounts of compound free base ranging from 400-600 mg, 650-850 mg, and 900-1100 mg.

In order to influence the dissolution rate, the time during which the compound containing powder is wet mixed is controlled. Preferably, the total powder mix time, i.e. the time during which the powder is exposed to sodium hydroxide solution, will range from 1 to 10 minutes and preferably from 2 to 5 minutes. Following granulation, the particles are removed from the granulator and placed in a fluid bed dryer for drying at about 60° C.

Example 28

Binding Assays $DDT_1$ Cells

Cell Culture

DDT cells (hamster vas deferens smooth muscle cell line) were grown as monolayers in petri dishes using Dulbecco's Modified Eagle's Medium (DMEM) containing 2.5 µg ml$^{-1}$ amphotericin B, 100 U ml$^{-1}$ penicillin G, 0.1 mg ml$^{-1}$ streptomycin sulfate and 5% fetal bovine serum in a humidified atmosphere of 95% air and 5% $CO_2$. Cells were subcultured twice weekly by dispersion in Hank's Balanced Salt Solution (HBSS) without the divalent cations and containing 1 mM EDTA. The cells were then seeded in growth medium at a density of $1.2 \times 10^5$ cells per plate and experiments were performed 4 days later at approximately one day preconfluence.

Membrane Preparations

Attached cells were washed twice with HBSS (2×10 ml), scraped free of the plate with the aid of a rubber policeman in 5 ml of 50 mM Tris-HCl buffer pH 7.4 at 4° C. and the suspension homogenized for 10 s. The suspension was then centrifuged at 27,000×g for 10 min. The pellet was resuspended in homogenization buffer by vortexing and centrifuged as described above. The final pellet was resuspended in 1 vol of 50 mM Tris-HCl buffer pH 7.4 containing 5 mM $MgCl_2$ for $A_1$ AdoR assays. For the [$^{35}$S]GTPγS binding assay the final pellet was resuspended in 50 mM Tris-HCl pH 7.4 containing 5 mM $MgCl_2$, 100 mM NaCl and 1 mM dithiothreitol. This membrane suspension was then placed in liquid nitrogen for 10 min, thawed and used for assays. The protein content was determined with a Bradford™ Assay Kit using bovine serum albumin as standard.

Competitive Binding Assay

Pig striatum were prepared by homogenation in 50 mM Tris buffer (5× volume of tissue mass pH=7.4). After centrifugation at 19,000 rpm for 25 minutes at 4° C., the supernatant was discarded, and the process was repeated twice. Compounds of Formula I were assayed to determine their affinity for the $A_1$ receptor in a pig striatum membrane prep or a $DDT_1$ membrane prep. Briefly, 0.2 mg of pig striatal membranes or $DDT_1$ cell membranes were treated with adenosine deaminase and 50 mM Tris buffer (pH=7.4) followed by mixing. To the pig membranes was added 2 µL of serially diluted DMSO stock solution of the compounds of this invention at concentrations ranging from 100 microM to 10 nM. The control received 2 microL of DMSO alone, then the antagonist [$^3$H] 8-cyclopentylxanthine (CPX) for pig striatum or the agonist [$^3$H] 2-chloro-6-cyclopentyladenosine (CCPA) for $DDT_1$ membranes in Tris buffer (50 mM, pH of 7.4) was added to achieve a final concentration of 2 nM. After incubation at 23 C for 2 h, then the solutions were filtered using a membrane harvester using multiple washing of the membranes (3×). The filter disks were counted in scintillation cocktail affording the amount of displacement of tritiated CPX or by the competitive binding of compounds of Formula I.

The compounds of Formula I were shown to be of high, medium, or low affinity for the $A_1$ adenosine receptor in this assay.

Example 29

[$^{35}$S]GTPγS Binding Assays $A_1$-agonist stimulated [$^{35}$S]GTPγS binding was determined by a modification of the method described by Giersckik et al. (1991) and Lorenzen et al. (1993). Membrane protein (30-50 µg) was incubated in a volume of 0.1 ml containing 50 mM Tris-HCl buffer pH 7.4, 5 mM $MgCl_2$, 100 mM NaCl, 1 mM dithiothreitol, 0.2 units ml$^{-1}$ adenosine deaminase, 0.5% BSA, 1 mM EDTA, 10 mM GDP, 0.3 nM [$^{35}$S]GTPγS and with or without varying concentrations of CPA for 90 min at 30° C. Nonspecific binding was determined by the addition of 10 µM GTPγS. Agonist stimulated binding was determined as the difference between total binding in the presence of CPA and basal binding determined in the absence of CPA. Previous reports have shown that agonist stimulated [$^{35}$S]GTPγS binding was dependent on the presence of GDP (Giersehik et al., 1991; Lorenzen et al., 1993; Traynor & Nahorski, 1995). In preliminary experiments, it was found that 10 µM GDP gave the optimal stimulation of CPA dependent [$^{35}$S]GTPγS binding and this concentration was therefore used in all studies. In saturation experiments, 0.5 nM [$^{35}$S]GTPγS was incubated with 0.5-1000 µM GTPγS. At the end of the incubation, each suspension was filtered and the retained radioactivity determined as described above.

The compounds of Formula I were shown to be partial or full agonists of the $A_1$ adenosine receptor in this assay.

Example 30 cAMP Assay

A scintillation proximity assay (SPA) using rabbit antibodies directed at cAMP using an added tracer of adenosine 3',5'-cyclic phosphoric acid 2'-O-succinyl-3-[$^{125}$I]iodotyrosine methyl ester and fluoromicrospheres containing anti-rabbit specific antibodies as described by Amersham Pharmacia Biotech (Biotrak cellular communication assays). Briefly, $DDT_1$ cells were cultured in clear bottomed 96 well microtiter plates with opaque wells at concentrations between $10^4$ to $10^6$ cells per well in 40 µl of HBSS at 37° C. (5% $CO_2$ and 95% humidity). The partial or full $A_1$ agonists (5 µl) of this invention were incubated at various concentrations with the $DDT_1$ cells in the presence of rolipram (50 µM), and 5 µM forskolin for 10 min at 37° C. The cells were immediately lysed by treatment 5 µl of 10% dodecyltrimethylammonium bromide followed by shaking using microplate shaker. After incubation of the plate for 5 minutes, an immunoreagent solution (150 μl containing equal volumes of tracer, antiserum, and SPA fluorospheres) was added to each well followed by sealing the plate. After 15-20 h at 23° C., the amount of bound [$^{125}$I] cAMP to the fluoromicrospheres was determined by counting in a microliter plate scintillation counter for 2 minutes. Comparison of counts with standard curves generated for cAMP using a similar protocol afforded the cAMP present after cell lysis.

The compounds of Formula I were shown to be functionally active as $A_1$ agonists with a partial or full decrease in cAMP in this assay.

Example 31

Biological Activity

Reduction in Free Fatty Acid and Triglyceride Levels

Elevated lipolysis and circulating free fatty acid (FFA) levels have been linked to the pathogenesis of insulin resistance. $A_1$ adenosine receptor agonists are potent inhibitors of lipolysis. Several $A_1$ agonists have been tested as potential anti-lipolytic agents; however, their effect on the cardiovascular system remains a potential problem for development of these agents as drugs. In the present example we report that 2-{6-[((1R,2R)-2-hydroxycyclopentyl)amino]purin-9-yl} (4S,5S,2R,3R)-5-[(2-fluorophenylthio)methyl]oxolane-3,4-diol, (herein after "Compound A"), a novel partial $A_1$ receptor agonist of Formula I, significantly reduces circulating FFA levels without any effect on heart rate and blood pressure in awake rats.

Rats were implanted with indwelling arterial and venous cannulas to obtain serial blood samples, record arterial pressure, and administer drug. Compound A decreased FFA levels in a dose-dependent manner at doses from 1 up to 10 mg/kg. Triglyceride (TG) levels were also significantly reduced by Compound A treatment in the absence and presence of Triton. Tachyphylaxis of the anti-lipolytic effects effect of Compound A (1 mg/kg, iv bolus) was not observed. An acute reduction of FFA by Compound A was not followed by a rebound increase of FFA. The potency of insulin to decrease lipolysis was increased 4-fold (p<0.01) in the presence of Compound A (0.5 mg/kg). In summary, Compound A is an orally bioavailable $A_1$ agonist which lowers circulating FFA and TG levels by inhibiting lipolysis. Compound A has anti-lipolytic effects at doses that do not elicit cardiovascular effects.

Materials and Methods

Animals

All experimental procedures were performed under a protocol approved by the Institutional Animal Care and Use Committee of CV Therapeutics, Inc., and in accordance with the recommendations set forth in the Guide for the Care and Use of Laboratory Animals published by the National Research Council. Male Sprague-Dawley rats (225-250 gm) with either one or two indwelling catheters (carotid and jugular) were purchased from Charles River Laboratories (Wilmington, Mass.). Animals were housed 1 per cage in a room maintained on a 12 h light/dark cycle (light on 06.00-18.00 h) under constant temperature (22-25° C.) and with ad libitum access to food and water.

Experimental Protocol

The anti-lipolytic effects of Compound A were studied in awake rats. Animals were fasted overnight before experimental use. On the day of the experiment, animals were put in metabolic cages and left undisturbed to acclimate to the environment for 1-2 hrs. An infusion set (21 G×¾", 0.8×19 mm U.T.W., 3½", 9 cm tubing, volume 0.15 ml) was connected to the arterial catheter for blood sampling. A 1% sodium citrate saline solution was used to flush the lines. A pre-treatment blood sample was obtained from each animal to determine baseline values for FFA and TG. Compound A was given via oral gavage, sc injection, iv injection, or iv infusion, as described, for each different series of experiments. Blood samples were collected into serum separator tubes (Becton Dickinson, Franklin Lakes, N.J.) at pre-determined times, Blood was allowed to clot, and then centrifuged at 8000 rpm for 4 min at 4° C. The serum was stored at −80° C. and was thawed at 4° C. for determinations of FFA and TG contents.

Cardiovascular Measurements

The effects of Compound A on heart rate and blood pressure were determined in a separate group of animals as heart rate is very easily affected in the un-anesthetized animal by animal handling and blood sampling. Rats were instrumented with radiotelemetered transmitters (Data Sciences) at least 3 weeks prior to experimentation. The ECG, blood pressure and temperature were recorded and heart rate calculated using a Dataquest ART Gold system (Version 2.2; Data Sciences Intl). The system consisted of a transmitter, i.e., biopotential sensor (Model TL11M2-C50-PXT), receivers (Model RPC-1), a consolidation matrix (BCM 100), a personal computer (Compaq DeskPro Series 3574) and Dataquest 4 software. Heart rate, blood pressure and temperature were measured at 5-minute intervals. Each recording lasted 10 seconds and all cardiac cycles within this period were averaged.

Chemicals and Reagents

Compound A was synthesized by the Department of Medicinal and Bio-Organic chemistry of CV Therapeutics, Inc. Sodium citrate and Triton WR1339 were purchased from Sigma (St. Louis, Mo.). Nicotinic acid and PEG 400 were purchased from VWR (by EMD Chemicals). Triton WR 1339 was diluted in warm saline (~37° C.) with frequent vortexing. Nicotinic acid was dissolved in saline. Compound A was dissolved in PEG 400, and then diluted with distilled water to make a 20% PEG drug solution. Serum FFA and TGs were measured using commercial kits from Wako Chemicals, Richmond, Va. Glucose and Insulin were measured using commercial kits from Wako Chemicals USA (Richmond, Va.).

Data Analysis:

All data are reported as mean±SEM. Statistical analysis of data from experiments with 2 treatment groups was performed using the unpaired Student's t-test. Two way analysis of variance followed by Bonferroni's test was used for multiple comparisons. Differences among treatment groups were considered to be significant when the probability of their occurrence by chance alone was <0.05.

Results

Effect of Compound A on Plasma Free Fatty Acid and Triglyceride Levels

Compound A lowered FFA levels in a dose-dependent manner in normal, overnight-fasted awake rats. The time course of the effect of Compound A on circulating serum FFA levels is shown in FIG. 1. There was a small increase in FFA levels in the vehicle group at 10 min after the vehicle gavage. This response is likely due to an increase in lipolysis caused by the increase in sympathetic tone associated with the handling of awake animals. Compound. A at a dose of 2.5 mg/kg lowered FFA levels from 0.7±0.05 to 0.5±0.03 mM, a 31% decrease below baseline levels (p<0.05). Compound A lowered FFA levels by 47% to 0.4±0.03 from 0.8±0.04 mM at a dose of 5 mg/kg dose (p<0.01). A 10 mg/kg dose caused a 57% decrease in FFA levels (from 0.68±0.04 to 0.29±0.02 mM, p<0.001). The duration of the effect of Compound A to suppress lipolysis was also dose-dependent (FIG. 1).

Figure 2:
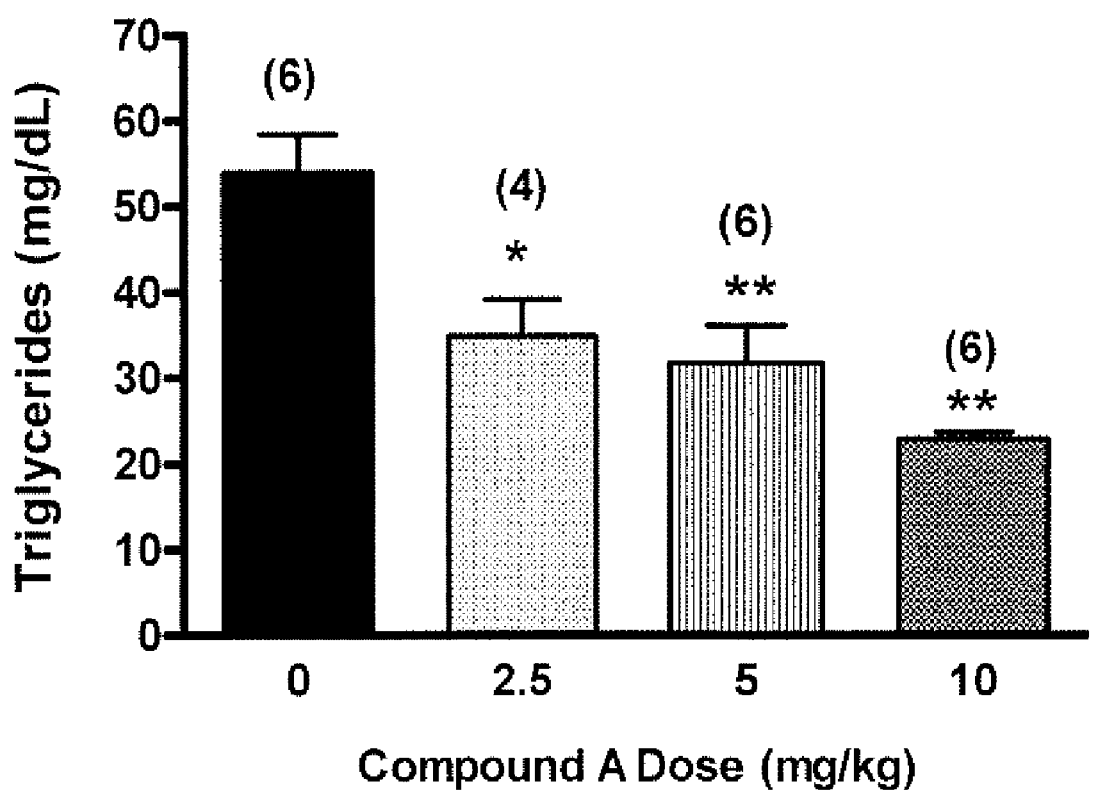
FIG. 2 shows the lipid lowering effects of Compound A as described in Example 31. Show is the maximal effect of various doses of Compound A (2.5, 5, and 10 mg/kg) on serum triglycerides (TG) in awake rats. The three were administered via oral gavage after an overnight fast. Values represent mean±SEM of the TG level from number of animals indicated in the parenthesis for each group. *) $p<0.05$, **) $p<0.01$ indicates values that are significantly different from vehicle (0) treated.

Compound A reduced serum triglyceride levels in a dose-dependent manner. The effect of three doses of Compound A on serum triglycerides is shown in FIG. 2. TG levels were significantly decreased (p<0.05) from 54±4 to 35±4 mg/dl at a dose of 2.5 mg/kg of Compound A, representing a 36% decrease. Doses of 5 and 10 mg/kg of Compound A, caused a 41% (32±4 mg/dl, p<0.01) and 58% (23±1 mg/dl, p<0.01) reduction in TG levels, respectively, compared to vehicle-treated rats.

Effect of Compound A on Triglyceride Production

Figure 3:
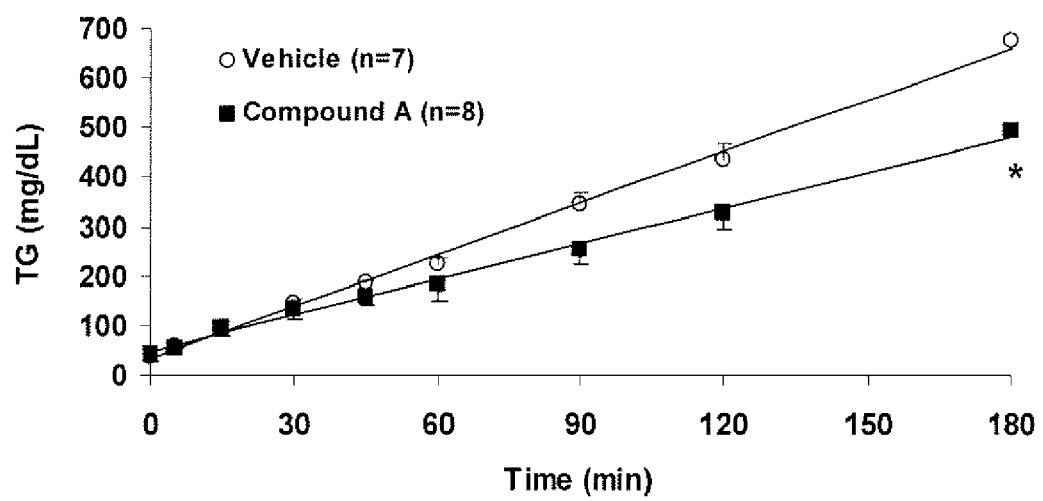
FIG. 3 graphs the time-dependent increase of TG caused by Triton WR 1229 in the absence or presence of Compound A as described in Example 31. After a 4 hour fast, rats received either vehicle or Compound A (5 mg/kg) via SC injection. After 5 minutes, Triton (400 mg/kg) was given as a slow intravenous bolus. Data are presented as ±SEM of values from 7-8 animals. Slope of the lines (determined by linear regression analysis) was 5.6±0.1 and 3.8±0.2 for vehicle and Compound A groups, respectively. Data were analyzed using 2 way ANOVA followed by Bonferroni's post hoc test.

To further investigate the mechanism of the decrease in TG levels by Compound A, total TG production was measured in normal rats. TG production was estimated by comparing the accumulation of TG in the plasma after an injection of Triton WR 1339 (Triton, 600 mg/kg) both in the absence and in the presence of Compound A (FIG. 3). Treatment of rats with Triton caused a time-dependent increase in serum TG in both vehicle- and Compound A-treated rats. The increase in serum TG caused by Triton was significantly less in Compound A-treated animals as compared to the vehicle-treated animals at 180 minutes post-treatment (p<0.01). TO accumulation as determined from the slope of the line (linear regression of the data) was also significantly less (p<0.001) in rats treated with Compound A. (5.6±0.12 mg/dl/min) as compared to vehicle-treated rats (3.8±0.17 mg/dl/min).

Lack of Tachyphylaxis to Repeated Treatment with Compound A

Figure 4:
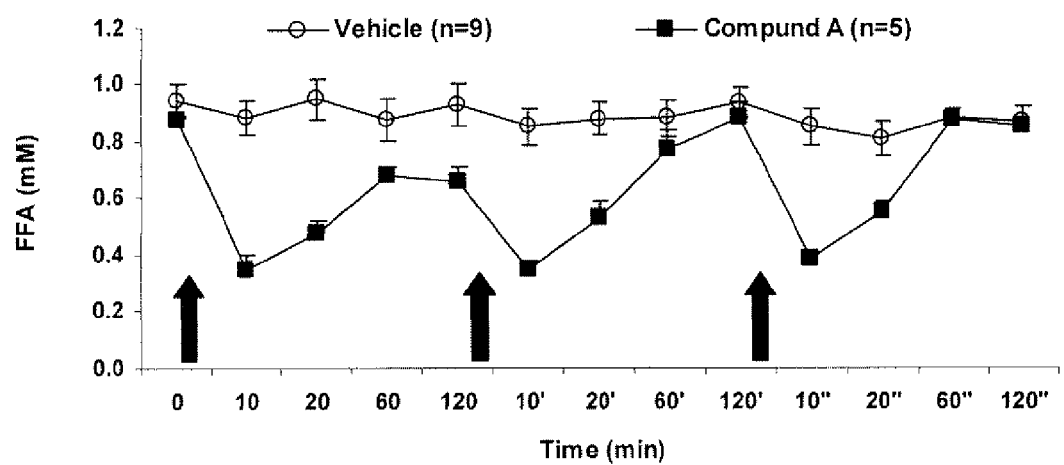
FIG. 4 shows the lack of acute desensitization (tachyphylaxis) of the FFA lowering effect of Compound A. Sown is the effect of three consecutive injection of Compound A on serum FFA levels in awake rats. Animals were fasted overnight and Compound A was given via IV bolus at a does of 1 mg/kg. Arrows indicate the times of Compound A dosing. Data are present as mean±SEM values of FFA from nine controls (vehicle treated) and five Compound A treated rats.

The decrease in FFA levels caused by Compound A was highly reproducible and did not undergo acute tachyphylaxis. As shown in FIG. 4, three repeated iv injections of Compound A (1 mg/kg) to rats caused similar decreases in FFA levels to 0.35±0.04, 0.35±0.03 and 0.38±0.03 mM, respectively, from a baseline value of 0.88±0.02 mM. The time-course of the decreases in plasma FFA levels caused by the three consecutive injections of Compound A was similar.

No Rebound with Compound A

Figure 5:
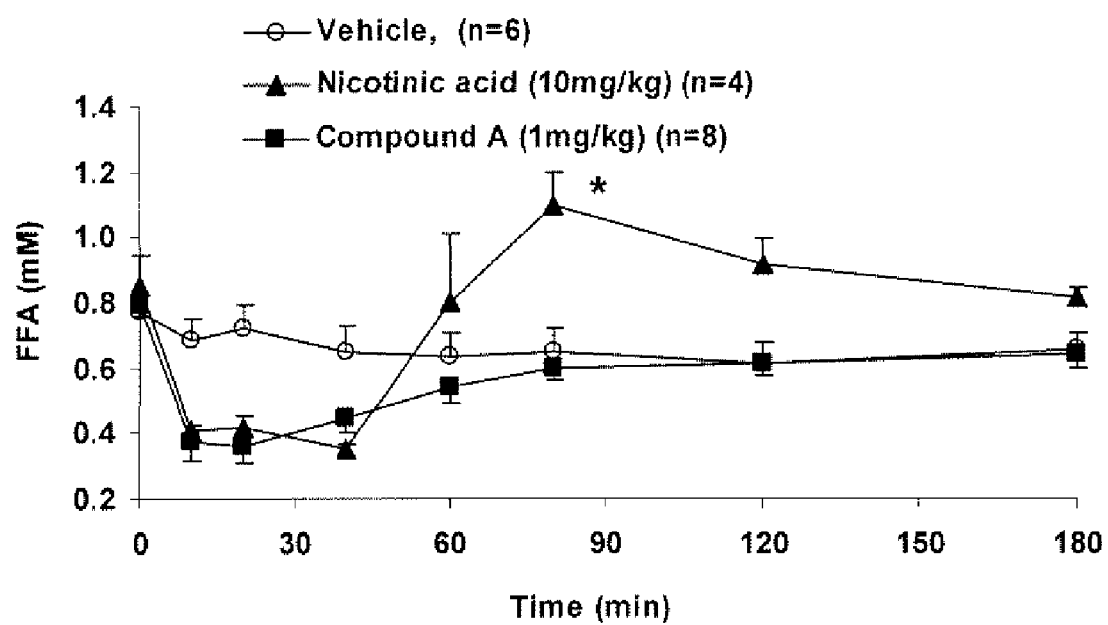
FIG. 5 presents the time-course of the effects of Compound A and nicotinic acid on serum FFA in awake rats. Animals were fasted overnight and were treated with vehicle, Compound A, or nicotinic acid via IV bolus injection. Data are presented as mean±SEM of the FFA level from four to eight rats in different groups. P<0.001 indicates significantly different from baseline at the same time point.

The anti-lipolytic effect of Compound A was compared to that of nicotinic acid in overnight-fasted awake rats. Compound A and nicotinic acid lowered FFA levels to 0.36±0.05 from 0.79±0.04 mM (p<0.001) and 0.35±0.01 from 0.85±0.09 nM (p<0.001), respectively (FIG. 5). Compound A (1 mg/kg, iv bolus) caused a maximal 54±5% decrease in FFA levels which was comparable to that caused by nicotinic acid (57±5%) given at a dose of 10 mg/kg iv bolus. The rebound increase of FFA levels seen with nicotinic acid was not observed with Compound A.

Effect of Compound A and Insulin on FFA Levels

Figure 6:
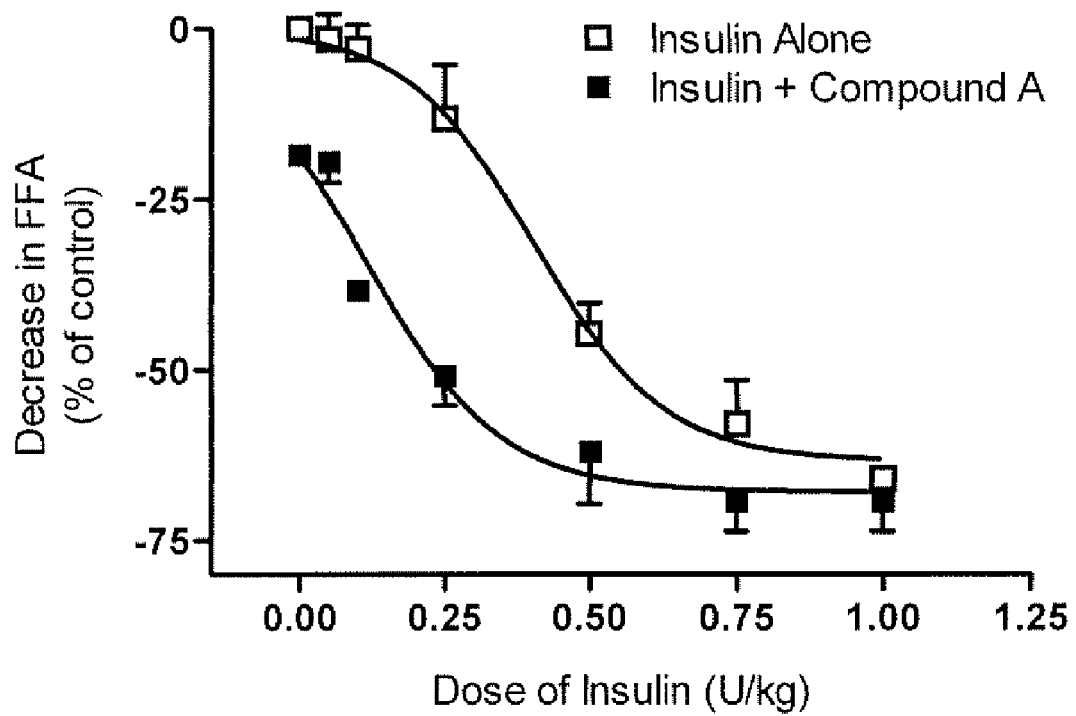
FIG. 6 graphically represents how Compound A potentates the effect of insulin in reducing FFA levels. Shown are the dose response curves for the effect of insulin to reduce FFA obtained in the absence and presence of Compound A (0.5 mg/kg) in awake rats. Both insulin and Compound A were given via IP injection. Each data point is the mean±SEM of the maximal (peak effect) percent decrease in FFA levels from baseline from three to five rats. The doses of insulin that cause a 50% decrease ($ED_{50}$) in FFA levels in the absence and presence of Compound A were 0.4 (0.3916-0.4208, 95% Cl) and 0.1 (0.0935-0.133) U/kg, respectively.

The effect of insulin (0.005-1 U/kg) to reduce serum FFA was determined in the absence and presence of a single dose (0.5 mg/kg) of Compound A (FIG. 6). Baseline FFA levels before insulin administration in vehicle and Compound A treated groups were 0.84±0.01 and 0.92±0.02 mM, respectively. As expected, insulin lowered FFA levels by up to 67±1% in a dose-dependent manner. The insulin dose response to reduce FFA levels was then repeated in the presence of Compound A (0.5 mg/kg). Compound A alone (0.5 mg/kg) caused an 18% decrease in FFA levels. The doses of insulin that cause 50% decrease ($ED_{50}$) in FFA levels in the absence and presence of Compound A were 0.4 and 0.1 U/kg, respectively. Thus, in the presence of Compound A, there was a 4-fold leftward shift of the insulin dose-response to lower FFA suggesting that Compound A increases insulin sensitivity in adipose tissue.

Cardiovascular Effects of Compound A

Figure 7:
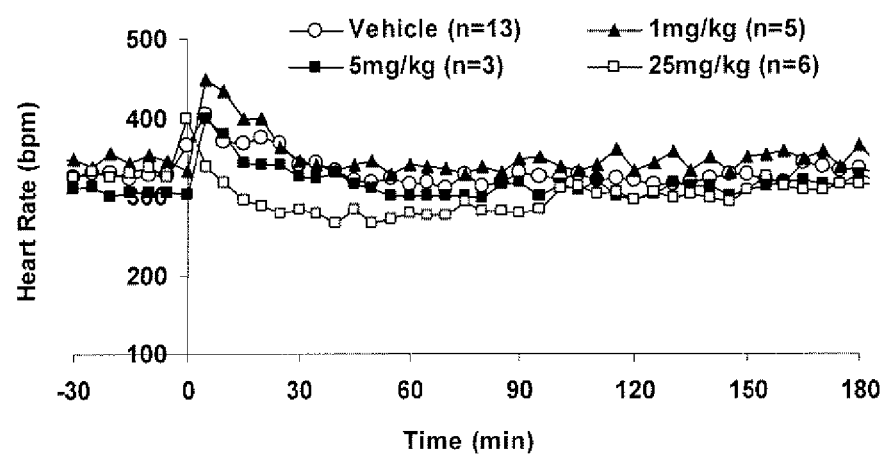
FIG. 7 presents the time-course of the effect of Compound A on (A) heart rate and (B) mean arterial pressure in awake rats as measured by telemetry. Compound A was given at various does (1, 5, and 25 mg·kg) by oral gavage at time 0. Each data point is the mean of individual values from the number of experiments indicated in parenthesis. The initial transient (10 Minutes) increase in heart rate subsequent to the injection of vehicle or Compound A is due to the stress caused by handling of the animals.
Figure 7:
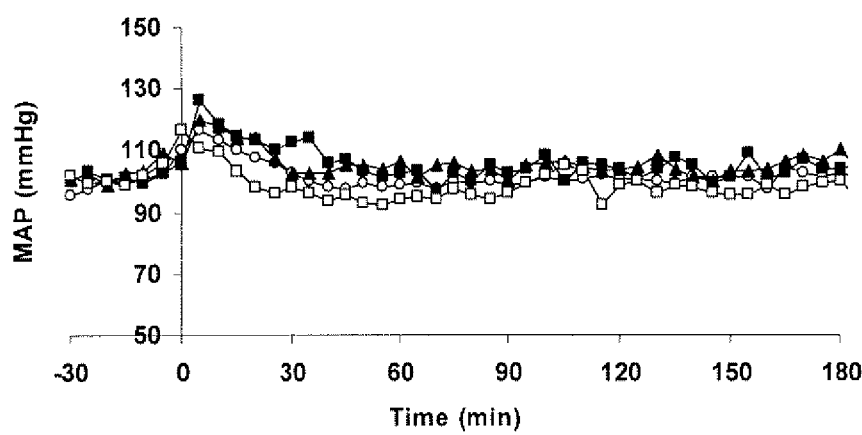

The effects of Compound A on heart rate and blood pressure were determined in by telemetry and the data are shown in FIG. 7. Compound A at doses of 1 and 5 mg/kg did not have a significant effect on heart rate but caused a small decrease (13±1% calculated as area under the curve) in heart rate at a dose of 25 mg/kg (FIG. 7A). Increasing the dose of Compound A to 50 mg/kg caused no further decrease in heart rate (data not shown). Compound A did not have any significant effect on blood pressure at the doses used (FIG. 7B).

In conclusion, data in the present example show that Compound A, an $A_1$ adenosine receptor agonist having the structure of Formula I, is an effective anti-lipolytic agent that lowers circulating FFA and TG levels, and improves insulin sensitivity in adipose tissue. The anti-lipolytic effect of Compound A is not associated with a rebound increase FFA. The FFA-lowering effects occur at doses that have no effect on heart rate. The pharmacological properties of Compound A suggest that this compound may have therapeutic utility in metabolic and cardiovascular disorders in which FFA levels are increased.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto. All patents and publications cited above are hereby incorporated by reference.

Example 32

Biological Activity

Improvement of Insulin Resistance

There is substantial evidence in the literature that elevated plasma free fatty acid (FFA) play a role in the pathogenesis of type 2 diabetes. Compound A is a selective partial $A_1$ adenosine receptor agonist which inhibits lipolysis and lowers circulating FFA. The present study determined the effect of Compound A on insulin resistance induced by high fat diet in rodents. High fat (HF) diet feeding to rats for 2 weeks caused a significant increase in insulin, FFA and TG concentrations as compared to rats fed chow. Compound A (1 mg/kg) caused a time dependent decrease in FFA, TG and insulin levels. An acute treatment with Compound A significantly lowered the insulin response whereas glucose response was not different to an oral glucose tolerance test (OGTT). Treatment with Compound A for 2 weeks resulted in significant lowering of FFA, TG and insulin levels in rats on high fat diet. OGTT at the end of the 2 week treatment showed that glucose levels did not change, whereas the total integrated plasma insulin response was significantly (p<0.05) lower in Compound A group. To determine the effect of Compound A on insulin sensitivity, hyperinsulinemic euglycemic clamp studies were performed in C57BL/J6 mice fed HF diet for 12 weeks. Glucose infusion rate (GIR) was decreased significantly in HF mice as compared to chow-fed mice. Compound A treatment 15 min prior to the clamp study significantly (p<0.01) increased GIR to values to that for chow-fed mice. In conclusion, Compound A treatment lowers FFA. TG concentrations and improves insulin sensitivity in rodent models of insulin resistance.

Materials and Methods

Rat Studies

All experimental procedures were performed under a protocol approved by the IACUC (CV Therapeutics, Inc.) and in accordance with the recommendations set forth in the Guide for the Care and Use of Laboratory Animals published by the National Research Council. Male Sprague-Dawley rats (225-250 gm) with either one or two indwelling catheters (carotid and jugular) were obtained from Charles River Laboratories (Wilmington, Mass.). Animals were housed 1 per cage in a room maintained on a 12 h light/dark cycle (light on 06.00-18.00 h) under constant temperature (22-25° C.) and with ad libitum access to food and water. Rats on normal diet (Chow) were fed standard laboratory chow (12% fat, 60% carbohydrate, and 28% protein) throughout the study, while animals in the high fat (HF) diet group were given a diet (TD88137 from Harlan Teklad, Madison, Wis.) containing 42% fat, 43% carbohydrate, and 15% protein.

The anti-lipolytic effects of Compound A (see chemical name below) were studied in awake rats. On the day of the experiment, animals were put in metabolic cages and left undisturbed to acclimate to the environment for 1-2 hrs. An infusion set (21 G×¾", 0.8×19 mm U.T.W., 3½", 9 cm tubing, volume 0.15 ml) was connected to the arterial catheter for blood sampling. A 1% sodium citrate saline solution was used to flush the lines. A pre-treatment blood sample was obtained from each animal to determine baseline values for glucose, insulin, FFA and TG. Blood samples were collected into plasma and serum separator tubes (Becton Dickinson, Franklin Lakes, N.J.) at pre-determined time points. Oral glucose tolerance test (OGTT) was performed by giving 2 gm/kg of glucose load. Compound A was given via an oral gavage 15 minutes prior to the glucose load. For chronic experiments Compound A was administered twice a day via subcutaneous injection at a dose of 5 mg/kg for 2 weeks. An OGTT was performed at the end of two weeks at ~2 hrs after the last dose of Compound A.

Mouse Studies

C57BL/J6 mice were maintained on normal chow or a HF diet (Bovine Lard, 23 wt/wt %, 44 energy % provided by the lard) for 12 weeks to induce insulin resistance. At the end of 12 weeks a hyperinsulinemic euglycemic clamp analysis was performed to measure insulin sensitivity in the absence and presence of Compound A. Compound A was given via an ip injection 15 minutes before the clamp protocol was started. After an overnight fast, glucose turnover studies were performed as described previously (6; 11).

Briefly, animals were anesthetized; an infusion needle was placed in one of the tail veins. Thereafter, a bolus of insulin was given and a hyperinsulinemic clamp was started by continuous infusion of insulin. Blood samples were taken every 10 minutes (tail bleeding) to monitor plasma glucose levels. A variable infusion of 12.5% D-glucose (in PBS) solution was started at time 0 and adjusted to maintain blood glucose at ~6.0 mM. When steady state glucose levels were reached (approximately 1 hour after start of the insulin infusion) a final blood sample was taken (for measurement of plasma insulin) and the hyperinsulinemic euglycemic clamp was terminated. There were no significant differences in blood glucose or plasma insulin levels between the three groups of mice during the clamp analysis.

Chemicals and Reagents

Compound A (2-{6-[((1R,2R)-2-hydroxycyclopentyl)amino]purin-9-yl}(4S,5S,2R,3R)-5-[(2-fluorophenylthio)methyl]oxolane-3,4-diol) was synthesized by the Department of Medicinal and Bio-Organic chemistry of CV Therapeutics, Inc. Sodium citrate was purchased from Sigma (St. Louis, Mo.). PEG 400 was purchased from VWR (by EMD Chemicals). Triton WR1339 was diluted in warm saline (~37° C.) with frequent vortexing. Compound A was dissolved in. PEG 400, and then diluted with distilled water to make a 20% PEG drug solution. FFA and TGs were measured using commercial kits from Wako Chemicals, (Richmond, Va.). Glucose and Insulin were measured using commercial kits from Thermo Electron Corporation (Waltham, Mass.) and Crystal Chem (Downers Grove, Ill.), respectively.

Data Analysis

All data are reported as mean±SEM. Statistical analysis of data from experiments with 2 treatment groups was performed using the unpaired Student's t-test. One way analysis of variance (ANOVA) followed by Newman-Keuls posthoc analysis was used for multiple comparisons. Data form OGTT was analyzed by calculating area under the curve (AUC) using prism graphpad software. Differences between/among treatment groups were considered to be significant when the probability of their occurrence by chance alone was <0.05.

Results

Effect of High Fat Diet

Table 1 presents the weight and metabolic characteristics after two weeks in which rats were fed either conventional chow or the HF diet. It can be seen that there were no significant differences in either the body weight or the plasma glucose concentrations of the two groups (Table 1). However, insulin, FFA, and TG concentrations were all significantly higher in rats fed the HF diet as compared to the rats fed chow.

TABLE 1

Baseline characteristics of Sprague Dawley rats fed normal chow (Chow) and high fat diet (HF). Values are presented as Mean (±SEM).

|  | CHOW (N = 10) | HF (N = 9) | P VALUE |
|---|---|---|---|
| Body Weight (gms) | 306 ± 8 | 325 ± 11 | 0.23 |
| Glucose (mg/dl) | 175 ± 12 | 186 ± 9 | 0.45 |
| Insulin (ng/ml) | 2.0 ± 0.3 | 4.2 ± 0.9 | 0.028 |
| FFA (mM) | 0.55 ± 0.04 | 1.07 ± 0.1 | <0.001 |
| TG (mg/dl) | 54 ± 8 | 118 ± 15 | 0.001 |

Figure 8:
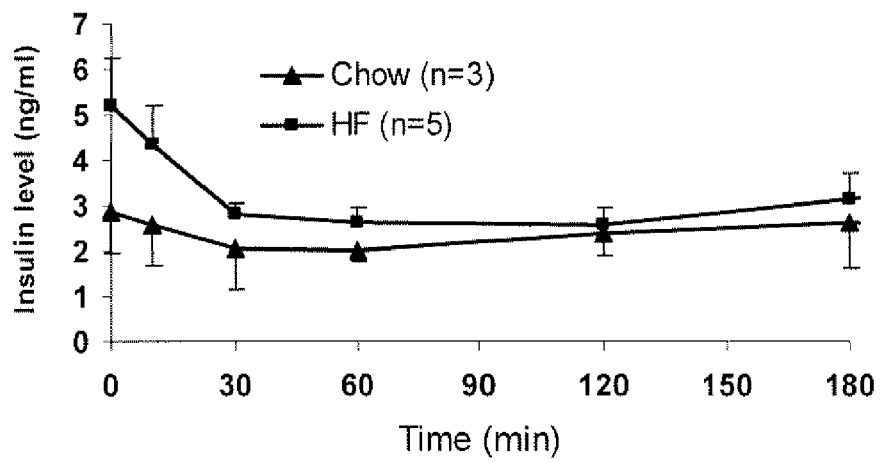
FIG. 8 graphically illustrates the time-course of the effect of Compound A on serum (A) insulin, (B) free fatty acids (FFA), and (C) triglycerides (TG) in rats fed normal diet (ND) and high fat diet (HFD) for 2 weeks as discussed in Example 32. Animals were fasted for four hours before the experiment. Compound A was administered via oral gavage at a dose of 1 mg/kg. Values represent mean±SEM from number of animals indicated in the parenthesis for each group.
Figure 8:
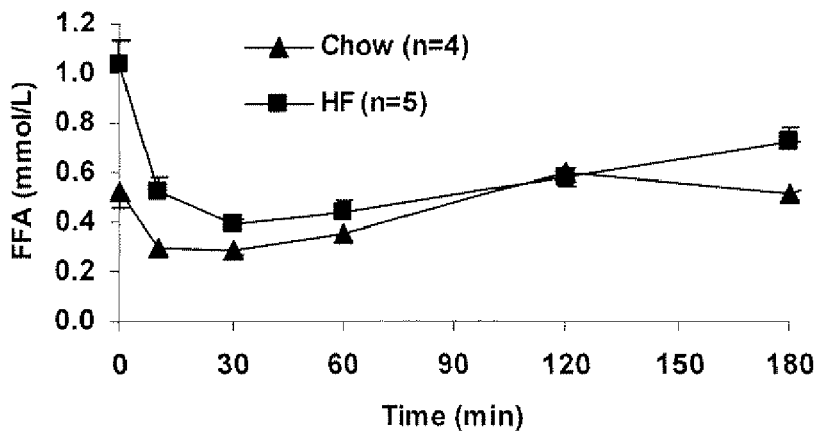
Figure 8:
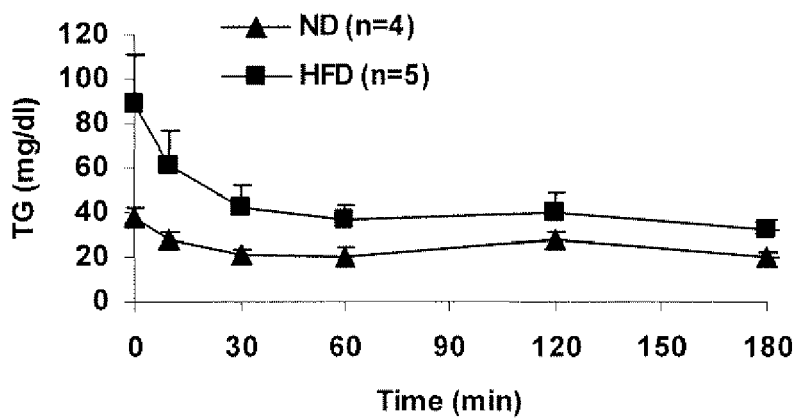

Rats were fasted for 4 hrs before taking blood samples for glucose, insulin, FFA and TG analysis.
HF; High Fat,
FFA; Free Fatty acids,
TG; Triglycerides Acute Studies in Rats The acute effects of an oral administration of Compound A (1 mg/kg) on plasma FFA, TG, and insulin concentrations in rats fed either chow or the HF diet are shown in FIG. 8. Consistent with the results in Table 1, baseline concentrations of these three variables were higher in the HF-fed rats. Although FFA, TG, and insulin concentrations fell promptly in response to Compound A in both groups, the results in Table 2 show that the magnitude of the response was greater for all three variables in the HF group. Consequently, FFA, TG, and insulin concentrations were essentially identical in the two groups from the 60 min time point to the end of the experiment.

TABLE 2

Mean (±SEM) decrease in FFA, TG, and insulin concentrations from 0 to 30 min following Compound A treatment.

| VARIABLE | GROUP | | P VALUE |
| --- | --- | --- | --- |
| | Chow | HF | |
| Insulin (ng/ml) | 0.8 ± 0.32 | 2.37 ± 0.85 | 0.09 |
| FFA (mM) | 0.24 ± 0.07 | 0.65 ± 0.1 | <0.001 |
| TG (mg/dl) | 17 ± 3 | 46 ± 15 | 0.047 |

Rats were fasted for 4 hrs before taking the baseline sample. Compound A was given by an oral gavage at a dose of 1 mg/kg.
HF; High Fat,
FFA; Free Fatty acids,
TG; Triglycerides.

Figure 9A:
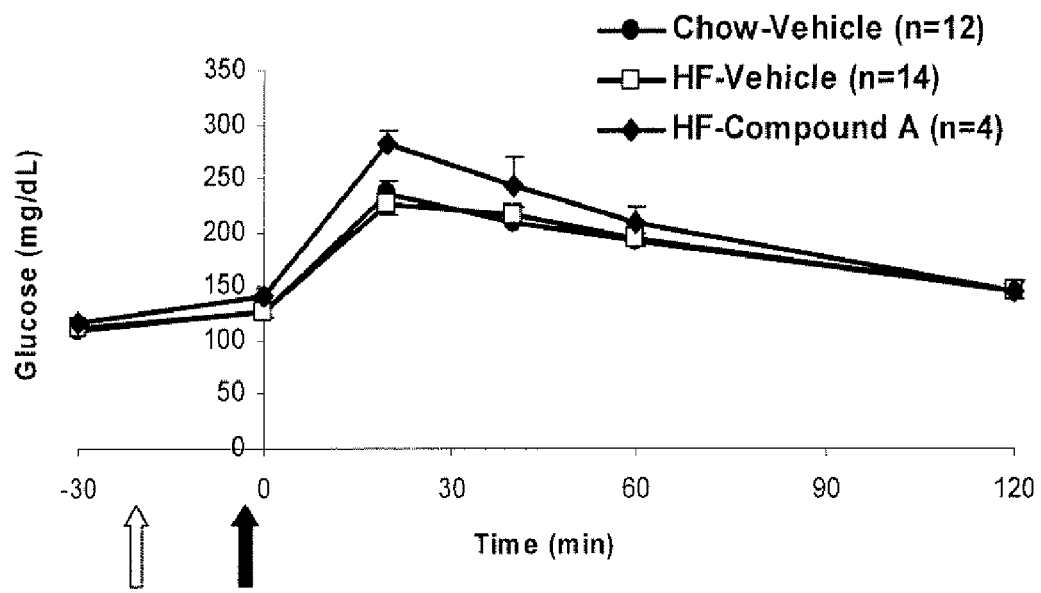
FIG. 9 shows the effects of Compound A on (A) glucose and (B) insulin levels during an oral glucose tolerance test in overnight fasted rats as described in Example 32. Compound A was given in a single dose of 1 mg/kg via an oral gavage 15 minutes prior to the glucose load. The white arrow indicated the time of Compound A treatment and the black arrow indicates the time of glucose load. Data is presented as mean±SEM from number of animals indicated in the parenthesis for each group. AUC of insulin for HF-vehicle treated group was significantly (p<0.01) increased. Compound A treatment of HF group significantly (p<0.05) decreased AUC for insulin as compared to untreated HF group.
Figure 9B:
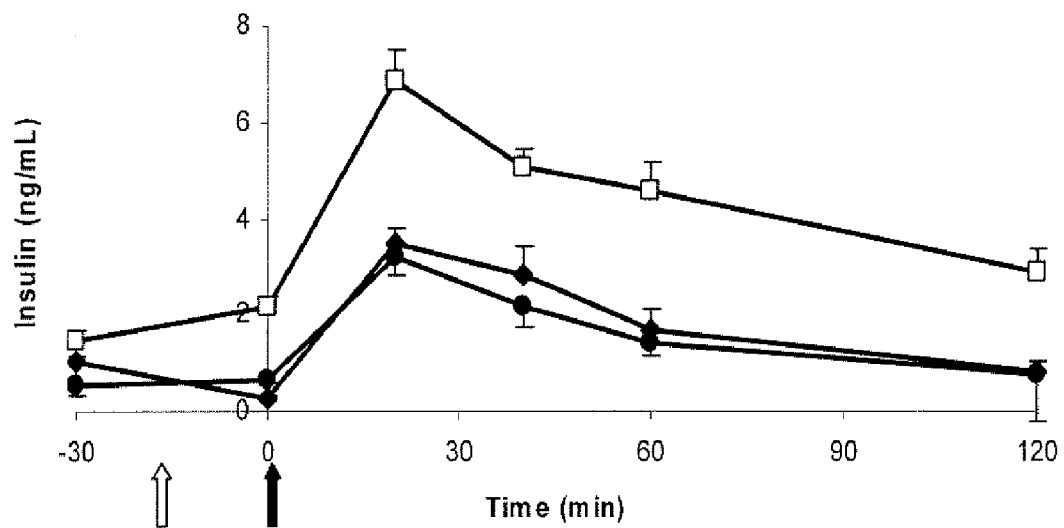

FIG. 9 depicts the glucose and insulin responses to an oral glucose load in three groups of rats, fed either chow (one group) or the HF diet (two groups) for 2 weeks. Chow-fed rats were gavaged with vehicle, whereas one group of the rats fed the HF diet received vehicle, while the other group was given Compound A 15 minutes prior to giving the glucose load. Glucose concentrations are shown in the top panel, and there were no differences between the total glucose response areas of the three experimental groups. Post-glucose challenge insulin concentrations are shown in the lower panel, and indicate that the total insulin response area in the saline-treated, HF diet group was significantly greater than that of the area two groups (p<0.01), whereas the total insulin response of HF-fed rats treated with Compound A was no different than the insulin response of chow-fed rats given vehicle (p<0.05).

Chronic Studies in Rats

Figure 10:
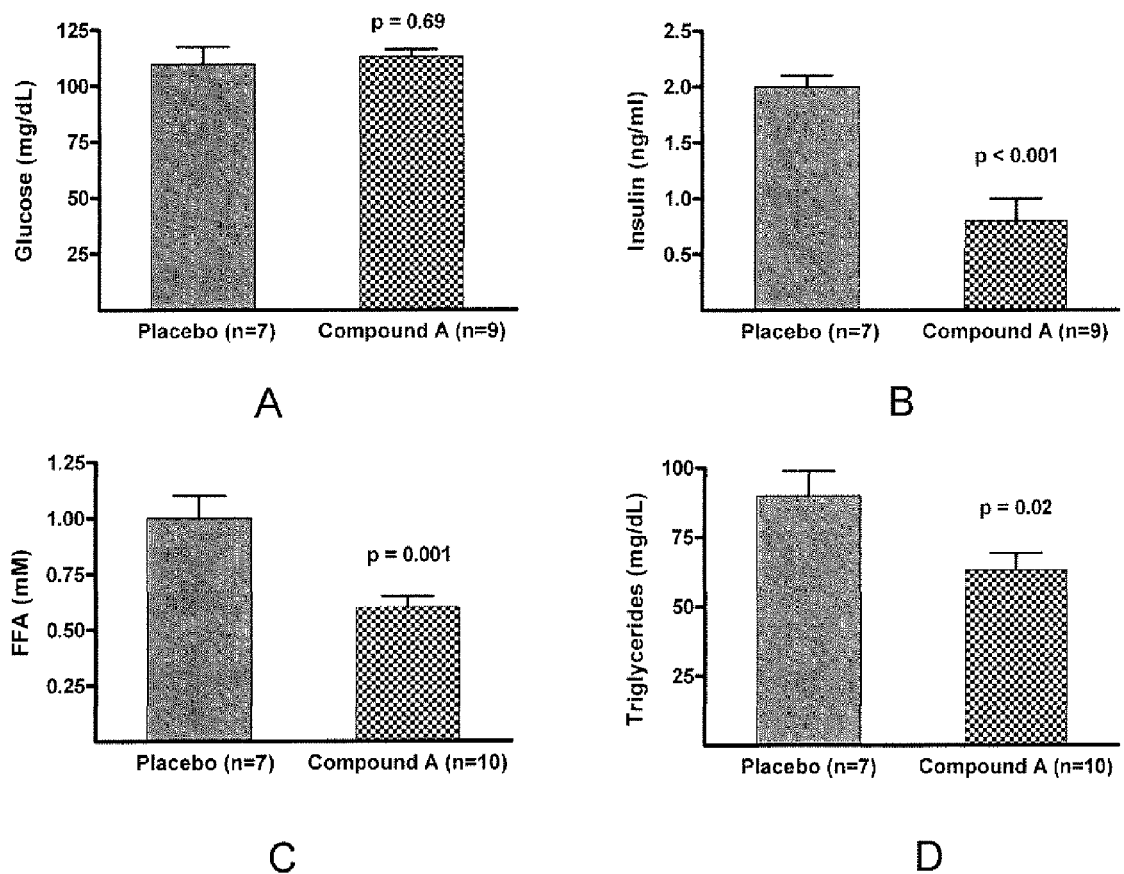
FIG. 10 graphs the effects of Compound A treatment on (A) glucose, (B) insulin, (C) FFA, and (D) triglyceride fasting levels in rats fed a high fat diet as explained in Example 32. Animals were fasted overnight before taking samples. Compound A was given via SC injection for 2 weeks at a dose of 5 mg/kg. Data is presented as mean±SEM from number of animals indicated below each bar.

The effect of chronic treatment with Compound A as compared to vehicle placebo (PLB) on glucose, insulin, FFA, and TG concentrations is shown in FIG. 10. Although there were no significant differences in glucose concentrations, rats fed a HF diet had significantly lower insulin, FFA, and TG concentrations when they received daily subcutaneous injections of Compound A (5 mg/kg) for two weeks.

Figure 11:
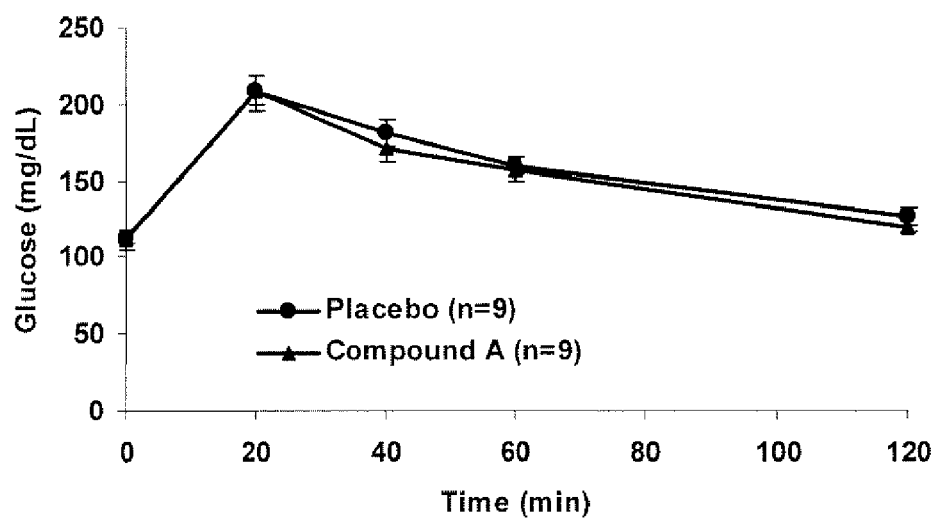
FIG. 11 shows the effects of Compound A on (A) glucose and (B) insulin levels during an oral glucose tolerance test in rats fed a high fat diet as described in Example 32. Animals were fasted overnight before taking samples. Compound A was given twice daily via a SC injection for 2 weeks at a dose of 5 mg/kg. Data is presented as mean±SEM from number of animals indicated in the parenthesis for each group. AUC of insulin for Compound A treated group was significantly lower than for placebo group (p<0.037).
Figure 11:
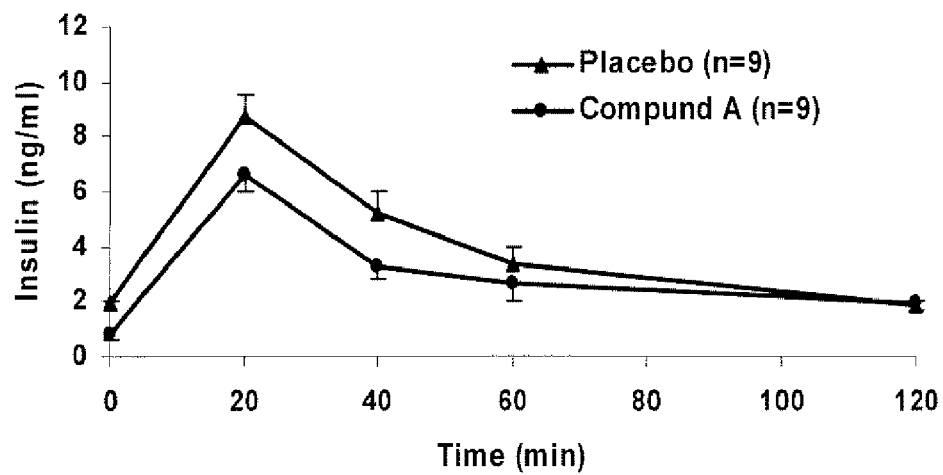

Plasma glucose and insulin responses to an oral glucose challenge in HF-fed rats following a two week period in which they received either subcutaneous injections of vehicle or Compound A (5 mg/kg) twice a day are shown in FIG. 11. Glucose levels (panel A) did not vary as a function of the treatment, whereas the total integrated plasma insulin levels (panel B) was significantly (p<0.05) lower in Compound A-treated rats.

Mouse Studies

Figure 12:
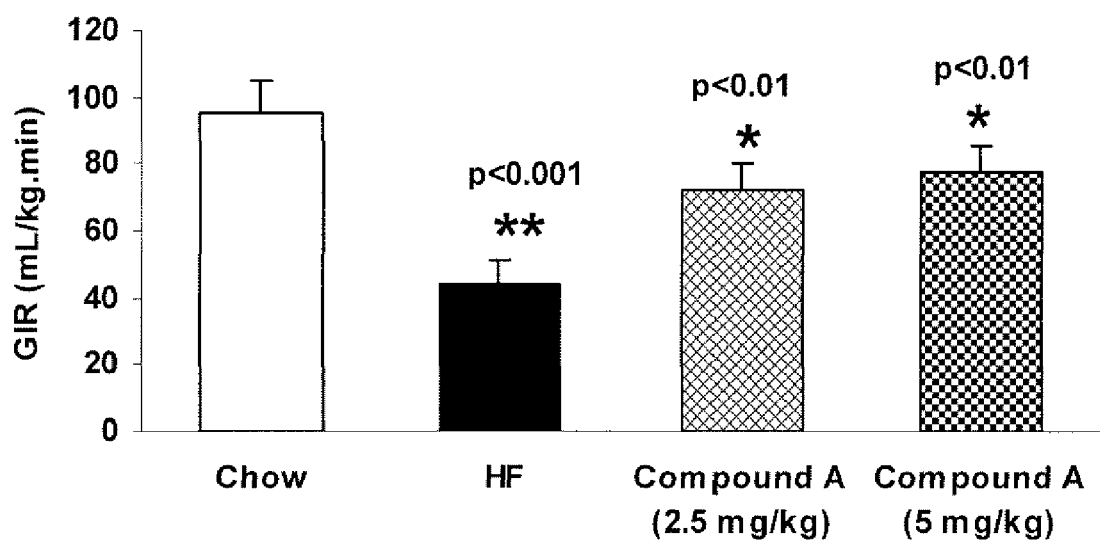
FIG. 12 presents glucose infusion rates (GIR) in C57Bl mice on a normal diet (Chow), a high fat diet (HF) for 12 weeks, and for animals on a 12 week HF that were treated with 2.5 mg/kg or 5.0 mg/kg doses of Compound A given twice via an Ip injection 15 minutes prior to hyperinsulinemic euglycemic clamp analysis. The HF group was significantly different (p<0.001) from the chow group while both dose of Compound A showed significant differences (p<0.01) from the untreated HF group.

By inference, the results described above are consistent with evidence that insulin resistance develops in rats fed HF diet, and that administration of Compound A attenuates the diet-induced impairment in insulin action. Hyperinsulinemic, euglycemic clamp studies were performed in order to test this hypothesis. The results in FIG. 12 demonstrate that insulin-mediated glucose disposal was decreased significantly in mice fed the HF diet for 12 weeks as compared to chow-fed mice. However, the intra-peritoneal injection of two doses of Compound A 15 min prior to beginning the clamp study enhanced insulin sensitivity, and the values of insulin-mediated glucose disposal in the Compound A-treated rats were significantly greater (p<0.01) than in saline-injected mice fed a HF diet and no different than in chow-fed mice.

What is claimed is:

1. A method of increasing insulin sensitivity in a mammal in need thereof, comprising administering to a mammal in need thereof a therapeutically effective dose of a compound of Formula I:

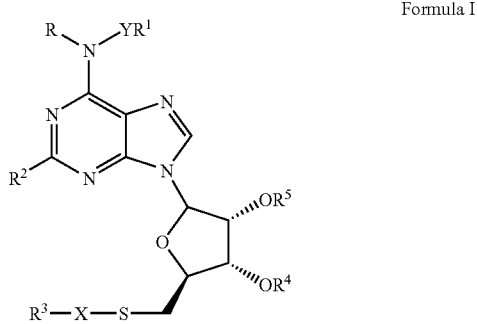

Formula I wherein:
R is hydrogen or lower alkyl;
$R^1$ is cycloalkyl optionally substituted with hydroxyl;
$R^2$ is hydrogen, halo, trifluoromethyl, acyl, or cyano;
$R^3$ is aryl optionally substituted with halogen or alkyl;
$R^4$ and $R^5$ are independently hydrogen or acyl; and
X and Y are independently a covalent bond or optionally substituted alkylene.

2. The method of claim 1, wherein R, $R^2$, $R^4$ and $R^5$ are all hydrogen.

3. The method of claim 2, wherein X is a covalent bond and $R^3$ is optionally substituted phenyl.

4. The method of claim 3, wherein Y is a covalent bond, $R^1$ is optionally substituted cyclopentyl and $R^3$ is phenyl substituted by halogen or alkyl.

5. The method of claim 4, wherein $R^1$ is 2-hydroxycyclopentyl, $R^3$ is 2-fluorophenyl, and the compound is (4S,5S,2R,3R)-5-[(2-fluorophenylthio)methyl]-2-{6-[(2-hydroxycyclopentyl)amino]-purin-9-yl}oxolane-3,4-diol.

6. The method of claim 4, wherein $R^1$ is 2-hydroxycyclopentyl, $R^3$ is 3-fluorophenyl, and the compound is 2-{6-[((1R,2R)-2-hydroxycyclopentyl)amino]purin-9-yl}(4S,5S,2R,3R)-5-[(3-fluorophenylthio)methyl]oxolane-3,4-diol.

7. The method of claim 4, wherein $R^1$ is 2-hydroxycyclopentyl, $R^3$ is 2-chlorophenyl, and the compound is 2-{6-[((1R,2R)-2-hydroxycyclopentyl)amino]purin-9-yl}(4S,5S,2R,3R)-5-[(2-chlorophenylthio)methyl]oxolane-3,4-diol.

8. The method of claim 4, wherein $R^1$ is 2-hydroxycyclopentyl, $R^3$ is 2,4-difluorophenyl, and the compound is 2-{6-[((1R,2R)-2-hydroxycyclopentyl)amino]purin-9-yl}(4S,5S,2R,3R)-5-[(2,4-difluorophenylthio)methyl]oxolane-3,4-diol.

9. The method of claim 4, wherein $R^1$ is 2-hydroxycyclopentyl, $R^3$ is 4-chlorophenyl, and the compound is 2-{6-[((1R,2R)-2-hydroxycyclopentyl)amino]purin-9-yl}(4S,5S,2R,3R)-5-[(4-chlorophenylthio)methyl]oxolane-3,4-diol.

10. The method of claim 4, wherein R1 is 2-hydroxycyclopentyl, $R^3$ is 4-fluorophenyl, and the compound is 2-{6-[((1R,2R)-2-hydroxycyclopentyl)amino]purin-9-yl}(4S,5S,2R,3R)-5-[(4-fluorophenylthio)methyl]oxolane-3,4-diol.

11. The method of claim 4, wherein R1 is 2-hydroxycyclopentyl, $R^3$ is 2,6-dimethylphenyl, and the compound is 2-{6-[((1R,2R)-2-hydroxycyclopentyl)amino]purin-9-yl}(4S,5S,2R,3R)-5-[(2,6-dimethylphenylthio)methyl]oxolane-3,4-diol.

12. The method of claim 4, wherein R1 is 2-hydroxycyclopentyl, $R^3$ is 2-methylphenyl, and the compound is 2-{6-[((1R,2R)-2-hydroxycyclopentyl)amino]purin-9-yl}(4S,5S,2R,3R)-5-[(2-methylphenylthio)methyl]oxolane-3,4-diol.

13. A pharmaceutical composition comprising at least one pharmaceutically acceptable excipient and a therapeutically effective amount of a compound of Formula I

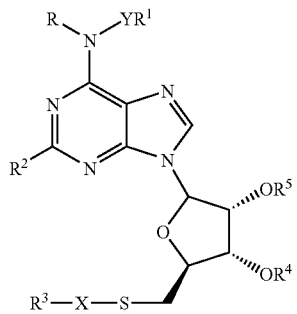

Formula I wherein:

R is hydrogen or lower alkyl;

$R^1$ is optionally substituted with hydroxyl $R^2$ is hydrogen, halo, trifluoromethyl, acyl, or cyano;

$R^3$ is optionally substituted with halogen or alkyl;

$R^4$ and $R^5$ are independently hydrogen or acyl; and

X and Y are independently a covalent bond or optionally substituted alkylene.

* * * * *